(12) United States Patent
Vande Berg et al.

(10) Patent No.: US 9,045,765 B2
(45) Date of Patent: *Jun. 2, 2015

(54) EPSP SYNTHASE GENES CONFERRING HERBICIDE RESISTANCE

(75) Inventors: Brian Vande Berg, Durham, NC (US); Cheryl Peters, Raleigh, NC (US); Brian Carr, Raleigh, NC (US); Daniel John Tomso, Bahama, NC (US)

(73) Assignee: Athenix Corporation, Morrisville, NC (US)

( * ) Notice: Subject to any disclaimer, the term of this patent is extended or adjusted under 35 U.S.C. 154(b) by 1529 days.

This patent is subject to a terminal disclaimer.

(21) Appl. No.: 11/760,570

(22) Filed: Jun. 8, 2007

(65) Prior Publication Data

US 2007/0289035 A1    Dec. 13, 2007

Related U.S. Application Data

(60) Provisional application No. 60/812,360, filed on Jun. 9, 2006.

(51) Int. Cl.
  *C12N 15/82*    (2006.01)
  *C12N 9/10*    (2006.01)

(52) U.S. Cl.
  CPC ........ *C12N 15/8275* (2013.01); *C12N 15/8261* (2013.01); *C12N 9/1092* (2013.01)

(58) Field of Classification Search
  None
  See application file for complete search history.

(56) References Cited

U.S. PATENT DOCUMENTS

| | | | |
|---|---|---|---|
| 5,094,945 A | 3/1992 | Comai | |
| 5,188,642 A | 2/1993 | Shah et al. | |
| 5,312,910 A | 5/1994 | Kishore et al. | |
| 5,627,061 A * | 5/1997 | Barry et al. | 800/288 |
| 6,040,497 A | 3/2000 | Spencer et al. | |
| 6,225,114 B1 | 5/2001 | Eichholtz et al. | |
| RE37,287 E | 7/2001 | Lebrun et al. | |
| 6,566,587 B1 | 5/2003 | Lebrun et al. | |
| 6,867,293 B2 | 3/2005 | Andrews et al. | |
| 7,045,684 B1 | 5/2006 | Held et al. | |
| 7,141,722 B2 | 11/2006 | Fincher et al. | |
| 7,183,110 B2 | 2/2007 | Barry et al. | |
| 7,214,535 B2 | 5/2007 | Sun et al. | |
| 2003/0049814 A1 | 3/2003 | Andrews et al. | |
| 2003/0079246 A1 | 4/2003 | Andrews et al. | |
| 2003/0200560 A1 | 10/2003 | Warner et al. | |
| 2004/0148650 A1 | 7/2004 | Baerson et al. | |
| 2005/0223436 A1 | 10/2005 | Lin et al. | |
| 2005/0246798 A1 * | 11/2005 | Castle et al. | 800/300 |
| 2006/0143727 A1 | 6/2006 | Alibhai et al. | |
| 2007/0136840 A1 | 6/2007 | Peters et al. | |

FOREIGN PATENT DOCUMENTS

| | | |
|---|---|---|
| EP | 1510581 A | 3/2005 |
| JP | 2001178447 A | 7/2001 |
| WO | WO 2004/056179 A2 | 7/2004 |
| WO | WO 2004/056179 A3 | 7/2004 |

OTHER PUBLICATIONS

Merabet et al 1993, Biochemica et Biophysica Acta 1161: 272-278.*
Eschenburg, Susanne et al., "How the mutation glycine96 to alanine confers glyphosate insensitivity to 5-enolpyruvyl shikimate-3-phosphate synthase from *Escherichia coli*," Planta (Berlin), Nov. 2002, pp. 129-135, vol. 216, No. 1.
Sun, Yi-Cheng et al. "Novel AroA with High Tolerance to Glyphosate, Encoded by a Gene of *Pseudomonas putida* 4G-1 Isolated from an Extremely Polluted Environment in China," *Applied and Environmental Microbiology*, Aug. 2005, pp. 4771-4776, vol. 71, No. 8.
Geneseq Database Report for Accession No. ADS21268, first entry, Dec. 2, 2004.
NCBI Database Report for Accession No. BAD59440, direct submission on Sep. 26, 2003.
NCBI Database Report for Accession No. YP_075248, direct submission on Sep. 7, 2004.
NCBI Database Report for Accession No. YP_098022, direct submission on Oct. 1, 2004.
NCBI Database Report for Accession No. YP_832132, direct submission on Oct. 25, 2006.
Partial Search Report issued on Apr. 29, 2011 for European Patent Application No. 10013988.0.
EBI Database Accession No. Q67P19, Ueda et al. (2004) Nucleic Acids Res. 32:4937-4944.
EBI Database Accession No. EM_PAT:DD253522; Japanese Patent No. 2005530497-A/1C, issued Aug. 5, 2002.

* cited by examiner

*Primary Examiner* — David H Kruse

(57) ABSTRACT

Compositions and methods for conferring herbicide resistance or tolerance to bacteria, plants, plant cells, tissues and seeds are provided. Compositions comprising a coding sequence for a polypeptide that confers resistance or tolerance to glyphosate herbicides are provided. The coding sequences can be used in DNA constructs or expression cassettes for transformation and expression in plants. Compositions also comprise transformed bacteria, plants, plant cells, tissues, and seeds. In particular, isolated nucleic acid molecules corresponding to glyphosate resistant nucleic acid sequences are provided. Additionally, amino acid sequences corresponding to the polynucleotides are encompassed. In particular, the present invention provides for isolated nucleic acid molecules comprising nucleotide sequences encoding the amino acid sequence shown in SEQ ID NOS:2, 4, 6, 8, 10, 12, or 14 or the nucleotide sequence set forth in SEQ ID NOS:1, 3, 5, 7, 9, 11, 13, 28, 29, 30, 31, 32, 33, or 34.

23 Claims, 5 Drawing Sheets

```
GRG1   ---------------------------------MKVTIQPGDLTGILQSPASKSSM  23
GRG5   -----------------------------MRPQATLTVLPVERPLVGRVSPPGSKSIT 29
GRG6   -----------------------------MRPQATLTVMPVERPLVGRVSPPGSKSIT 29
GRG7   -----------------------------MRPQATLTVLPVERPLVGRVSPPGSKSIT 29
GRG8   ----------------------------MMMGRAKLTIIPPGKPLTGRAMPPGSKSIT 30
GRG9   --------------------------------MIELTITPPGHPLSGKVEPPGSKSIT 26
GRG10  ----------------------------------MNCVKINPCCLKGDIKIPPSKSLG 24
GRG12  -----MACLPDDSGPHVGHSTPPCLDQEPCTLSSQKTVTVTPPNFPLTGKVAPPGSKSIT 55
GRG15  --------------------------------MIELTITPPGHPLSGKVEPPGSKSIT 26
GRG20  ------------------------------------MIVKIYPSKISGIIKAPQSKSLA 23
GRG21  --------------------------------MRNMNKKIIKADKLVGEVTPPPSKSVL 27
GRG22  -----------------------------------MKRVELEGIPEVRGTVCPPPSKSGS 25
GRG23  --------------------MALERGQHGRSRRLFGASLERITMETDRLVIPGSKSIT 38
GRG25  MLLRTVKTCLEPKDLPICTASAPGSPTDKLHNAEKTWWAAPHAATGLDAIVSVPASKSLT 60
GRG26  -------------MPGTPATQTDD-SGTSTASALPLWPAPFASHPVDATVTVPGSKSLT 45
GRG27  -------------MTGTTAANTE----PDKAASLPLWPAPYANGPVDATVTVPGSKSLT 42
GRG28  -------------MTGTTAANTG----SNSVDTLPLWAAPYATRPVDATVTVPGSKSLT 42
GRG29  ------------------------------MDVIVKPTPSLNGEIGALSSKNYT 24
GRG30  ------------------------------MDVIVKPTPSLNGEIGALSSKNYT 24
GRG31  -----------------------------MNQQVITLTHPSKKIQGTVQLTGSKSES 28
                                                      **.

GRG1   QRACAAALVAKGISEIINPGHSNDDKAARDIVSRLGARLEDQPDGSLQITSEGVKPVAP-  82
GRG5   NRALLLAGLAKGTSRLTGALKSDDTRVMSEALRLMGVQVDEPDDSTFVVTSSGHWQAP-- 87
GRG6   NRALLLAGLAKGTSRLTGALKSDDTRVMSEALRLMGVQVDEPDDSTFVVTSSGHWQAP-- 87
GRG7   NRALLLAGLAKGTSRLTGALKSDDTRVMSEALRLMGVQVDEPDDSTFVVTSSGHWQAP-- 87
GRG8   NRALLLAGLAKGTSRLTGALKSDDTRYMAEALRAMGVTIDEPDDTTFIVKGSGKLQPP-- 88
GRG9   NRALLLAGLAKGKSHLSGALKSDDTLYMAEALREMGVKVTEPDATTFVVEGTGVLQQP-- 84
GRG10  HRAIICAALSEEESTIENISYSKDIKATCIGMSKLGALIIEDAKDNSTLKIKKQKLVSKE 84
GRG12  NRALLAALAKGTSRLSGALKSDDTRHMSVALRQMGVTIDEPDDTTFVVTSQGSLQLP-- 113
GRG15  NRALLLAGLAKGKSRLTGALKSDDTLYMAEALREMGVKVTEPDATTFVVESSGGLHQP-- 84
GRG20  IRLIFLSLFTR--VYLHNLVLSEDVIDAIKSVRALGVKVKNNSEFIPPEKLEIKER---- 77

GRG21  HRYIIASSLAKGISKIENISYSDDIIATIEAMKKLGANIEK--KDN-YLLIDGSKTFDKE 84
GRG22  HRALIAASLCDGSTELWNVLDAEDVRATLRLCRMLGAEVDVDGEERLEATVSGFGDSP-- 83
GRG23  NRALLLAAAAKGTSVLVRPLVSADTSAFKTAIQALGANVS-ADGDNWVVEGLGQAPHL-- 95
GRG25  NRYLILAALASSPSTIHNTLISRDTELMLDALAAFGIGIERTTQP-DGSTTVAITPGKLA 119
GRG26  NRYLVLAALANGPSRLRAPLHSRDSALMVEALRRLGATITEVPGDGQYGPDLEVTPIDPA 105
GRG27  NRFLVLAALADGPSRLRAPLHSRDSALMIQALRQLGATVTEVPGDGDYGPDLEITPLDPS 102
GRG28  NRFLVLAALADGPSRLRAPLHSRDSVLMIQALRQLGATVTEVPGDGDYGPDLEITPMDPS 102
GRG29  TRYLLAAALAEGTSTIHYPAHSEDSDAMRRCISDLGAVLEEDDSK---IVIQGFGSHP-- 79
GRG30  TRYLLAAALAEGTSTIHYPAHSEDSDAMRRCIRDLGAVLEEDDSK---IVIQGFGSHP-- 79
GRG31  NRALIIQSLSKGQVEIANLSEAADTVTLNRVLQIASDPKPG------------------ 69
         *              :     : *              .
```

FIG. 1A

```
GRG1     ------FIDCGESGLSIRMFTPIVALSKEEVTIKGS-GSLVTRPMDFFDEILPHLGVKVK 135
GRG5     ----QQALFLGNAGTATRFLTAALANFEGDFVVDGD-EYMRKRPIGPLVDALQRMGVEVS 142
GRG6     ----QQALFLGNAGTATRFLTAALANFEGDFVVDGD-EYMRKRPIGPLVDALQRMGVEIS 142
GRG7     ----QQALFLGNAGTATRFLTAALANFEGDFVVDGD-EYMRKRPIGPLVDALQRMGVEVS 142
GRG8     ----AAPLFLGNAGTATRFLTAAAALVDGKVIVDGD-AHMRKRPIGPLVDALRSLGIDAS 143
GRG9     ----EKPLFLGNAGTATRFLTAAGALVLPVQAVIDGD-EHMRKRPILPLVQALRALGVEAD 139
GRG10    KVY----IDCSESGSTVRFLIPISLIEERNVVFDGQ-GKLSYRPLDSYFNIFDEKEIAYS 139
GRG12    ----AQPLFLGNAGTAMRFLTAAVATVQGTVVLDGD-EYMQKRPIGPLLATLGQNGIQVD 168
GRG15    ----EKPLFLGNAGTATRFLTAAAALVDGAVIIDGD-EHMRKRPIMPLVEALRSLGVEAE 139
GRG20    ------FIKLKGSATTLRMLIPILAAIGGEVTIDAD-ESLRRRPLNRIVQALSNYGISFS 130
GRG21    YLNNDSEIDCNESGSTLRFLFPLSIVKENKILFKGK-GKLFKRPLSPYFENFDKYQIKCS 143
GRG22    -RAPEDVVDCGNSGTTLRLGCGLAALVEGTTILTGD-DSLRSRPVGDLLAALRSLGVDAR 141
GRG23    ----DADIWCEDAGTVARFLPPFVAAGQGKFTVDGS-EQLRRRPLRPLVDGIRHLGARVS 150
GRG25    TG--PLSIDCGLAGTVMRFVPPLAAVAGASVAFDGD-EAARVRPMAPVLDALETLGARIE 176
GRG26    AAASETAIDCGLAGTVMRFVPPLAALRNGASVFDGD-PHARQRPMGTIIEALRTLGVDVS 164
GRG27    AAGSSTAIDCGLAGTVMRFVPPLAALRSGATVFDGD-PHARNRPMGTIIEALLALGVPVA 161
GRG28    ASGAETAIDCGLAGTVMRFVPPLAALRNGPTTFDGD-PHARKRPMGTIIEALLALGVPVA 161
GRG29    -RDVRELN-VGNAGAVLRFLMGVTALCPDVTFVNTYPDSLGKRPHDDLIDALGQLGVEVQ 137
GRG30    -HDVRELN-VGNAGAVLRFLMGVTALCPEVTFVNTYPDSLGKRPHDDLIDALGQLGVEVQ 137
GRG31    ----FNTIDIGPAGTAMRFLTAYLNLVKGNFILTGT-ERMQQRPIGILVDAMKEIGADIH 124
                    :.   *:            .       **         :

GRG1     SN--QGKLPLVIQGPLK----PADVTVDGSLSSQFLTGLLLAYAAADASDVAIKVTN-LK 188
GRG5     APSGCPPVAIKGKGG----LEAGRIEIDGNLSSQYVSALLMAGACGKGPVEVALTGSEIG 198
GRG6     APSGCPPVAIKGKGG----LQAGRIEIDGNLSSQYVSALLMAGACGKGSLEVALTGSEIG 198
GRG7     APSGCPPVAIKGKGG----LEAGRIEIDGNLSSQYVSALLMAGACGKGPVEVALTGSEIG 198
GRG8     AETGCPPVTINGTGR----FEASRVQIDGGLSSQYVSALLMMAAGGDRAVDVELLGEHIG 199
GRG9     APTGCPPVTVRGKMG---FPKGSVTIDANLSSQYVSALLMAAACGDKPVDIILKGEEIG 196
GRG10    HP-EGKVLPLQIKGRLK----AGMFNLPGNISSQFISGLMFSLPFLEGDSIINITTN-LE 193
GRG12    SPTGCPPVTVHGAGK----VQARRFEIDGGLSSQYVSALLMLAACGEAPIEVALTGKDIG 224
GRG15    APTGCPPVTVCGKGTG---FPKGSVTIDANLSSQYVSALLMAAACGDKPVDIILKGEEIG 196
GRG20    SYSLPLTITGKLSSN--------EIKISGDESSQYISGLIYALHILNGGS-IEILPP-IS 180
GRG21    SINENKIL---LDGELK----SGVYEIDGNISSQFITGLLFSLPLLNGNSKIIIKGK-LE 195
GRG22    GRVVRGEEYPPVVISGR--PLRERVAVYGDVSSQFVSALLFLGAGLGALR-VDVVGD-LR 197
GRG23    SEQLPLTIEASGLAG-------GEYEIEAHQSSQFASGLIMAAPYARQGLRVRIPNP--V 201
GRG25    YAG--TPGMLPFTMDASALQERHEVLIDASGSSQFISALLLVGQALPGGLKLRAAAGHIA 234
GRG26    AMDGKAPGSLPFKVSGTGSVRGGHLVIDASASSQFVSALLLVGARFEEGLHLEHVGKPVP 224
GRG27    AEGGRTPSALPFTVEGTGEVRGGHLVIDASASSQFVSALLLVGARFTEGLHLEHVGKPVP 221
GRG28    TEGGRTPSALPFSVDGTGEVRGGHLVIDASASSQFVSALLLVGARFTEGLHLEHVGKPVP 221
GRG29    HEQGR---LPITIKGGQ--AKGGHIRVSGSVSSQYLSALLFVTPLLAEDSTIEVLND-LK 191
GRG30    HEQGR---LPITIKGGQ--AKGGHIRVSGSVSSQYLSALLFVTPLLAEDSTIEVLND-LK 191
GRG31    YDKKVGYPPLKIEGGLFQ--EKDRVKIKGNISSQYISALLLIAPALKKGLTLEIEGE-LT 181
                        :  .   ***:  :.*:
```

FIG. 1B

```
GRG1    SRPYIDLTLDVMKRFGLKTPENRNYEEFYFKAGNVYDETKMQRYTVEGDWSGGAFLLVAG 248
GRG5    ARGYVDLTLAAMQAFGAEVQ-AIGETAWKVSA----TGYRATDFHIEPDASAATYLWAAQ 253
GRG6    ARGYVDLTLAAMQAFGAEVQ-AIGDAAWKVSA----TGYHATDFHIEPDASAATYLWAAQ 253
GRG7    ARGYLDLTLAAMRAFGAEVQ-AIGDAAWKVSA----TGYRATDFHIEPDASAATYLWAAQ 253
GRG8    ALGYIDLTVAAMRAFGAKVE-RVSPVAWRVEP----TGYHAADFVIEPDASAATYLWAAE 254
GRG9    AKGYIDLTTSAMEAFGAKVE-RVSNAIWRVHP----TGYTATDFHIEPDASAATYLWGAE 251
GRG10   SVGYVDMTIDMLKKFGIEIEN-KAYKSFFIKGN---QKCKGTKYKVEGDFSQAAFWLSAG 249
GRG12   ARGYVDLTLDCMRAFGAQVD-IVDDTTWRVAP----TGYTAHDYLIEPDASAATYLWAAE 279
GRG15   AKGYIDLTTSAMEAFGAKVE-RVSNAIWRVHP----TGYTATDFHIEPDASAATYLWGAE 251
GRG20   SKSYILLTIDLFKRFGSDVKFYGSKIHVNPNN------LVEFQGEVAGDYGLASFYALSA 234
GRG21   SSSYIDITLDCLNKFGINIIN-NSYKEFIIEGN---QTYKSGNYQVEADYSQVAFFLVAN 251
GRG22   SRPYVDMTVETLERFGVSVVR--EGSSFEVEG----RPRSPGKLRVENDWS-SAGYFVAL 250
GRG23   SQPYLTMTLRMMRDFGLETS-TDG-ATVSVPP----GRYTARRYEIEPDASTASYFAAAS 255
GRG25   SPDHIAMTVQTLRELGVEVAVGEDARSWSIAP----GQLSGFTITVEPDLSNAGPFLAAA 290
GRG26   SLDHINMTVAVLRGVGVQVDDSVPN-HWRVSP----GAIQAFDERIEQDLSNAGPFLAAA 279
GRG27   SLDHITMTVEVLRSVGVTVDDSVPN-HWRVSP----GKITAFDQRIEQDLSNAGPFLAAA 276
GRG28   SLDHINMTVSVLRGVGVKVDDSVPN-HWRVAP----GPIHAFDQRIEQDLSNAGPFLAAA 276
GRG29   SKVVIGQTLEVLEQAGIVIHASDDYMSFRVPGG---QAYKPQTYTVQGDYPGSAAVLAAA 248
GRG30   SKVVIGQTLEVLEQAGIVIHASDDYMSFRVPGG---QAYKPQTYTVQGDYPGSAAVLAAA 248
GRG31   SRPYVSMTDMLKSVGIQHEWKNN--AIKIAP----QAFEKQTIYVEPDWSAASYWYAIA 235
         :   :   *   :. *                              :   *

GRG1    AIAG---PITVRGLDI-ASTQADKAIVQALMSANAGI--AIDAKEIKLHPADLNAFEFDA 302
GRG5    ALTEG--DIDLGVASD-AFTQPDALASQIIASF----------------PNMPAVIDG 292
GRG6    ALTEG--NIDLGVASD-AFTQPDALASQIIDSF----------------PNMPAVIDG 292
GRG7    ALTEG--AIDLGVASN-AFTQPDALASQIIASF----------------PNMPAVIDG 292
GRG8    VLSGG--KIDLGTPAE-QFSQPDAKAYDLISKF----------------PHLPAVIDG 293
GRG9    LLTGG--AIDIGTPAD-KFTQPDAKAYEVMAQF----------------PHLPAEIDG 290
GRG10   ILNG---NINCKDLNI-SSLQGDKVILDILKKMGG----AIDEKSFSSKKSHTHGIVIDA 301
GRG12   VLTGG--RIDIGVAAQ-DFTQPDAKAQAVIAQG----------------PNMQATVVG 318
GRG15   LLTGG--AIDIGTPAD-KFTQPDAKAHEVMAQF----------------PHLPAEIDG 290
GRG20   LVSGG--GITITNLWEPKEYFGDHSIVKIFSEMGASSEYKD-GRWFVKAKDKYSPIKIDI 291
GRG21   SIGS---NIKINGLNV-NSLQGDKKIIDFIS--------EIDNWTKNEK------LILDG 293
GRG22   GAIGG--EMRIEGVDL-DSSHPDRRIVEITREMGAEVRRID-GGIVVRSTGRLEGVEVDL 306
GRG23   AVSGR--SFEFQGLGT-DSIQGDTSFFNVLGRLGAEVHWAPNSVTISGPERLNGDIEVDM 312
GRG25   LATNG--TVRVPFWPA-STTQVGGKWVQILSRMGAEISHG--EDGVLTVRGTGVIRGIDY 345
GRG26   LATKG--TVRIPNWPA-STTQVGDLWRNILATMGATVTL---DNGTLTVTGGSEILGADF 333
GRG27   LATHG--TVRIPNWPI-GTTQVGDLWRTILAAMGATVTL---DGGTLTVTGGNEIKGADF 330
GRG28   LATRG--TVRIPNWPT-QTTQVGDLWRSILVEMGATVTL---ENGTLTVKGGPEIKGADF 330
GRG29   AVTQS--DVKILRLME-QSKQGERAIVDVLRMMEVPLTHEN-DVVHVQGNGTLKAVEFDG 304
GRG30   AVTQS--DVKILRLME-QSKQGERAIVDVLRMMEVPLTHEN-DVVHVQGNGTLKAVEFDG 304
GRG31   ALADANASIVLPGLRK-NSLQGDIAIISIMEHFGVQSSFESDGLHLNKKVIGSDVSLFNF 294
```

FIG. 1C

```
GRG1   TDCPDLFPPLVALASYCKGETKIKGVSRLAHKESDRGLTLQDEFGKMG--VEIHLEGDLM 360
GRG5   SQMQDAIPTLAVLAAFNRQPVRFVGIANLRVKECDRISALSHGLCAIAPGLAVEEGDDLL 352
GRG6   SQMQDAIPTLAVLAAFNRQPVRFVGIANLRVKECDRISALCDGLCAIAPGLAVEEGDDLI 352
GRG7   SQMQDAIPTLAVLAAFNRQPVRFVGIANLRVKECDRISALSNGLCAIAPGLAVEEGDDLI 352
GRG8   SQMQDAIPTLAVLAAFNEMPVRFVGIENLRVKECDRIRALSSGLSRIVPNLGTEEGDDLI 353
GRG9   SQMQDAIPTIAVIAAFNETPVRFVGIANLRVKECDRIRAVSLGLNEIREGLAHEEGDDLI 350
GRG10  SQCPDLVPILSVVAALSEGTTKIVNAARLRIKESDRLKAMATELNKLG--AEVVELEDGL 359
GRG12  SQMQDAIPTLAVLAAFNNTPVRFTELANLRVKECDRVQALHDGLNEIRPGLATIEGDDLL 378
GRG15  SQMQDAIPTIAVLAAFNETPVRFVGIANLRVKECDRIRAVSLGLNEIRDGLAHEEGDDLI 350
GRG20  DDAPDLAMTIAGLSAIAEGTSEIIGIERLRIKESDRIESIRKILGLYG--VGSEVKYNSI 349
GRG21  SETPDIIPILSLKACISKKEIEIVNIARLRIKESDRLSATVQELSKLG--FDLIEKEDSI 351
GRG22  SDSPDLVPTVAAMCFAEGVTRIENVGHLRYKEVDRLRALAAELPKFG--VEVREGKDWL 364
GRG23  GEISDTFMTLAAIAPLADGPITITNIGHARLKESDRISAMETNLRTLG--VQTDVGHDWM 370
GRG25  ADASELAPTLAALCTLADSPSKLTGIGHLRGHETDRLAALETELAKVG--ATVTSTDDAL 403
GRG26  DETSELAPTVAALCALATSPSRLTGIAHLRGHETDRLAALVAEINRLG--GDAEETSDGL 391
GRG27  DETSELAPTVAALCALATGPSRLTGIAHLRGHETDRLAALVAEINRLG--GDAEETADGL 388
GRG28  DETSELAPTVAALCALATGPSRLTGIAHLRGHETDRLAALAAEINRLG--GDAEETADGL 388
GRG29  DAATDAVLAMVAAAVFAEGTSRFYNVENLRYKECDRITDYLNELRKAG--ANVEERQAEI 362
GRG30  DAATDAVLAMVAAAVFAEGTSRFYNVENLRYKECDRITDYLNELRKAG--ANVEERQAEI 362
GRG31  KECPDLAQTVVVVAAALKRDVSFTGLETLKIKETDRIAALQKEIAKFG--AELIEDGDTY 352
            :    :   .      :       :* **          :

GRG1   RVIGGKGVKGAE------VSSRHDHRIAMACAVAALKAVGETTIEHAEAVNKSYPDFYSD 414
GRG5   VHANPALAGTTVD---ALIDTHSDHRIAMCFALAGLKIAG-IRILDPDCVGKTYPGYWDA 408
GRG6   VHANPALAGTTVN---ALIDTHSDHRIAMCFALAGLKIKG-IHIQDPDCVAKTYPGYWDA 408
GRG7   VTANPTLAGTTVD---ALIDTHSDHRIAMCFALAGLKIAG-IRILDPDCVAKTYPGYWDA 408
GRG8   IASDPSLAGKILT---AEIDSFADHRIAMSFALAGLKIGG-ITILDPDCVAKTFPSYWNV 409
GRG9   VHADPSLAGQTVD---ASIDTFADHRIAMSFALAALKIGG-IAIQNPACVAKTYPGYWKA 406
GRG10  LIEGKEKLKGGE------VESWNDHRIAMALGIAALRCEESVTINGSECVSKSYPQFWSD 413
GRG12  VASDPALAGTACT---ALIDTHADHRIAMCFALAGLKVSG-IRIQDPDCVAKTYPDYWKA 434
GRG15  VHSDPSLAGQTVN---ASIDTFADHRIAMSFALAALKIGG-IAIQNPACVGKTYPGYWKA 406
GRG20  LIFGINKGMLNSP----VTDCLNDHRVAMMSSALALVNGG--VITSAECVGKSNPNYWQD 403
GRG21  LINSRKNFNEISNNSPISLSSHSDHRIAMTVAIASTCYEGEIILDNLDCVKKSYPNFWEV 411
GRG22  EIVG----GEPVG---ARVDSRGDHRMAMALAVVGAFARGKTVVERADAVSISYPRFWED 417
GRG23  RIYPSTPHG-------GRVNCHRDHRIAMAFSILGLRVDG-ITLDDPQCVGKTFPGFFDY 422
GRG25  EIIPGTLQA-------ADLDSYEDHRMATAGALLGLAIEG-VRVENIATTAKTMPDFPQL 455
GRG26  VIRPAALHS-------GVVHSYADHRMATAGAILGLAVEG-VRVEDIATTSKTMPEFPQI 443
GRG27  LIRPATLHG-------GVIHSYADHRMATAGAILGLAVDG-VQVEDIATTSKTMPEFPEM 440
GRG28  IIRPATLHP-------GVVHSYADHRMATAGAILGLAVEG-VQVEDIATTSKTVPEFPQM 440
GRG29  IVHGR-PEGVEGG---VEINAHYDHRVIMALTVVGLRSKEPLRIRDAHHVAKSYPQYFDH 418
GRG30  IVHGR-PEGVEGG---VEINAHYDHRVIMALTVVGLRSKEPLRIRDAHHVAKSYPQYFDH 418
GRG31  HLKTAQVYQPEE----VTFDTYEDHRMAMAFAPLALVFDQ-IKIAEPQVVEKSYPDFWNH 407
                    ***:             .      :      .  :*:.
```

FIG. 1D

```
GRG1      LKQLGGVVSLNHQFNFS----  431
GRG5      LASLGVRVQR-----------  418
GRG6      LASLGVSVQR-----------  418
GRG7      LASLGVSVQR-----------  418
GRG8      LSSLGVAYED-----------  419
GRG9      LASLGVDYTEKESAAEPQH--  425
GRG10     LKQLGGDVHEWSLGE------  428
GRG12     LASLGVHLSY-----------  444
GRG15     LASLGVEYSEKETAAEPQH--  425
GRG20     LLSLNAKISIE----------  414
GRG21     FLSLGGKIYEY-LG-------  424
GRG22     LASVGVPVHSV----------  428
GRG23     LGRLFPEKALTLPG-------  436
GRG25     WTDMAATAKGQG---------  467
GRG26     WTSMLSAGPAAAAAGSTETSN  464
GRG27     WARMLDSAG------TNEAGN  455
GRG28     WEAMLQQGTGEDETVTSEASN  461
GRG29     LQALGASVQWVKE--------  431
GRG30     LQALGASVQWVKE--------  431
GRG31     LQAQAFVIE------------  416
```

FIG. 1E

EPSP SYNTHASE GENES CONFERRING HERBICIDE RESISTANCE

CROSS REFERENCE TO RELATED APPLICATION

This application claims the benefit of U.S. Provisional Application Ser. No. 60/812,360, filed Jun. 9, 2006, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "325057_SequenceListing.txt", created on Jun. 5, 2007, and having a size of 136 kilobytes and is filed concurrently with the specification. The sequence listing contained in this ASCII formatted document is part of the specification and is herein incorporated by reference in its entirety.

FIELD OF THE INVENTION

This invention provides novel genes encoding 5-enolpyruvylshikimate-3-phosphate (EPSP) synthase that provide herbicide resistance. These genes are useful in plant biology, crop breeding, and plant cell culture.

BACKGROUND OF THE INVENTION

N-phosphonomethylglycine, commonly referred to as glyphosate, is an important agronomic chemical. Glyphosate inhibits the enzyme that converts phosphoenolpyruvic acid (PEP) and 3-phoshoshikimic acid to 5-enolpyruvyl-3-phosphoshikimic acid. Inhibition of this enzyme (5-enolpyruvylshikimate-3-phosphate synthase; referred to herein as "EPSP synthase") kills plant cells by shutting down the shikimate pathway, thereby inhibiting aromatic acid biosynthesis.

Since glyphosate-class herbicides inhibit aromatic amino acid biosynthesis, they not only kill plant cells, but are also toxic to bacterial cells. Glyphosate inhibits many bacterial EPSP synthases, and thus is toxic to these bacteria. However, certain bacterial EPSP synthases have a high tolerance to glyphosate.

Plant cells resistant to glyphosate toxicity can be produced by transforming plant cells to express glyphosate-resistant bacterial EPSP synthases. Notably, the bacterial gene from *Agrobacterium tumefaciens* strain CP4 has been used to confer herbicide resistance on plant cells following expression in plants. A mutated EPSP synthase from *Salmonella typhimurium* strain CT7 confers glyphosate resistance in bacterial cells, and confers glyphosate resistance on plant cells (U.S. Pat. Nos. 4,535,060; 4,769,061; and 5,094,945).

U.S. Pat. No. 6,040,497 reports mutant maize EPSP synthase enzymes having substitutions of threonine to isoleucine at position 102 and proline to serine at position 106 (the "TIPS" mutation). Such alterations confer glyphosate resistance upon the maize enzyme. A mutated EPSP synthase from *Salmonella typhimurium* strain CT7 confers glyphosate resistance in bacterial cells, and is reported to confer glyphosate resistance upon plant cells (U.S. Pat. Nos. 4,535,060; 4,769,061; and 5,094,945). He et al. ((2001) *Biochim et Biophysica Acta* 1568:1-6) have developed EPSP synthases with increased glyphosate tolerance by mutagenesis and recombination between the *E. coli* and *Salmonella typhimurium* EPSP synthase genes, and suggest that mutations at position 42 (T42M) and position 230 (Q230K) are likely responsible for the observed resistance.

Subsequent work (He et al. (2003) *Biosci. Biotech. Biochem.* 67:1405-1409) shows that the T42M mutation (threonine to methionine) is sufficient to improve tolerance of both the *E. coli* and *Salmonella typhimurium* enzymes. These enzymes contain amino acid substitutions in their active sites that prevent the binding of glyphosate without affecting binding by PEP or S3P. Mutations that occur in the hinge region between the two globular domains of EPSP synthase have been shown to alter the binding affinity of glyphosate but not PEP (He et al., 2003, supra). Therefore, such enzymes have high catalytic activity, even in the presence of glyphosate.

Due to the many advantages herbicide resistance plants provide, methods for identifying herbicide resistance genes with glyphosate resistance activity are desirable.

SUMMARY OF INVENTION

Compositions and methods for conferring herbicide resistance or tolerance to bacteria, plants, plant cells, tissues and seeds are provided. Compositions include nucleic acid molecules encoding herbicide resistance or tolerance polypeptides, vectors comprising those nucleic acid molecules, and host cells comprising the vectors. Compositions also include antibodies to the herbicide resistance or tolerance polypeptides. As noted the nucleotide sequences of the invention can be used in DNA constructs or expression cassettes for transformation and expression in organisms, including microorganisms and plants. Compositions also comprise transformed bacteria, plants, plant cells, tissues, and seeds. In addition, methods are provided for producing the polypeptides encoded by the synthetic nucleotides of the invention.

In particular, isolated nucleic acid molecules and variants thereof encoding herbicide resistance- or tolerance polypeptides are provided. Additionally, amino acid sequences and variants thereof encoded by the polynucleotides that confer herbicide resistance or tolerance are encompassed. In particular, the present invention provides for isolated nucleic acid molecules comprising the nucleotide sequence set forth in SEQ ID NO: 1, 3, 5, 7, 9, 11, 13, 28, 29, 30, 31, 32, 33, or 34, a nucleotide sequence encoding the amino acid sequence shown in SEQ ID NO:2, 4, 6, 8, 10, 12, or 14, the herbicide resistance nucleotide sequence deposited in a bacterial host as Accession Nos. NRRL B-30911, NRRL B-30912, NRRL B-30913, NRRL B-30914 N, NRRL B-30915, NRRL B-30916 N, or NRRL B-30917 N, as well as variants and fragments thereof. Nucleotide sequences that are complementary to a nucleotide sequence of the invention, or that hybridize to a sequence of the invention are also encompassed.

DESCRIPTION OF FIGURES

FIGS. 1A-1E show an alignment of the amino acid sequence of GRG25 (SEQ ID NO:2), GRG26 (SEQ ID NO:4), GRG27 (SEQ ID NO:6), GRG28 (SEQ ID NO:8), GRG29 (SEQ ID NO:10), GRG30 (SEQ ID NO:12), and GRG31 (SEQ ID NO:14) with other glyphosate tolerant EPSP synthase genes, including GRG1 (SEQ ID NO:15), GRG5 (SEQ ID NO:16), GRG6 (SEQ ID NO:17), GRG7 (SEQ ID NO:18), GRG8 (SEQ ID NO:19), GRG9 (SEQ ID NO:20), GRG10 (SEQ ID NO:21), GRG12 (SEQ ID NO:22), GRG15 (SEQ ID NO:23), GRG20 (SEQ ID NO:24), GRG21 (SEQ ID NO:25), GRG22 (SEQ ID NO:26), and GRG23 (SEQ ID NO:27). The symbol [*] indicates that the residues are identical in all sequences in the alignment; the [:] symbol indicates conservative substitutions; the [.] symbol indicates semi-conservative substitutions.

DETAILED DESCRIPTION

The present invention is drawn to compositions and methods for regulating herbicide resistance in organisms, particularly in plants or plant cells. The methods involve transforming organisms with a nucleotide sequence encoding a glyphosate resistance gene of the invention. In particular, a nucleotide sequence of the invention is useful for preparing plants that show increased tolerance to the herbicide glyphosate. Thus, transformed bacteria, plants, plant cells, plant tissues and seeds are provided. Compositions include nucleic acids and proteins relating to herbicide tolerance in microorganisms and plants as well as transformed bacteria, plants, plant tissues and seeds. More particularly, nucleotide sequences of the glyphosate resistance genes (grg25, grg26, grg27, grg28, grg29, grg30, grg31, syngrg25, syngrg26, syngrg27, syngrg28, syngrg29, syngrg30, and syngrg31) and the amino acid sequences of the proteins encoded thereby are disclosed. The sequences find use in the construction of expression vectors for subsequent transformation into plants of interest, as probes for the isolation of other glyphosate resistance genes, as selectable markers, and the like. Thus, by "glyphosate resistance" or "glyphosate tolerance" gene of the invention is intended the nucleotide sequence set forth in SED ID NO: 1, 3, 5, 7, 9, 11, or 13 and fragments and variants thereof (e.g. SEQ ID NO:28-34) that encode a glyphosate resistance or tolerance polypeptide. Likewise, a "glyphosate resistance" or "glyphosate tolerance" polypeptide of the invention is a polypeptide having the amino acid sequence set forth in SEQ ID NO:2, 4, 6, 8, 10, 12, or 14, and fragments and variants thereof, that confer glyphosate resistance or tolerance to a host cell.

Plasmids containing the herbicide resistance nucleotide sequences of the invention were deposited in the permanent collection of the Agricultural Research Service Culture Collection, Northern Regional Research Laboratory (NRRL), 1815 North University Street, Peoria, Ill. 61604, United States of America, on Apr. 19, 2006, and assigned Accession Nos. N NRRL B-30911 (for grg25), NRRL B-30912 (for grg26), NRRL B-30913 (for grg27), NRRL B-30914 N (for grg28), NRRL B-30915 (for grg29), NRRL B-30916 N (for grg30), and NRRL B-30917 (for grg31). This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 U.S.C. §112.

By "glyphosate" is intended any herbicidal form of N-phosphonomethylglycine (including any salt thereof) and other forms that result in the production of the glyphosate anion in planta. An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. A "glyphosate resistance protein" includes a protein that confers upon a cell the ability to tolerate a higher concentration of glyphosate than cells that do not express the protein, or to tolerate a certain concentration of glyphosate for a longer period of time than cells that do not express the protein. By "tolerate" or "tolerance" is intended either to survive, or to carry out essential cellular functions such as protein synthesis and respiration in a manner that is not readily discernable from untreated cells.

Isolated Nucleic Acid Molecules, and Variants and Fragments Thereof

One aspect of the invention pertains to isolated or recombinant nucleic acid molecules comprising nucleotide sequences encoding herbicide resistance proteins and polypeptides or biologically active portions thereof, as well as nucleic acid molecules sufficient for use as hybridization probes to identify herbicide resistance-encoding nucleic acids. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecules can be single-stranded or double-stranded, but preferably are double-stranded DNA.

Nucleotide sequences encoding the proteins of the present invention include the sequences set forth in SEQ ID NOS:1, 3, 5, 7, 9, 11, 13, 28, 29, 30, 31, 32, 33, and 34, the herbicide resistance nucleotide sequence deposited in a bacterial host as Accession Nos. NRRL B-30911, NRRL B-30912, NRRL B-30913, NRRL B-30914 N, NRRL B-30915, NRRL B-30916 N, and NRRL B-30917 N, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the herbicide resistance proteins encoded by these nucleotide sequences are set forth in SEQ ID NOS:2, 4, 6, 8, 10, 12, and 14. The invention also encompasses nucleic acid molecules comprising nucleotide sequences encoding partial-length herbicide resistance proteins, and complements thereof.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated glyphosate resistance-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. An herbicide resistance protein that is substantially free of cellular material includes preparations of protein having less than about 30%, 20%, 10%, or 5% (by dry weight) of non-herbicide resistance protein (also referred to herein as a "contaminating protein").

Nucleic acid molecules that are fragments of these herbicide resistance-encoding nucleotide sequences are also encompassed by the present invention. By "fragment" is intended a portion of a nucleotide sequence encoding an herbicide resistance protein. A fragment of a nucleotide sequence may encode a biologically active portion of an herbicide resistance protein, or it may be a fragment that can be used as a hybridization probe or PCR primer using methods disclosed below. Nucleic acid molecules that are fragments of an herbicide resistance nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400 contiguous nucleotides, or up to the number of nucleotides present in a full-length herbicide resistance-encoding nucleotide sequence disclosed herein (for example, 1404 nucleotides for SEQ ID NO:1; 1395 nucleotides for SEQ ID NO:3, 1368 nucleotides for SEQ ID NO:5, etc) depending upon the intended use. By "contiguous" nucleotides is intended nucleotide residues that are immediately adjacent to one another.

Fragments of the nucleotide sequences of the present invention generally will encode protein fragments that retain the biological activity of the full-length glyphosate resistance protein; i.e., herbicide-resistance activity. By "retains herbicide resistance activity" is intended that the fragment will have at least about 30%, at least about 50%, at least about 70%, or at least about 80% of the herbicide resistance activity of the full-length glyphosate resistance protein disclosed herein as SEQ ID NOS:2, 4, 6, 8, 10, 12, or 14. Methods for measuring herbicide resistance activity are well known in the art. See, for example, U.S. Pat. Nos. 4,535,060, and 5,188,642, each of which are herein incorporated by reference in their entirety.

A fragment of an herbicide resistance-encoding nucleotide sequence that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length herbicide resistance protein of the invention (for example, 467 amino acids for SEQ ID NO:2; 464 for SEQ ID NO:4, 455 amino acids for SEQ ID NO:6, etc).

Preferred herbicide resistance proteins of the present invention are encoded by a nucleotide sequence sufficiently identical to the nucleotide sequence of SEQ ID NOS:1, 3, 5, 7, 9, 11, 13, 28, 29, 30, 31, 32, 33, or 34. The term "sufficiently identical" is intended an amino acid or nucleotide sequence that has at least about 60% or 65% sequence identity, about 70% or 75% sequence identity, about 80% or 85% sequence identity, or about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to glyphosate-resistant nucleic acid molecules of the invention. BLAST protein searches can be performed with the BLASTX program, score=50, wordlength=3, to obtain amino acid sequences homologous to herbicide resistance protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See www.ncbi.nlm.nih.gov. Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENEDOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) supra, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the herbicide resistance-encoding nucleotide sequences include those sequences that encode an herbicide resistance protein disclosed herein but that differ conservatively because of the degeneracy of the genetic code, as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the herbicide resistance proteins disclosed in the present invention as discussed below. Variant proteins encompassed by the present invention are biologically active, that is they retain the desired biological activity of the native protein, that is, herbicide resistance activity. By "retains herbicide resistance activity" is intended that the variant will have at least about 30%, at least about 50%, at least about 70%, or at least about 80% of the herbicide resistance activity of the native protein. Methods for measuring herbicide resistance activity are well known in the art. See, for example, U.S. Pat. Nos. 4,535,060, and 5,188,642, each of which are herein incorporated by reference in their entirety.

The skilled artisan will further appreciate that changes can be introduced by mutation into the nucleotide sequences of the invention thereby leading to changes in the amino acid sequence of the encoded herbicide resistance protein, without altering the biological activity of the protein. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more predicted, preferably nonessential amino acid residues. A "nonessential" amino acid residue is a residue that can be altered from the wild-type sequence of an herbicide resistance protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Amino acid substitutions may be made in nonconserved regions that retain function. In general, such substitutions would not be made for conserved amino acid residues, or for amino acid residues residing within a conserved motif, where such residues are essential for protein activity. However, one of skill in the art would understand that functional variants may have minor conserved or nonconserved alterations in the conserved residues. Examples of residues that are conserved and that may be essential for protein activity include, for example, residues that are identical between all proteins contained in the alignment of FIG. 1. Examples of residues that are conserved but that may allow conservative amino acid substitutions and still retain activity include, for example, residues that have only conservative substitutions between all proteins contained in the alignment of FIG. 1.

Lys-22, Arg-124, Asp-313, Arg-344, Arg-386, and Lys-411, are conserved residues of the EPSP synthase from *E. coli* (Schönbrunn et al. (2001) *Proc. Natl. Acad. Sci. USA* 98: 1376-1380). Conserved residues important for EPSP synthase activity also include Arg-100, Asp-242, and Asp-384 (Selvapandiyan et al. (1995) *FEBS Letters* 374:253-256). Arg-27 binds to S3P (Shuttleworth et al. (1999) *Biochemistry* 38:296-302).

Alternatively, variant nucleotide sequences can be made by introducing mutations randomly along all or part of the coding sequence, such as by saturation mutagenesis, and the resultant mutants can be screened for ability to confer herbicide resistance activity to identify mutants that retain activity. Following mutagenesis, the encoded protein can be expressed recombinantly, and the activity of the protein can be determined using standard assay techniques.

Using methods such as PCR, hybridization, and the like, corresponding herbicide resistance sequences can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the herbicide resistance nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known herbicide resistance-encoding nucleotide sequences disclosed herein. Degenerate primers designed on the basis of conserved nucleotides or amino acid residues in the nucleotide sequences or encoded amino acid sequences can additionally be used. The probe typically comprises a region of nucleotide sequence that hybridizes under stringent conditions to at least about 12, preferably about 25, at least about 50, 75, 100, 125, 150, 175, 200, 250, 300, 350, 400, 500, 600, 700, 800, 900, 1000, 1200, 1300 consecutive nucleotides of an herbicide resistance-encoding nucleotide sequence of the invention or a fragment or variant thereof. Methods for the preparation of probes for hybridization are generally known in the art and are disclosed in Sambrook and Russell, 2001, supra and Sambrook et al. (1989) *Molecular Cloning: A Laboratory Manual* (2d ed., Cold Spring Harbor Laboratory Press, Cold Spring Harbor, N.Y.), both of which are herein incorporated by reference.

For example, an entire herbicide resistance sequence disclosed herein, or one or more portions thereof, may be used as a probe capable of specifically hybridizing to corresponding herbicide resistance sequences and messenger RNAs. To achieve specific hybridization under a variety of conditions, such probes include sequences that are unique and are at least about 10 nucleotides in length, or at least about 20 nucleotides in length. Such probes may be used to amplify corresponding herbicide resistance sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Herbicide resistance proteins are also encompassed within the present invention. By "herbicide resistance protein" is intended a protein having the amino acid sequence set forth in SEQ ID NOS:2, 4, 6, 8, 10, 12, or 14. Fragments, biologically active portions, and variants thereof are also provided, and may be used to practice the methods of the present invention.

"Fragments" or "biologically active portions" include polypeptide fragments comprising a portion of an amino acid sequence encoding an herbicide resistance protein as set forth in SEQ ID NOS:2, 4, 6, 8, 10, 12, or 14, and that retains herbicide resistance activity. A biologically active portion of an herbicide resistance protein can be a polypeptide that is, for example, 10, 25, 50, 100 or more amino acids in length. Such biologically active portions can be prepared by recombinant techniques and evaluated for herbicide resistance activity. Methods for measuring herbicide resistance activity are well known in the art. See, for example, U.S. Pat. Nos. 4,535,060, and 5,188,642, each of which are herein incorporated by reference in their entirety. As used here, a fragment comprises at least 8 contiguous amino acids of SEQ ID NOS: 2, 4, 6, 8, 10, 12, or 14. The invention encompasses other fragments, however, such as any fragment in the protein greater than about 10, 20, 30, 50, 100, 150, 200, 250, 300, 350, or 400 amino acids.

By "variants" is intended proteins or polypeptides having an amino acid sequence that is at least about 60%, 65%, about 70%, 75%, 80%, 85%, or 90%, 91%, 92%, 93%, 94%, 95%, 96%, 97%, 98% or 99% identical to the amino acid sequence of SEQ ID NOS:2, 4, 6, 8, 10, 12, or 14. Variants also include polypeptides encoded by a nucleic acid molecule that hybridizes to the nucleic acid molecule of SEQ ID NOS:1, 3, 5, 7, 9, 11, 13, 28, 29, 30, 31, 32, 33, or 34, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining herbicide resistance activity. Methods for measuring herbicide resistance activity are well known in the art. See, for example, U.S. Pat. Nos. 4,535,060, and 5,188,642, each of which are herein incorporated by reference in their entirety.

Bacterial genes, such as the grg25, grg26, grg27, grg28, grg29, grg30, grg31, syngrg25, syngrg26, syngrg27, syngrg28, syngrg29, syngrg31, and syngrg31 genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may lead to generation of variants of grg25, grg26, grg27, grg28, grg29, grg30, grg31, syngrg25, syngrg26, syngrg27, syngrg28, syngrg29, syngrg30, and syngrg31 that confer herbicide resistance. These herbicide resistance proteins are encompassed in the present invention and may be used in the methods of the present invention.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of grg25, grg26, grg27, grg28, grg29, grg30, grg31, syngrg25, syngrg26, syngrg27, syngrg28, syngrg29, syngrg30, and syngrg31 may be altered by various methods, and that these alterations may result in DNA sequences encoding proteins with amino acid sequences different than that encoded by grg25, grg26, grg27, grg28, grg29, grg30, or grg31, respectively. This protein may be altered in various ways including amino acid substitutions, deletions, truncations, and insertions of one or more amino acids of SEQ ID NO:1, 3, 5, 7, 9, 11, 13, 28, 29, 30, 31, 32, 33, or 34, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100 or more amino acid substitutions, deletions or insertions.

Methods for such manipulations are generally known in the art. For example, amino acid sequence variants of the GRG proteins disclosed herein can be prepared by mutations in the DNA. This may also be accomplished by one of several forms of mutagenesis and/or in directed evolution. In some aspects, the changes encoded in the amino acid sequence will not substantially affect function of the protein. Such variants will possess the desired herbicide resistance activity. However, it is understood that the ability of GRG25, GRG26, GRG27, GRG28, GRG29, GRG30, or GRG31 to confer herbicide resistance may be improved by one use of such techniques upon the compositions of this invention. For example, one may express GRG25, GRG26, GRG27, GRG28, GRG29, GRG30, or GRG31 in host cells that exhibit high rates of base misincorporation during DNA replication, such as XL-1 Red (Stratagene, La Jolla, Calif.). After propagation in such strains, one can isolate the DNA of the invention (for example by preparing plasmid DNA, or by amplifying by PCR and cloning the resulting PCR fragment into a vector), culture the grg mutations in a non-mutagenic strain, and identify mutated genes with improved resistance to an herbicide such as glyphosate, for example by growing cells in increasing concentrations of glyphosate and testing for clones that confer ability to tolerate increased concentrations of glyphosate.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest, (2) introduce a binding domain, enzymatic activity, or epitope to facilitate either protein purification, protein detection, or other experimental uses known in the art, or, (3) target secretion or translation of a protein to a subcellular organelle, such as the periplasmic space of gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different herbicide resistance protein coding regions can be used to create a new herbicide resistance protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the herbicide resistance gene of the invention and other known herbicide resistance genes to obtain a new gene coding for a protein with an improved property of interest, such as an increased glyphosate resistance activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Temperature Spectrum

Several studies of glyphosate metabolism in plants have been carried out, and reveal that glyphosate is not metabolized by plants or is metabolized very slowly. Glyphosate penetrates the cuticle rapidly, and is translocated throughout plants over a considerable period of time (reviewed in Kearney and Kaufman, Eds (1988) *Herbicides; Chemistry, Degradation & Mode of Action Marcel Dekker, Inc., New York*, 3:1-70 and Grossbard and Atkinson, Eds. (1985) *The Herbicide Glyphosate* Butterworths, London, p. 25-34). Thus, it is likely that glyphosate tolerance is necessary over a sustained period of time following glyphosate exposure in agronomically-important plants. Where temperatures frequently exceed 30° C. during the growing season, it would be advantageous to employ a glyphosate-tolerance EPSP synthase that maintains activity at elevated temperatures.

In one embodiment of the present invention, the EPSP synthase exhibits thermal stability at a temperature that is higher or lower than ambient environmental temperature. By "thermal stability" is intended that the enzyme is active at a higher or lower temperature than ambient environmental temperature for a longer period of time than an EPSP synthase that is not thermal stable at that temperature. For example, a thermal stable EPSP synthase has enzymatic activity for greater than about 1 hour, greater than about 2 hours, about 3, about 4, about 5, about 6, about 7, about 8, about 9, about 10, about 11, about 12, about 13, about 14, about 15, about 20, about 25 hours, or longer, at a temperature that is higher or lower than ambient environmental temperature. For the purposes of the present invention, "ambient" environmental temperature is about 30° C. In some embodiments, a higher than ambient temperature is a temperature at or above about 32° C., about 34° C., about 37° C., about 40° C., about 45° C., about 50° C., about 55° C., about 60° C., about 65° C., or higher. A lower than ambient temperature is a temperature at or below about 28° C., below about 27° C., about 26° C., about 25° C., about 23° C., about 20° C., about 18° C., about 15° C., about 10° C., at or below about 5° C., or around 0° C. Methods to assay for EPSP synthase activity are discussed in further details elsewhere herein. For the purposes of the present invention, a thermal stable EPSP synthase is considered active when it functions at about 90% to 100%, about 80% to about 90%, about 70% to about 80%, about 60% to about 70% or about 50% to about 60% of the maximum activity level observed at the optimum temperature for that enzyme.

In another embodiment, the temperature optimum for an EPSP synthase enzyme of the invention is higher or lower than the temperature optimum of a wild-type glyphosate tolerance EPSP synthase enzyme. For the purposes of the present invention, a wild type glyphosate tolerance EPSP synthase enzyme is one that has maximal activity at ambient environmental temperature (e.g., the glyphosate tolerance EPSP synthase enzyme described at GRG23 in U.S. patent application Ser. No. 11/605,824, filed Nov. 29, 2006, herein incorporated by reference in its entirety). By "optimum" is intended the maximal activity observed for an EPSP synthase enzyme, for example, when measured across multiple temperature ranges. In non-limiting examples, the EPSP synthase employed in the methods of the invention can have optimal activity from about 0° C. to about 10° C., about 10° C. to about 20° C., about 20° C. to about 30° C., about 30° C., to about 40° C., about 40° C. to about 50° C., about 50° C. to about 60° C., about 60° C., to about 70° C., or about 70° C. to about 80° C.

Thus, provided herein are methods and compositions for increasing glyphosate tolerance at temperatures higher or lower than ambient environmental temperatures. In one embodiment, the methods comprise introducing into a plant a nucleotide sequence encoding a glyphosate tolerance EPSP synthase enzyme that is thermal stable at a temperature that is higher or lower than ambient temperature, and growing the plant at a temperature that is higher or lower, respectively, than ambient environmental temperature. In specific embodiments, the growing temperature is higher or lower than ambient temperature for an average of at least about 2 hours per day, at least about 3 hours per day, at least about 4 hours per day, at least about 5, about 6, about 7, about 8, about 9, about 10, about 11, about 12, about 14, about 16, about 18, about 20, at least about 22 hours per day, or up to about 24 hours a day during the growing season of the plant.

In another embodiment, the method comprises introducing into a plant a nucleotide sequence encoding a glyphosate tolerant EPSP synthase enzyme other than SEQ ID NO:35, 36, or 37 that has a temperature optimum higher than ambient environmental temperature, contacting the plant with an herbicidally-effective concentration of glyphosate, and growing said plant at temperature that exceeds ambient environmental temperature for at least 1 hour, at least about 2 hours, at least about 3, at least about 4, or more hours per day for at least 2, 3, 4, 5, 6, 7, 8, 9, 10, 11, 12, 13, 14, 15, 16, 17, 18, 19, 20 or more days after glyphosate is applied to the plant, wherein the days in which the temperature exceeds ambient environmental temperature occur during the growing season of the plant. In another embodiment, the method comprises introducing into a plant a nucleotide sequence encoding a glyphosate tolerant EPSP synthase enzyme other than SEQ ID NO:38 that has a temperature optimum lower than ambient environmental temperature, contacting the plant with an herbicidally-effective concentration of glyphosate, and growing said plant at a temperature that is below ambient environmental temperature for at least about 1 hour, at least about 2 hours, at least about 3, at least about 4, or more hours per day for at least 2, 3, 4, 5, 6, 7, 8, 9, 10, 11, 12, 13, 14, 15, 16, 17, 18, 19, 20 or more days after glyphosate is applied to the plant, wherein the days in which the temperature exceeds ambient environmental temperature occur during the growing season of the plant.

In yet another embodiment, the method comprises introducing into a plant a nucleotide sequence encoding a glyphosate tolerant EPSP synthase that is thermal stable at temperatures higher than ambient environmental temperature, contacting the plant with an herbicidally-effective concentration of glyphosate, and growing the plant at a temperature that is higher than ambient environmental temperature, wherein the temperature is higher than ambient environmental temperature for at least about 1 hour, at least about 2 hours, at least about 3, at least about 4, or more hours per day for at least 2, 3, 4, 5, 6, 7, 8, 9, 10, 11, 12, 13, 14, 15, 16, 17, 18, 19, 20 or more days after glyphosate is applied to the plant, wherein the days in which the temperature exceeds ambient environmental temperature occur during the growing season of the plant. In one non-limiting example, the thermal stable EPSP synthase enzyme is set forth in SEQ ID NO:14. Alternatively, the method comprises introducing into a plant a nucleotide sequence encoding a glyphosate tolerant EPSP synthase enzyme that is thermal stable at temperatures lower than ambient environmental temperature, contacting the plant with an herbicidally-effective concentration of glyphosate, and growing the plant at a temperature that is lower than ambient environmental temperature for at least about 1 hour, at least about 2 hours, at least about 3, at least about 4, or more hours per day for at least 2, 3, 4, 5, 6, 7, 8, 9, 10, 11, 12, 13, 14, 15, 16, 17, 18, 19, 20 or more days after glyphosate is applied to the plant, wherein the days in which the temperature exceeds ambient environmental temperature occur during the growing season of the plant.

In various embodiments, the glyphosate tolerance EPSP synthase enzyme that is thermal stable at temperatures higher or lower than ambient environmental temperatures, or has a thermal optimum at a temperature lower or higher than ambient environmental temperature, is not a plant-derived EPSP synthase. By "plant-derived" is intended the native plant EPSP synthase sequence, or a sequence that is at least about 80%, at least about 85%, at least about 90%, about 91%, about 92%, about 93%, about 94%, about 95%, about 96%, about 97%, about 98%, or at least about 99% identical to the native plant sequence. See, for example, the plant-derived glyphosate tolerance EPSP synthase sequences described in U.S. Patent Application Publication Nos. 20060143727, 20030049814, 20030079246, 20030200560, 2004148650, and 20050223436; U.S. Pat. Nos. 5,188,642, 6,040,497, 7,214,535, 7,169,970, 6,867,293, 7,183,110, 5,094,945, 6,225,114, 7,141,722, 7,045,684, 5,312,910, 6,566,587, and RE037287, each of which is herein incorporated by reference in its entirety.

Transformation of Bacterial or Plant Cells

Provided herein are novel isolated genes that confer resistance to an herbicide. Also provided are amino acid sequences of the GRG proteins of the invention. The protein resulting from translation of this gene allows cells to function in the presence of concentrations of an herbicide that are otherwise toxic to cells including plant cells and bacterial cells. In one aspect of the invention, the grg25, grg26, grg27, grg28, grg29, grg30, grg31, syngrg25, syngrg26, syngrg27, syngrg28, syngrg29, syngrg30, and syngrg31 genes are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art.

By engineering the genes of the invention to be expressed from a promoter known to stimulate transcription in the organism to be tested and properly translated to generate an intact GRG peptide, and placing the cells in an otherwise toxic concentration of herbicide, one can identify cells that have been transformed with the DNA by virtue of their resistance to herbicide. By "promoter" is intended a nucleic acid sequence that functions to direct transcription of a downstream coding sequence. The promoter, together with other transcriptional and translational regulatory nucleic acid sequences, (also termed as "control sequences") are necessary for the expression of a DNA sequence of interest.

Transformation of bacterial cells is accomplished by one of several techniques known in the art, including but not limited to electroporation or chemical transformation (see, for example, Ausubel, ed. (1994) *Current Protocols in Molecular Biology*, John Wiley and Sons, Inc., Indianapolis, Ind.). Markers conferring resistance to toxic substances are useful in identifying transformed cells (having taken up and expressed the test DNA) from non-transformed cells (those not containing or not expressing the test DNA). In one aspect of the invention, the grg25, grg26, grg27, grg28, grg29, grg30, grg31, syngrg25, syngrg26, syngrg27, syngrg28, syngrg29, syngrg30, and syngrg31 genes are useful as markers to assess transformation of bacterial or plant cells.

Transformation of plant cells can be accomplished in similar fashion. By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen). "Transgenic plants" or "transformed plants" or "stably transformed" plants or cells or tissues refer to plants that have incorporated or integrated exogenous nucleic acid sequences or DNA fragments into the plant cell. By "stable transformation" is intended that the nucleotide construct introduced into a plant integrates into the genome of the plant and is capable of being inherited by progeny thereof.

The grg genes of the invention may be modified to obtain or enhance expression in plant cells. The herbicide resistance sequences of the invention may be provided in expression cassettes for expression in the plant of interest. "Plant expression cassette" includes DNA constructs, including recombinant DNA constructs, that are capable of resulting in the expression of a protein from an open reading frame in a plant cell. The cassette will include in the 5'-3' direction of transcription, a transcriptional initiation region (i.e., promoter, particularly a heterologous promoter) operably-linked to a DNA sequence of the invention, and/or a transcriptional and translational termination region (i.e., termination region) functional in plants. The cassette may additionally contain at least one additional gene to be cotransformed into the organism, such as a selectable marker gene. Alternatively, the additional gene(s) can be provided on multiple expression cassettes. Such an expression cassette is provided with a plurality of restriction sites for insertion of the herbicide resistance sequence to be under the transcriptional regulation of the regulatory regions.

The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention. "Heterologous" generally refers to the nucleic acid sequences that are not endogenous to the cell or part of the native genome in which they are present, and have been added to the cell by infection, transfection, microinjection, electroporation, microprojection, or the like. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

Often, such constructs will also contain 5' and 3' untranslated regions. Such constructs may contain a "signal sequence" or "leader sequence" to facilitate co-translational or post-translational transport of the peptide of interest to certain intracellular structures such as the chloroplast (or other plastid), endoplasmic reticulum, or Golgi apparatus, or to be secreted. For example, the gene can be engineered to contain a signal peptide to facilitate transfer of the peptide to the endoplasmic reticulum. By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like. It may also be preferable to engineer the plant expression cassette to contain an intron, such that mRNA processing of the intron is required for expression.

By "3' untranslated region" is intended a nucleotide sequence located downstream of a coding sequence. Polyadenylation signal sequences and other sequences encoding regulatory signals capable of affecting the addition of polyadenylic acid tracts to the 3' end of the mRNA precursor are 3' untranslated regions. By "5' untranslated region" is intended a nucleotide sequence located upstream of a coding sequence.

Other upstream or downstream untranslated elements include enhancers. Enhancers are nucleotide sequences that act to increase the expression of a promoter region. Enhancers are well known in the art and include, but are not limited to, the SV40 enhancer region and the 35S enhancer element.

The termination region may be native with the transcriptional initiation region, may be native with the herbicide resistance sequence of the present invention, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

In one aspect of the invention, synthetic DNA sequences are designed for a given polypeptide, such as the polypeptides of the invention. Expression of the open reading frame of the synthetic DNA sequence in a cell results in production of the polypeptide of the invention. Synthetic DNA sequences can be useful to simply remove unwanted restriction endonuclease sites, to facilitate DNA cloning strategies, to alter or remove any potential codon bias, to alter or improve GC content, to remove or alter alternate reading frames, and/or to alter or remove intron/exon splice recognition sites, polyadenylation sites, Shine-Delgarno sequences, unwanted promoter elements and the like that may be present in a native DNA sequence. It is also possible that synthetic DNA sequences may be utilized to introduce other improvements to a DNA sequence, such as introduction of an intron sequence, creation of a DNA sequence that in expressed as a protein fusion to organelle targeting sequences, such as chloroplast transit peptides, apoplast/vacuolar targeting peptides, or peptide sequences that result in retention of the resulting peptide in the endoplasmic reticulum. Synthetic genes can also be synthesized using host cell-preferred codons for improved expression, or may be synthesized using codons at a host-preferred codon usage frequency. See, for example, Campbell and Gowri (1990) *Plant Physiol.* 92:1-11; U.S. Pat. Nos. 6,320,100; 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Typically this "plant expression cassette" will be inserted into a "plant transformation vector." By "transformation vector" is intended a DNA molecule that is necessary for efficient transformation of a cell. Such a molecule may consist of one or more expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-45 1). "Vector" refers to a nucleic acid construct designed for transfer between different host cells. "Expression vector" refers to a vector that has the ability to incorporate, integrate and express heterologous DNA sequences or fragments in a foreign cell.

This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science,* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene and in this case "glyphosate") to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent (e.g. "glyphosate"). The shoots are then transferred to a selective rooting medium for recovering rooted shoot or plantlet. The transgenic plantlet then grow into mature plant and produce fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants. Molecular and biochemical methods can then be used to confirm the presence of the integrated heterologous gene of interest in the genome of transgenic plant.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Plants

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

This invention is particularly suitable for any member of the monocot plant family including, but not limited to, maize, rice, barley, oats, wheat, sorghum, rye, sugarcane, pineapple, yams, onion, banana, coconut, and dates.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*, Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragments to confirm the integration of the introduced gene in the plant genome according to standard techniques (Sambrook and Russell, 2001, supra).

In Northern analysis, RNA is isolated from specific tissues of transformant, fractionated in a formaldehyde agarose gel, blotted onto a nylon filter according to standard procedures that are routinely used in the art (Sambrook and Russell, 2001, supra). Expression of RNA encoded by grg25, grg26, grg27, grg28, grg29, grg30, grg31, syngrg25, syngrg26, syngrg27, syngrg28, syngrg29, syngrg30, and syngrg31 is then tested by hybridizing the filter to a radioactive probe derived from a polynucleotide of the invention, by methods known in the art (Sambrook and Russell, 2001, supra)

Western blot and biochemical assays and the like may be carried out on the transgenic plants to determine the presence of protein encoded by the herbicide resistance gene by standard procedures (Sambrook and Russell, 2001, supra) using antibodies that bind to one or more epitopes present on the herbicide resistance protein.

Methods for Increasing Plant Yield

Methods for increasing plant yield are provided. The methods comprise introducing into a plant or plant cell a polynucleotide comprising a grg sequence disclosed herein. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase.

In specific methods, the plant is treated with an effective concentration of an herbicide, where the herbicide application results in enhanced plant yield. By "effective concentration" is intended the concentration which allows the increased yield in the plant. Such effective concentrations for herbicides of interest are generally known in the art. The herbicide may be applied either pre- or post emergence in accordance with usual techniques for herbicide application to fields comprising crops which have been rendered resistant to the herbicide by heterologous expression of a grg gene of the invention.

Methods for conferring herbicide resistance in a plant or plant part are also provided. In such methods, a grg polynucleotide disclosed herein is introduced into the plant, wherein expression of the polynucleotide results in glyphosate tolerance or resistance. Plants produced via this method can be treated with an effective concentration of an herbicide and display an increased tolerance to the herbicide. An "effective concentration" of an herbicide in this application is an amount sufficient to slow or stop the growth of plants or plant parts that are not naturally resistant or rendered resistant to the herbicide.

In another embodiment, methods for conferring herbicide resistance in a plant or plant part are provided, wherein the plant or plant part is grown under higher or lower than ambient environmental temperatures as described supra. Glyphosate tolerant EPSP synthase enzymes having thermal stability at higher or lower temperatures, or have temperature optima at higher or lower temperatures, are useful for conferring glyphosate tolerance in plants that are grown under such conditions.

Methods of Controlling Weeds in a Field

Methods for selectively controlling weeds in a field containing a plant are also provided. In one embodiment, the plant seeds or plants are glyphosate resistant as a result of a grg polynucleotide disclosed herein being inserted into the plant seed or plant. In specific methods, the plant is treated with an effective concentration of an herbicide, where the herbicide application results in a selective control of weeds or other untransformed plants. By "effective concentration" is intended the concentration which controls the growth or spread of weeds or other untransformed plants without significantly affecting the glyphosate-resistant plant or plant seed. Such effective concentrations for herbicides of interest are generally known in the art. The herbicide may be applied either pre- or post emergence in accordance with usual techniques for herbicide application to fields comprising plants or plant seeds which have been rendered resistant to the herbicide.

The following examples are offered by way of illustration and not by way of limitation.

EXPERIMENTAL

Example 1

Isolation of ATX8909

ATX8909 was isolated by plating samples of soil on HEPES Mineral Salts Medium (HMSM) containing glyphosate as the sole source of phosphorus. Since HMSM contains no aromatic amino acids, a strain must be resistant to glyphosate in order to grow on this media.

Two grams of soil were suspended in approximately 10 ml of water, vortexed for 15 seconds and permitted to settle for 15 minutes. A 10 µl loopful of this suspension was added to 3 ml of HMSM supplemented with 10 mM glyphosate (pH 7.0). HMSM contains (per liter): 10 g glucose, 2 g $NH_4SO_4$, 9.53 g HEPES, 1.0 ml 0.8 M $MgSO_4$, 1.0 ml 0.1 M $CaCl_2$, 1.0 ml Trace Elements Solution (In 100 ml of 1000× solution: 0.1 g $FeSO_4.7H_2O$, 0.5 mg $CuSO_4.5H_2O$, 1.0 mg $H_3BO_3$, 1.0 mg $MnSO_4.5H_2O$, 7.0 mg $ZnSO_4.7H_2O$, 1.0 mg $MoO_3$, 4.0 g KCl). The culture was grown in a shaker incubator for four days at 28° C. and then 20 µl was used to inoculate 2.5 ml of fresh HMSM containing 10 mM glyphosate as the only phosphorus source. After two days, 20 µl was used to inoculate another fresh 2.5 ml culture. After 5 days, 20 µl was used to inoculate a fresh 2.5 ml culture. After sufficient growth, the culture was plated onto solid media by streaking a 1 µl loop onto the surface of agar plate containing HMSM agar containing 100 mM glyphosate as the sole phosphorus source and stored at 28° C. The culture was then replated for isolation. One particular strain, designated ATX8909, was selected due to its ability to grow in the presence of high glyphosate concentrations.

Strains ATX1367, ATX1394, ATX21307, ATX21310, ATX21315 and ATX21318 were isolated as described above and found to grow in a liquid minimal medium containing up to 300 mM glyphosate. Each of the strains was tested by 16S rDNA sequencing or fatty acid content by methods known in the art to identify the strain. The strain identifications are shown in Table 1:

TABLE 1

| Strain Name | Strain ID | EPSP synthase Gene Name |
| --- | --- | --- |
| ATX8909 | Arthrobacter arilaiti | grg25 |
| ATX21307 | Arthrobacter ramosus | grg26 |
| ATX21310 | Gram + (no match to MIDI database) | grg27 |
| ATX21315 | Arthrobacter ureafaciens | grg28 |
| ATX1367 | Paenibacillus pabuli | grg29 |
| ATX1394 | Paenibacillus pabuli | grg30 |
| ATX21318 | Sphingobacterium multivorum/faecium | grg30 |

Example 2

Cloning of Glyphosate-Resistant EPSP Synthases

Genomic DNA was extracted from the strains described in Table 1 and the resulting DNA was partially digested with restriction enzyme Sau3A 1 to yield DNA fragments approximately 5 kilobases in size. These DNA molecules were size selected on agarose gels, purified, and ligated into LAMBDA ZAP® vector arms pre-digested with BamH I. The ligated arms were then packaged into phage particles, and phage titers determined as known in the art. The resulting libraries were amplified by methods known in the art to generate a library titer of between $3\times10^7$ and $3\times10^8$ PFU/mL. For each independent library, E. coli (XL1 Blue MRF') was then co-transfected with phage from an amplified library as well as M13 helper phage into to allow mass excision of the library in the form of an infectious, circular ssDNA as known in the art (Short et al. (1988) Nucleic Acids Research 16:7583-7600). After centrifugation of the co-infected cells, the phage-containing supernatant was heated to 65-70° C. for 15-20 minutes to incapacitate any residual lambda phage particles. Dilutions of the resulting ssDNA plasmid library were transfected into a fresh culture of competent E. coli XL-Blue MRF'(aroA) cells (XL1 Blue MRF'). The resulting transfected cells were plated onto M63 plates containing kanamycin, 0.1 mM IPTG and either 0 mM, 20 mM or 50 mM glyphosate.

The E. coli XL-Blue MRF'(aroA) used for the transfection expresses the F-pilus, and also contains a deletion of the aroA gene encoding the endogenous E. coli EPSP synthase enzyme. This strain is also referred to as herein as ΔaroA. This ΔaroA strain is unable to grow on minimal media lacking aromatic amino acids, unless complemented by a functional EPSP synthase. Since glyphosate is a potent inhibitor of typical, glyphosate-sensitive EPSP synthases, such as type I EPSP synthases, transfected clones expressing a non-glyphosate resistant EPSP synthase would be able to grown on M63 plates lacking glyphosate, but would be unable to grow on M63 containing either 20 mM or 50 mM glyphosate. In order to grow on M63 plates containing 20 mM or 50 mM glyphosate, the cells must contain a plasmid that expresses an EPSP synthase that is both (1) capable of complementing the ΔaroA mutation of these cells, and (2) resistant to glyphosate. Thus, this screening method allows identification of clones containing glyphosate-resistant EPSP synthases.

Colonies growing on 20 mM or 50 mM glyphosate were picked and their plasmids analyzed by restriction digest to identify plasmids with shared restriction patterns. Individual plasmids were sequenced by methods known in the art, with preference given to plasmids that conferred resistance to 50 mM glyphosate.

Using this approach, as sometimes modified for each library as known and appreciated in the art, library clones containing EPSP synthase genes were identified for each of the seven strains of Table 1.

Example 3

DNA and Protein Sequences of EPSP Synthases

The DNA sequences of the glyphosate-resistant EPSP synthases was determined for each of the clones in Table 2 by methods well known in the art.

grg25. The DNA sequence of grg25 is provided herein as SEQ ID NO:1. The predicted translation product of grg25 (GRG25) is provided herein as SEQ ID NO:2.

grg26. The DNA sequence of grg26 is provided herein as SEQ ID NO:3. The predicted translation product of grg26 (GRG26) is provided herein as SEQ ID NO:4.

grg27. The DNA sequence of grg27 is provided herein as SEQ ID NO:5. The predicted translation product of grg27 (GRG27) is provided herein as SEQ ID NO:6.

grg28. The DNA sequence of grg28 is provided herein as SEQ ID NO: 7. The predicted translation product of grg28 (GRG28) is provided herein as SEQ ID NO:8.

grg29. The DNA sequence of grg29 is provided herein as SEQ ID NO:9. The predicted translation product of grg29 (GRG29) is provided herein as SEQ ID NO:10.

grg30. The DNA sequence of grg30 is provided herein as SEQ ID NO:11. The predicted translation product of grg30 (GRG30) is provided herein as SEQ ID NO:12.

grg31. The DNA sequence of grg31 is provided herein as SEQ ID NO:13. The predicted translation product of grg31 (GRG31) is provided herein as SEQ ID NO: 14.

syngrg31. The synthetic DNA sequence of syngrg31 is provided herein as SEQ ID NO:28. The predicted translation product of syngrg1 is identical to that of grg31, and is provided herein as SEQ ID NO:14.

syngrg25. The synthetic DNA sequence of syngrg25 is provided herein as SEQ ID NO:29. The predicted translation product of syngrg1 is identical to that of grg25, and is provided herein as SEQ ID NO:2.

syngrg26. The synthetic DNA sequence of syngrg26 is provided herein as SEQ ID NO:30. The predicted translation product of syngrg1 is identical to that of grg26, and is provided herein as SEQ ID NO: 4.

syngrg27. The synthetic DNA sequence of syngrg27 is provided herein as SEQ ID NO:31. The predicted translation product of syngrg1 is identical to that of grg27, and is provided herein as SEQ ID NO:6.

syngrg28. The synthetic DNA sequence of syngrg28 is provided herein as SEQ ID NO:32. The predicted translation product of syngrg1 is identical to that of grg28, and is provided herein as SEQ ID NO:8.

syngrg29. The synthetic DNA sequence of syngrg29 is provided herein as SEQ ID NO:33. The predicted translation product of syngrg1 is identical to that of grg29, and is provided herein as SEQ ID NO:10.

syngrg30. The synthetic DNA sequence of syngrg30 is provided herein as SEQ ID NO:34. The predicted translation product of syngrg1 is identical to that of grg30, and is provided herein as SEQ ID NO:12.

Clones containing each of the grg25, grg26, grg27, grg28, grg29, grg30, and grg31 EPSP synthase genes were deposited at NRRL, and assigned deposit numbers as in Table 2.

TABLE 2

Clones containing glyphosate-resistant EPSP synthases

| EPSPS | Strain yielding EPSPS | Original Isolate in pBKCMV | NRRL Number |
|---|---|---|---|
| GRG25 | ATX8909 | pAX1932 | NRRL B-30911 |
| GRG26 | ATX21307 | pAX1933 | NRRL B-30912 |
| GRG27 | ATX21310 | pAX1934 | NRRL B-30913 |
| GRG28 | ATX21315 | pAX1935 | NRRL B-30914 N |
| GRG31 | ATX21318 | pAX1936 | NRRL B-30915 |
| GRG30 | ATX1394 | pAX1937 | NRRL B-30916 N |
| GRG29 | ATX1367 | pAX1938 | NRRL B-30917 N |

Each of the proteins GRG25-GRG31 showed homology to EPSP synthase enzymes in the NCBI database by BLAST search. The EPSPS enzyme with the highest protein sequence identity to each GRG enzyme is listed in the following table.

TABLE 3

Homology of GRG25-GRG31 to known EPSP synthases

| Protein | Strain with homologous EPSPS enzyme | % Identity |
|---|---|---|
| GRG25 | *Nocardia farcinica* | 50.5 |
| GRG26 | *Arthrobacter* sp. FB24 | 82.9 |
| GRG27 | *Arthrobacter* sp. FB24 | 78 |
| GRG28 | *Arthrobacter* sp. FB24 | 81.4 |
| GRG29 | *Symbiobacterium thermophilum* | 51.6 |
| GRG30 | *Symbiobacterium thermophilum* | 51.3 |
| GRG31 | *Bacteroides fragilis* | 43.3 |

Example 4

Cloning of Novel Glyphosate-Resistant EPSP Synthases into an *E. coli* Expression Vector The EPSP synthase genes contained in the clones of Table 2 were sub-cloned into the *E. coli* expression vector pRSF1b (Invitrogen). Resulting clones were confirmed by DNA sequencing, and used to induce expression of each EPSP synthase in *E. coli*. The expressed His-tagged protein was then purified as known in the art.

Example 5

Glyphosate Resistance of EPSP Synthases

The pRSF1b clones were plated onto M63+ plates containing antibiotic and either 0 mM or 50 mM glyphosate. Growth was scored after two days growth at 37° C. All of the seven EPSP synthases were observed to confer resistance to 50 mM glyphosate in *E. coli* cells (Table 4).

TABLE 4

Glyphosate screen

| EPSPS | Clone in pRSF1B | Growth on 50 mM glyphosate |
|---|---|---|
| Vector | — | — |
| GRG25 | pAX1939 | +++ |
| GRG26 | pAX1940 | +++ |
| GRG27 | pAX1941 | +++ |
| GRG28 | pAX1942 | +++ |
| GRG30 | pAX1944 | +++ |
| GRG29 | pAX1943 | +++ |
| GRG31 | pAX1945 | +++ |

Example 6

Temperature Optimum of GRG31 Enzymatic Activity

A vector that places expression of GRG31 under the control of the viral T7 promoter was constructed (pAX3535) and used to transform an *E. coli* strain possessing the viral T7 gene immediately 3' to a lactose inducible promoter. Following IPTG induction, the GRG31 protein was purified to homogeneity by standard methods. To measure enzymatic activity, the purified GRG31 enzyme was diluted to an appropriate assay concentration in buffer containing HEPES (50 mM, pH 7) and 50 mM KCl, and then incubated for 15 minutes at either 10, 20, 30, 40, 50 or 60° C. Following incubation, the enzyme was heated to 90° C. for 1 minute to denature the enzyme, and then cooled to 4° C. The phosphate generated by each reaction was then added to a second assay containing inosine, purine nucleoside phosphorylase, xanthine oxidase, horseradish peroxidase, and the fluorescent substrate AMPLEX® Red (U.S. Patent Application No. 60/741,166, filed Dec. 1, 2005). Following incubation for 15 minutes at room temperature, fluorescent product was quantified using a Gemini XPS spectrofluorometer (Molecular Devices Corporation, Sunnyvale, Calif.). EPSP synthase product formation was measured, and is expressed in Table 5 as a percentage of maximal activity.

TABLE 5

Temperature optimum for GRG31

| Temperature, ° C. | Percentage of Maximal Activity |
|---|---|
| 10 | 42% |
| 20 | 62% |
| 30 | 69% |
| 40 | 80% |
| 50 | 100% |
| 60 | 96% |
| 70 | 67% |
| 80 | 36% |

Example 7

Thermal Stability of GRG31 Enzymatic Activity

A vector that places expression of GRG31 under the control of the viral T7 promoter was constructed (pAX3535) and used to transform an *E. coli* strain possessing the viral T7 gene immediately 3' to a lactose inducible promoter. Following IPTG induction, the GRG31 protein was purified to homogeneity by standard methods. To measure enzymatic activity, the purified GRG31 enzyme was diluted to an appropriate assay concentration in buffer containing HEPES (50 mM, pH 7) and 50 mM KCl, and then incubated at 37° C. for 0, 2, 6 or 22 hours. A control sample was incubated alongside at 4° C. At each timepoint, an aliquot was removed from each sample and enzymatic assays were carried out in a final volume of 50 µl containing 0.5 mM shikimate-3-phosphate, 200 uM phosphoenolpyruvate (PEP), 1 U/ml xanthine oxidase, 2 U/ml nucleoside phosphorylase, 2.25 mM inosine, 1 U/ml horseradish peroxidase, 2 mM glyphosate, 50 mM HEPES/KOH pH 7.0, 100 mM KCl, and AMPLEX® Red (Invitrogen) according to the manufacturer's instructions. Assays were started by adding shikimate-3-phosphate. EPSP synthase activity was measured using a Spectramax Gemini XPS fluorescence spectrometer (Molecular Dynamics, excitation: 555 nm; emission: 590 nm). EPSP synthase thermal stability was calculated as the percentage of enzymatic activity at each timepoint at 37° C. relative to enzymatic activity in the control sample incubated alongside at 4° C. (Table 6).

TABLE 6

Thermal stability of GRG31

| Time, hours | Percentage of control |
|---|---|
| 0 | 100% |
| 2 | 86% |
| 6 | 68% |
| 22 | 29% |

Example 8

Engineering of grg25, grg26, grg27, grg28, grg29, grg30, grg31 and syngrg25, syngrg26, syngrg27, syngrg28, syngrg29, syngrg30, and syngrg31 for Plant Transformation The open reading frame (ORF) for each of the grg genes is amplified by PCR from a full-length cDNA template. Hind III restriction sites are added to each end of the ORF during PCR. Additionally, the nucleotide sequence ACC is added immediately 5' to the start codon of the gene to increase translational efficiency (Kozak (1987) *Nucleic Acids Research* 15:8125-8148; Joshi (1987) *Nucleic Acids Research* 15:6643-6653). The PCR product is cloned and sequenced, using techniques well known in the art, to ensure that no mutations are introduced during PCR. The plasmid containing the grg PCR product is digested with, for example, Hind III and the fragment containing the intact ORF is isolated.

One may generate similar constructs that contain a chloroplast targeting sequence linked to the polynucleotide of the invention by methods known in the art.

A DNA fragment containing the EPSP synthase (and either containing or not containing a chloroplast targeting sequence) is cloned into a plasmid, for example at the Hind III site of pAX200. pAX200 is a plant expression vector containing the rice actin promoter (McElroy et al. (1991) *Molec. Gen. Genet.* 231:150-160), and the PinII terminator (An et al. (1989) *The Plant Cell* 1:1 15-122). The promoter-gene-terminator fragment (or the promoter-leader-gene-terminator fragment) from this intermediate plasmid is subcloned into a plasmid such as pSB11 (Japan Tobacco, Inc.) to form a final plasmid, referred to herein as, for example, pSB11GRG25. pSB11GRG25 is organized such that the DNA fragment containing, for example, the promoter-grg25-terminator construct (or the promoter-leader-grg25-terminator construct) may be excised by appropriate restriction enzymes and also used for transformation into plants, for example, by aerosol beam injection. The structure of pSB11GRG25 is verified by restriction digest and gel electrophoresis, as well as by sequencing across the various cloning junctions. The same methods can be used to generate a final plasmid for each of the grg genes described herein.

The plasmid is mobilized into *Agrobacterium tumefaciens* strain LBA4404 which also harbors the plasmid pSB1 (Japan Tobacco, Inc.), using triparental mating procedures well known in the art, and plating on media containing antibiotic. Plasmid pSB11GRG25 carries spectinomycin resistance but is a narrow host range plasmid and cannot replicate in *Agrobacterium*. Antibiotic resistant colonies arise when pSB11GRG25 integrates into the broad host range plasmid pSB1 through homologous recombination. The resulting cointegrate product is verified by Southern hybridization. The *Agrobacterium* strain harboring the cointegrate can be used to transform maize, for example, by the PureIntro method (Japan Tobacco).

Example 9

Transformation of grg25, grg26, grg27, grg28, grg29, grg30, grg31, syngrg25, syngrg26, syngrg27, syngrg28, syngrg29, syngrg30, and syngrg31 into Plant Cells Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to express the GRG proteins of the present invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

TABLE 7

| DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000× Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 10

Transformation of grg25, grg26, grg27, grg28, grg29, grg30, grg31, syngrg25, syngrg26, syngrg27, syngrg28, syngrg29, or syngrg31 into Maize Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated or recombinant nucleic acid molecule comprising a nucleotide sequence selected from the group consisting of:
   a) the nucleotide sequence of SEQ ID NOS:13 or 28, or a complement thereof;
   b) the herbicide resistance nucleotide sequence of the DNA insert of the plasmid deposited as Accession No. NRRL B-30917 N, or a complement thereof;
   c) a nucleotide sequence that encodes a polypeptide comprising the amino acid sequence of SEQ ID NO: 14; and,
   d) a nucleotide sequence encoding a polypeptide having at least 95% amino acid sequence identity to the amino acid sequence of SEQ ID NO:14, wherein said polypeptide has EPSP synthase and herbicide resistance activity, and wherein said nucleotide sequence is operably linked to a heterologous promoter.

2. The isolated or recombinant nucleic acid molecule of claim 1, wherein said nucleotide sequence is a synthetic sequence that has been designed for expression in a plant.

3. A vector comprising the nucleic acid molecule of claim 1.

4. The vector of claim 3, further comprising a nucleic acid molecule encoding a heterologous polypeptide.

5. A host cell that contains the recombinant nucleic acid molecule of claim 1.

6. The host cell of claim 5 that is a bacterial host cell.

7. The host cell of claim 5 that is a plant cell.

8. A transgenic plant comprising the host cell of claim 7.

9. The plant of claim 8, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

10. A transgenic seed comprising the recombinant nucleic acid of claim 1.

11. A method for producing a polypeptide with herbicide resistance activity, comprising culturing the host cell of claim 5 under conditions in which a nucleic acid molecule encoding the polypeptide is expressed, said polypeptide being selected from the group consisting of:
   a) a polypeptide comprising the amino acid sequence of SEQ ID NO:14;
   b) a polypeptide encoded by the nucleic acid sequence of SEQ ID NOS:13 or 28;
   c) a polypeptide comprising an amino acid sequence having at least 95% sequence identity to a polypeptide with the amino acid sequence of SEQ ID NO:14, wherein said polypeptide has EPSP synthase and herbicide resistance activity; and
   d) a polypeptide that is encoded by the herbicide resistance nucleotide sequence of the DNA insert of the plasmid deposited as Accession No. NRRL B-30917 N.

12. A method for conferring resistance to an herbicide in a plant, said method comprising transforming said plant with a DNA construct, said construct comprising a promoter that drives expression in a plant cell operably linked with a nucleotide sequence, and regenerating a transformed plant, wherein said nucleotide sequence is selected from the group consisting of:
   a) the nucleotide sequence of SEQ ID NOS:13 or 28, or a complement thereof;
   b) the herbicide resistance nucleotide sequence of the DNA insert of the plasmid deposited as Accession No. NRRL B-30917 N, or a complement thereof;
   c) a nucleotide sequence that encodes a polypeptide comprising the amino acid sequence of SEQ ID NO:14; and,
   d) a nucleotide sequence encoding a polypeptide having at least 95% amino acid sequence identity to the amino acid sequence of SEQ ID NO:14, wherein said polypeptide has EPSP synthase and herbicide resistance activity.

13. A plant having stably incorporated into its genome a DNA construct comprising a nucleotide sequence that encodes a protein having herbicide resistance activity, wherein said nucleotide sequence is selected from the group consisting of:
   a) a nucleotide sequence of SEQ ID NOS:13 or 28;
   b) a nucleotide sequence encoding a polypeptide comprising an amino acid sequence of SEQ ID NO:14;
   c) a nucleotide sequence encoding a polypeptide having at least 95% amino acid sequence identity to the amino acid sequence of SEQ ID NO:14, wherein said polypeptide has EPSP synthase and herbicide resistance activity; and,
   d) the herbicide resistance nucleotide sequence of the DNA insert of the plasmid deposited as Accession No. NRRL B-30917 N; wherein said nucleotide sequence is operably linked to a promoter that drives expression of a coding sequence in a plant cell.

14. The plant of claim 13, wherein said plant is a plant cell.

15. A method for increasing vigor or yield in a plant comprising:
   a) introducing into said plant the recombinant nucleotide sequence of claim 1;
   b) contacting said plant with an effective concentration of glyphosate; and,
   c) growing said plant under conditions wherein the temperature is higher than ambient environmental temperature for at least two consecutive hours per day for at least four days following contact with said glyphosate, wherein said days following contact is within the growing season of the plant, wherein the vigor or yield of said plant is higher than the vigor or yield of a plant expressing a glyphosate tolerance EPSP synthase that does not have a temperature optimum higher than ambient environmental temperature.

16. The method of claim 15, wherein said EPSP synthase is not a plant-derived EPSP synthase.

17. The method of claim 15, wherein said EPSP synthase enzyme has a temperature optimum from about 35° C. to about 55° C. and the temperature in step (c) is about 35° C. to about 55° C.

18. The method of claim 15, wherein said EPSP synthase enzyme is set forth in SEQ ID NO:14 and the temperature in step (b) is about 45° C. to about 55° C.

19. A method for conferring resistance to glyphosate in a plant comprising:
   a) introducing into said plant the recombinant nucleotide sequence of claim 1;
   b) contacting said plant with an effective concentration of glyphosate; and,
   c) growing said plant under conditions wherein the temperature is higher than ambient environmental temperature for at least two consecutive hours per day for at least four days following contact with said glyphosate, wherein said days following contact is within the growing season of the plant.

20. The method of claim 19, wherein said EPSP synthase is not a plant-derived EPSP synthase.

21. The method of claim 19, wherein said EPSP synthase enzyme has thermal stability at a temperature from about 32° C. to about 60° C. and the temperature in step (b) is about 32° C. to about 60° C.

22. The method of claim 21, wherein said EPSP synthase enzyme has thermal stability at a temperature from about 35° C. to about 45° C. and the temperature in step (b) is about 35° C. to about 45° C.

23. The method of claim 19, wherein said EPSP synthase enzyme is set forth in SEQ ID NO:14 and the temperature in step (b) is about 37° C.

* * * * *

SEQUENCE LISTING

<160> NUMBER OF SEQ ID NOS: 38

<210> SEQ ID NO 1
<211> LENGTH: 1404
<212> TYPE: DNA
<213> ORGANISM: Arthrobacter arilaiti
<220> FEATURE:
<221> NAME/KEY: CDS
<222> LOCATION: (1)...(1404)

<400> SEQUENCE: 1

```
atg ctg ctg cgc acc gtg aaa aca tgc ctc gag ccg aag gat cta cca      48
Met Leu Leu Arg Thr Val Lys Thr Cys Leu Glu Pro Lys Asp Leu Pro
 1               5                  10                  15 atc tgt act gca agc gcc cct gga agc cca acc gat aag ctg cac aac      96
Ile Cys Thr Ala Ser Ala Pro Gly Ser Pro Thr Asp Lys Leu His Asn
             20                  25                  30 gca gaa aag acc tgg tgg gcc gcg cct cat gcc gcc acc ggc ctg gac     144
Ala Glu Lys Thr Trp Trp Ala Ala Pro His Ala Ala Thr Gly Leu Asp
         35                  40                  45 gcc atc gtc tcg gtg ccc gct tcg aag tcc ttg acc aac cgg tat ctg     192
Ala Ile Val Ser Val Pro Ala Ser Lys Ser Leu Thr Asn Arg Tyr Leu
     50                  55                  60 atc ctg gcg gcc ctg gcc tcc tcg cca tcc acc atc cac aac acg ctc     240
Ile Leu Ala Ala Leu Ala Ser Ser Pro Ser Thr Ile His Asn Thr Leu
 65                  70                  75                  80 atc agc cgc gac acc gaa ctg atg ctc gat gcg ctg gcc gct ttc ggc     288
Ile Ser Arg Asp Thr Glu Leu Met Leu Asp Ala Leu Ala Ala Phe Gly
                 85                  90                  95 atc ggc atc gaa cgc acc acg cag cca gat ggc tcc acc acc gtg gcc     336
Ile Gly Ile Glu Arg Thr Thr Gln Pro Asp Gly Ser Thr Thr Val Ala
            100                 105                 110 atc acc ccg ggc aag ctg gcc acc ggc ccg ctg tcc atc gac tgc ggc     384
Ile Thr Pro Gly Lys Leu Ala Thr Gly Pro Leu Ser Ile Asp Cys Gly
        115                 120                 125 ctg gcc ggc acc gtc atg cgc ttc gtt ccg ccg ctg gcc gcc gtt gcc     432
Leu Ala Gly Thr Val Met Arg Phe Val Pro Pro Leu Ala Ala Val Ala
    130                 135                 140 ggt gcc agc gtg gca ttc gat ggc gat gaa gca gcc cgc gtg cgc ccg     480
Gly Ala Ser Val Ala Phe Asp Gly Asp Glu Ala Ala Arg Val Arg Pro
145                 150                 155                 160 atg gcc ccg gtg ctc gac gcc ttg gaa acc ctg ggt gcc cgg atc gaa     528
Met Ala Pro Val Leu Asp Ala Leu Glu Thr Leu Gly Ala Arg Ile Glu
                165                 170                 175 tat gcc ggc act ccc ggc atg ctg ccc ttc acc atg gac gcc agc gca     576
Tyr Ala Gly Thr Pro Gly Met Leu Pro Phe Thr Met Asp Ala Ser Ala
            180                 185                 190 ttg cag gag cgc cac gag gtg ctc atc gac gcc tcg ggc agc tcc cag     624
Leu Gln Glu Arg His Glu Val Leu Ile Asp Ala Ser Gly Ser Ser Gln
        195                 200                 205 ttc atc tcc gca ctg ctg gtc ggc caa gca ctg ccc ggt ggg ctg         672
Phe Ile Ser Ala Leu Leu Val Gly Gln Ala Leu Pro Gly Gly Leu
    210                 215                 220 aag ctg cgg gcc gcc gcg ggg cat atc gcc tcc cct gac cac att gcc     720
Lys Leu Arg Ala Ala Ala Gly His Ile Ala Ser Pro Asp His Ile Ala
225                 230                 235                 240 atg acc gtg caa acc ctg cgc gaa ctg ggc gtc gag gta gcc gtg ggc     768
Met Thr Val Gln Thr Leu Arg Glu Leu Gly Val Glu Val Ala Val Gly
                245                 250                 255 gag gat gca cgc agc tgg tcc atc gca ccg ggt cag ctt tcc ggg ttc     816
Glu Asp Ala Arg Ser Trp Ser Ile Ala Pro Gly Gln Leu Ser Gly Phe
```

```
                    260                 265                 270
act atc acc gtg gaa ccg gac ctg tcc aac gcc ggt ccc ttc ctg gcg       864
Thr Ile Thr Val Glu Pro Asp Leu Ser Asn Ala Gly Pro Phe Leu Ala
        275                 280                 285 gcc gcc ttg gcc acc aac ggc acc gtg cgc gtg ccc ttc tgg cct gca       912
Ala Ala Leu Ala Thr Asn Gly Thr Val Arg Val Pro Phe Trp Pro Ala
    290                 295                 300 tcc acc acc cag gtg ggc ggc aaa tgg gtg cag atc cta agc cgg atg       960
Ser Thr Thr Gln Val Gly Gly Lys Trp Val Gln Ile Leu Ser Arg Met
305                 310                 315                 320 ggc gca gaa atc agc cac ggc gag gac gga gtg ctc acc gta cgc ggc      1008
Gly Ala Glu Ile Ser His Gly Glu Asp Gly Val Leu Thr Val Arg Gly
                325                 330                 335 acc gga gtg atc cgc ggc atc gac tac gcc gat gcc tcc gaa ttg gct      1056
Thr Gly Val Ile Arg Gly Ile Asp Tyr Ala Asp Ala Ser Glu Leu Ala
            340                 345                 350 ccc acc ctg gcc gcg ctg tgc acc ctg gcg gac tcc ccc agc aag ctg      1104
Pro Thr Leu Ala Ala Leu Cys Thr Leu Ala Asp Ser Pro Ser Lys Leu
        355                 360                 365 acc ggc atc ggg cac ctg cgc ggg cac gaa acg gac cgg ctg gcg gca      1152
Thr Gly Ile Gly His Leu Arg Gly His Glu Thr Asp Arg Leu Ala Ala
    370                 375                 380 ctg gaa acc gag ctt gcc aag gtc ggt gcc acg gtg acc tcc acc gac      1200
Leu Glu Thr Glu Leu Ala Lys Val Gly Ala Thr Val Thr Ser Thr Asp
385                 390                 395                 400 gac gcg ttg gaa atc att ccc gga acc ctg cag gca gcc gat ctg gac      1248
Asp Ala Leu Glu Ile Ile Pro Gly Thr Leu Gln Ala Ala Asp Leu Asp
                405                 410                 415 tcc tac gag gat cac cgg atg gcc acc gca ggc gca ctg ctg ggc ctg      1296
Ser Tyr Glu Asp His Arg Met Ala Thr Ala Gly Ala Leu Leu Gly Leu
            420                 425                 430 gcc atc gaa ggg gtg cgc gtg gaa aat atc gcc acc acc gcc aag acc      1344
Ala Ile Glu Gly Val Arg Val Glu Asn Ile Ala Thr Thr Ala Lys Thr
        435                 440                 445 atg ccc gac ttc ccg caa ctc tgg acc gac atg gcc gcc acc gca aag      1392
Met Pro Asp Phe Pro Gln Leu Trp Thr Asp Met Ala Ala Thr Ala Lys
    450                 455                 460 ggc cag ggc taa                                                      1404
Gly Gln Gly *
465

<210> SEQ ID NO 2
<211> LENGTH: 467
<212> TYPE: PRT
<213> ORGANISM: Arthrobacter arilaiti

<400> SEQUENCE: 2

Met Leu Leu Arg Thr Val Lys Thr Cys Leu Glu Pro Lys Asp Leu Pro
 1               5                  10                  15

Ile Cys Thr Ala Ser Ala Pro Gly Ser Pro Thr Asp Lys Leu His Asn
            20                  25                  30

Ala Glu Lys Thr Trp Trp Ala Ala Pro His Ala Ala Thr Gly Leu Asp
        35                  40                  45

Ala Ile Val Ser Val Pro Ala Ser Lys Ser Leu Thr Asn Arg Tyr Leu
    50                  55                  60

Ile Leu Ala Ala Leu Ala Ser Ser Pro Ser Thr Ile His Asn Thr Leu
65                  70                  75                  80

Ile Ser Arg Asp Thr Glu Leu Met Leu Asp Ala Leu Ala Ala Phe Gly
                85                  90                  95
```

Ile Gly Ile Glu Arg Thr Thr Gln Pro Asp Gly Ser Thr Thr Val Ala
            100                 105                 110

Ile Thr Pro Gly Lys Leu Ala Thr Gly Pro Leu Ser Ile Asp Cys Gly
        115                 120                 125

Leu Ala Gly Thr Val Met Arg Phe Val Pro Leu Ala Ala Val Ala
130                 135                 140

Gly Ala Ser Val Ala Phe Asp Gly Asp Glu Ala Ala Arg Val Arg Pro
145                 150                 155                 160

Met Ala Pro Val Leu Asp Ala Leu Glu Thr Leu Gly Ala Arg Ile Glu
                165                 170                 175

Tyr Ala Gly Thr Pro Gly Met Leu Pro Phe Thr Met Asp Ala Ser Ala
            180                 185                 190

Leu Gln Glu Arg His Glu Val Leu Ile Asp Ala Ser Gly Ser Ser Gln
        195                 200                 205

Phe Ile Ser Ala Leu Leu Val Gly Gln Ala Leu Pro Gly Gly Leu
    210                 215                 220

Lys Leu Arg Ala Ala Ala Gly His Ile Ala Ser Pro Asp His Ile Ala
225                 230                 235                 240

Met Thr Val Gln Thr Leu Arg Glu Leu Gly Val Glu Val Ala Val Gly
                245                 250                 255

Glu Asp Ala Arg Ser Trp Ser Ile Ala Pro Gly Gln Leu Ser Gly Phe
            260                 265                 270

Thr Ile Thr Val Glu Pro Asp Leu Ser Asn Ala Gly Pro Phe Leu Ala
        275                 280                 285

Ala Ala Leu Ala Thr Asn Gly Thr Val Arg Val Pro Phe Trp Pro Ala
    290                 295                 300

Ser Thr Thr Gln Val Gly Gly Lys Trp Val Gln Ile Leu Ser Arg Met
305                 310                 315                 320

Gly Ala Glu Ile Ser His Gly Glu Asp Gly Val Leu Thr Val Arg Gly
                325                 330                 335

Thr Gly Val Ile Arg Gly Ile Asp Tyr Ala Asp Ala Ser Glu Leu Ala
            340                 345                 350

Pro Thr Leu Ala Ala Leu Cys Thr Leu Ala Asp Ser Pro Ser Lys Leu
        355                 360                 365

Thr Gly Ile Gly His Leu Arg Gly His Glu Thr Asp Arg Leu Ala Ala
    370                 375                 380

Leu Glu Thr Glu Leu Ala Lys Val Gly Ala Thr Val Thr Ser Thr Asp
385                 390                 395                 400

Asp Ala Leu Glu Ile Ile Pro Gly Thr Leu Gln Ala Ala Asp Leu Asp
                405                 410                 415

Ser Tyr Glu Asp His Arg Met Ala Thr Ala Gly Ala Leu Leu Gly Leu
            420                 425                 430

Ala Ile Glu Gly Val Arg Val Glu Asn Ile Ala Thr Thr Ala Lys Thr
        435                 440                 445

Met Pro Asp Phe Pro Gln Leu Trp Thr Asp Met Ala Ala Thr Ala Lys
    450                 455                 460

Gly Gln Gly
465

<210> SEQ ID NO 3
<211> LENGTH: 1395
<212> TYPE: DNA
<213> ORGANISM: Arthrobacter ramosus
<220> FEATURE:

<221> NAME/KEY: CDS
<222> LOCATION: (1)...(1395)

<400> SEQUENCE: 3

```
atg cca gga acc ccc gcc acg cag aca gac gat tca ggg acg agc aca      48
Met Pro Gly Thr Pro Ala Thr Gln Thr Asp Asp Ser Gly Thr Ser Thr
 1               5                  10                  15 gct tcc gcg ctt ccc ctg tgg ccc gca ccc ttc gcc agc cac cct gtg      96
Ala Ser Ala Leu Pro Leu Trp Pro Ala Pro Phe Ala Ser His Pro Val
             20                  25                  30 gat gcc acg gtc acg gtt cct ggt tcg aag tcg ctg acc aac cgc tat     144
Asp Ala Thr Val Thr Val Pro Gly Ser Lys Ser Leu Thr Asn Arg Tyr
         35                  40                  45 ctg gtc ctg gcg gca ttg gcc aac ggc ccc agc agg ttg cgt gca ccc     192
Leu Val Leu Ala Ala Leu Ala Asn Gly Pro Ser Arg Leu Arg Ala Pro
     50                  55                  60 ttg cat tcg cgc gat tcg gcg ctg atg gtc gag gcc ctg cgc cgg ctt     240
Leu His Ser Arg Asp Ser Ala Leu Met Val Glu Ala Leu Arg Arg Leu
 65                  70                  75                  80 ggc gcc acc att aca gag gtt ccc ggc gat gga cag tac gga ccg gac     288
Gly Ala Thr Ile Thr Glu Val Pro Gly Asp Gly Gln Tyr Gly Pro Asp
                 85                  90                  95 ctt gaa gtc acc ccg atc gac cct gcg gcg gcg gca tcg gag acc gcc     336
Leu Glu Val Thr Pro Ile Asp Pro Ala Ala Ala Ala Ser Glu Thr Ala
            100                 105                 110 atc gac tgc ggc ctg gcc ggc acg gtc atg cgc ttc gtg ccg ccg ctt     384
Ile Asp Cys Gly Leu Ala Gly Thr Val Met Arg Phe Val Pro Pro Leu
        115                 120                 125 gcg gca ctt cgc aac ggc gct tcg gtg ttt gac ggc gat ccg cac gca     432
Ala Ala Leu Arg Asn Gly Ala Ser Val Phe Asp Gly Asp Pro His Ala
    130                 135                 140 cgc cag cgt ccc atg ggc acc atc atc gaa gcc ctc cgg acc ctc gga     480
Arg Gln Arg Pro Met Gly Thr Ile Ile Glu Ala Leu Arg Thr Leu Gly
145                 150                 155                 160 gtg gac gtc agc gcc atg gac ggg aag gcg ccg ggc tcc ttg ccg ttc     528
Val Asp Val Ser Ala Met Asp Gly Lys Ala Pro Gly Ser Leu Pro Phe
                165                 170                 175 aag gtc tcc ggc acg ggc tca gtg cgc ggt ggc cac ttg gtg atc gac     576
Lys Val Ser Gly Thr Gly Ser Val Arg Gly Gly His Leu Val Ile Asp
            180                 185                 190 gcg agc gct tcc tcg cag ttc gtc tcc gcc ctg ctc gtc ggt gcc         624
Ala Ser Ala Ser Ser Gln Phe Val Ser Ala Leu Leu Val Gly Ala
        195                 200                 205 cgt ttc gaa gag ggc ctg cac ctc gag cat gtc ggc aag ccc gtg ccg     672
Arg Phe Glu Glu Gly Leu His Leu Glu His Val Gly Lys Pro Val Pro
    210                 215                 220 agc ctc gac cac atc aac atg act gtg gcg gtc ctg cgc ggg gtt gga     720
Ser Leu Asp His Ile Asn Met Thr Val Ala Val Leu Arg Gly Val Gly
225                 230                 235                 240 gtc cag gta gat gac tcc gtg ccg aac cat tgg cga gtc tcc ccc ggc     768
Val Gln Val Asp Asp Ser Val Pro Asn His Trp Arg Val Ser Pro Gly
                245                 250                 255 gcc atc cag gcg ttc gac gag cga atc gaa cag gac ctc tcc aac gcg     816
Ala Ile Gln Ala Phe Asp Glu Arg Ile Glu Gln Asp Leu Ser Asn Ala
            260                 265                 270 ggt ccc ttc ctc gcc gcg gcg ctc gcc acg aag gga acc gtg cgg atc     864
Gly Pro Phe Leu Ala Ala Ala Leu Ala Thr Lys Gly Thr Val Arg Ile
        275                 280                 285 ccc aac tgg cct gcc agc acc acg caa gtc gga gat ctc tgg cgg aac     912
Pro Asn Trp Pro Ala Ser Thr Thr Gln Val Gly Asp Leu Trp Arg Asn
```

```
att ctt gcc acc atg ggc gct acc gtc acg ctg gac aac ggg acc ctg    960
Ile Leu Ala Thr Met Gly Ala Thr Val Thr Leu Asp Asn Gly Thr Leu
305             310                 315                 320 aca gtc acc ggc ggt tcc gag atc ctg ggc gcg gac ttc gac gaa acg   1008
Thr Val Thr Gly Gly Ser Glu Ile Leu Gly Ala Asp Phe Asp Glu Thr
            325                 330                 335 agc gaa ctc gcc ccc acg gta gcg gca ttg tgc gcc ttg gca acc agc   1056
Ser Glu Leu Ala Pro Thr Val Ala Ala Leu Cys Ala Leu Ala Thr Ser
        340                 345                 350 cct tcc cgg ctc acc ggc atc gcg cac ctg cgc gga cac gag acg gac   1104
Pro Ser Arg Leu Thr Gly Ile Ala His Leu Arg Gly His Glu Thr Asp
    355                 360                 365 agg ctg gcc gcg ctc gtc gcc gaa atc aac cgg ctt ggc ggc gac gcc   1152
Arg Leu Ala Ala Leu Val Ala Glu Ile Asn Arg Leu Gly Gly Asp Ala
370                 375                 380 gag gaa acc agc gac ggc ctg gta atc cgg ccc gca gcg ctg cac tcc   1200
Glu Glu Thr Ser Asp Gly Leu Val Ile Arg Pro Ala Ala Leu His Ser
385             390                 395                 400 ggc gtc gtg cat agc tac gcc gac cac cgc atg gct acg gcg ggc gcc   1248
Gly Val Val His Ser Tyr Ala Asp His Arg Met Ala Thr Ala Gly Ala
            405                 410                 415 atc ctt ggg ctc gcc gtc gag ggt gtc cgg gtc gaa gac atc gcg acg   1296
Ile Leu Gly Leu Ala Val Glu Gly Val Arg Val Glu Asp Ile Ala Thr
        420                 425                 430 acg tcc aag acc atg ccc gaa ttc ccg cag atc tgg acg tcg atg ctc   1344
Thr Ser Lys Thr Met Pro Glu Phe Pro Gln Ile Trp Thr Ser Met Leu
    435                 440                 445 agt gca ggg cca gcg gcc gcg gcc gcc ggt tca acg gag aca agc aac   1392
Ser Ala Gly Pro Ala Ala Ala Ala Ala Gly Ser Thr Glu Thr Ser Asn
450                 455                 460 tga                                                                1395
*
```

<210> SEQ ID NO 4
<211> LENGTH: 464
<212> TYPE: PRT
<213> ORGANISM: Arthrobacter ramosus

<400> SEQUENCE: 4

```
Met Pro Gly Thr Pro Ala Thr Gln Thr Asp Asp Ser Gly Thr Ser Thr
1               5                   10                  15

Ala Ser Ala Leu Pro Leu Trp Pro Ala Pro Phe Ala Ser His Pro Val
            20                  25                  30

Asp Ala Thr Val Thr Val Pro Gly Ser Lys Ser Leu Thr Asn Arg Tyr
        35                  40                  45

Leu Val Leu Ala Ala Leu Ala Asn Gly Pro Ser Arg Leu Arg Ala Pro
    50                  55                  60

Leu His Ser Arg Asp Ser Ala Leu Met Val Glu Ala Leu Arg Arg Leu
65                  70                  75                  80

Gly Ala Thr Ile Thr Glu Val Pro Gly Asp Gly Gln Tyr Gly Pro Asp
                85                  90                  95

Leu Glu Val Thr Pro Ile Asp Pro Ala Ala Ala Ser Glu Thr Ala
            100                 105                 110

Ile Asp Cys Gly Leu Ala Gly Thr Val Met Arg Phe Val Pro Pro Leu
        115                 120                 125

Ala Ala Leu Arg Asn Gly Ala Ser Val Phe Asp Gly Asp Pro His Ala
    130                 135                 140
```

```
Arg Gln Arg Pro Met Gly Thr Ile Ile Glu Ala Leu Arg Thr Leu Gly
145                 150                 155                 160

Val Asp Val Ser Ala Met Asp Gly Lys Ala Pro Gly Ser Leu Pro Phe
            165                 170                 175

Lys Val Ser Gly Thr Gly Ser Val Arg Gly Gly His Leu Val Ile Asp
        180                 185                 190

Ala Ser Ala Ser Ser Gln Phe Val Ser Ala Leu Leu Leu Val Gly Ala
    195                 200                 205

Arg Phe Glu Glu Gly Leu His Leu Glu His Val Gly Lys Pro Val Pro
210                 215                 220

Ser Leu Asp His Ile Asn Met Thr Val Ala Val Leu Arg Gly Val Gly
225                 230                 235                 240

Val Gln Val Asp Asp Ser Val Pro Asn His Trp Arg Val Ser Pro Gly
                245                 250                 255

Ala Ile Gln Ala Phe Asp Glu Arg Ile Glu Gln Asp Leu Ser Asn Ala
            260                 265                 270

Gly Pro Phe Leu Ala Ala Ala Leu Ala Thr Lys Gly Thr Val Arg Ile
        275                 280                 285

Pro Asn Trp Pro Ala Ser Thr Thr Gln Val Gly Asp Leu Trp Arg Asn
290                 295                 300

Ile Leu Ala Thr Met Gly Ala Thr Val Thr Leu Asp Asn Gly Thr Leu
305                 310                 315                 320

Thr Val Thr Gly Gly Ser Glu Ile Leu Gly Ala Asp Phe Asp Glu Thr
                325                 330                 335

Ser Glu Leu Ala Pro Thr Val Ala Leu Cys Ala Leu Ala Thr Ser
            340                 345                 350

Pro Ser Arg Leu Thr Gly Ile Ala His Leu Arg Gly His Glu Thr Asp
        355                 360                 365

Arg Leu Ala Ala Leu Val Ala Glu Ile Asn Arg Leu Gly Gly Asp Ala
370                 375                 380

Glu Glu Thr Ser Asp Gly Leu Val Ile Arg Pro Ala Ala Leu His Ser
385                 390                 395                 400

Gly Val Val His Ser Tyr Ala Asp His Arg Met Ala Thr Ala Gly Ala
                405                 410                 415

Ile Leu Gly Leu Ala Val Glu Gly Val Arg Val Glu Asp Ile Ala Thr
            420                 425                 430

Thr Ser Lys Thr Met Pro Glu Phe Pro Gln Ile Trp Thr Ser Met Leu
        435                 440                 445

Ser Ala Gly Pro Ala Ala Ala Ala Gly Ser Thr Glu Thr Ser Asn
450                 455                 460
```

<210> SEQ ID NO 5
<211> LENGTH: 1368
<212> TYPE: DNA
<213> ORGANISM: Gram positive bacteria
<220> FEATURE:
<221> NAME/KEY: misc_feature
<222> LOCATION: (0)...(0)
<223> OTHER INFORMATION: Gram+ bacteria - strain unknown
<220> FEATURE:
<221> NAME/KEY: CDS
<222> LOCATION: (1)...(1368)

<400> SEQUENCE: 5

```
atg aca ggt acc acc gcc gcc aat acc gaa ccg gac aaa gcc gcc agc      48
Met Thr Gly Thr Thr Ala Ala Asn Thr Glu Pro Asp Lys Ala Ala Ser
1               5                   10                  15
```

|     |     |     |     |     |     |     |     |     |     |     |     |     |     |     |     | |
|-----|-----|-----|-----|-----|-----|-----|-----|-----|-----|-----|-----|-----|-----|-----|-----|-----|
| ctc | ccg | cta | tgg | ccg | gcc | cct | tac | gcc | aat | ggg | cca | gtg | gac | gcc | act | 96 |
| Leu | Pro | Leu | Trp | Pro | Ala | Pro | Tyr | Ala | Asn | Gly | Pro | Val | Asp | Ala | Thr | |
|     |     | 20  |     |     |     | 25  |     |     |     | 30  |     |     |     |     |     | |
| gtg | aca | gtc | ccc | ggt | tca | aaa | tcg | ctg | acc | aac | cgg | ttc | ctg | gtg | ctg | 144 |
| Val | Thr | Val | Pro | Gly | Ser | Lys | Ser | Leu | Thr | Asn | Arg | Phe | Leu | Val | Leu | |
|     |     | 35  |     |     |     | 40  |     |     |     | 45  |     |     |     |     |     | |
| gca | gcc | ttg | gcg | gac | ggt | ccc | tcg | cgg | ctc | cgg | gcc | cca | ctg | cat | tca | 192 |
| Ala | Ala | Leu | Ala | Asp | Gly | Pro | Ser | Arg | Leu | Arg | Ala | Pro | Leu | His | Ser | |
|     | 50  |     |     |     |     | 55  |     |     |     |     | 60  |     |     |     |     | |
| cgc | gat | tct | gcc | ctg | atg | atc | caa | gcc | ctt | cgg | cag | ttg | ggt | gcc | acc | 240 |
| Arg | Asp | Ser | Ala | Leu | Met | Ile | Gln | Ala | Leu | Arg | Gln | Leu | Gly | Ala | Thr | |
| 65  |     |     |     | 70  |     |     |     |     | 75  |     |     |     |     | 80  |     | |
| gtc | acc | gag | gta | ccc | ggt | gac | ggt | gac | tat | ggg | ccc | gac | ctg | gag | atc | 288 |
| Val | Thr | Glu | Val | Pro | Gly | Asp | Gly | Asp | Tyr | Gly | Pro | Asp | Leu | Glu | Ile | |
|     |     |     |     | 85  |     |     |     |     | 90  |     |     |     |     | 95  |     | |
| acg | ccc | ctg | gac | ccc | tcc | gcc | gcg | ggc | tca | agc | acc | gcc | atc | gac | tgc | 336 |
| Thr | Pro | Leu | Asp | Pro | Ser | Ala | Ala | Gly | Ser | Ser | Thr | Ala | Ile | Asp | Cys | |
|     |     |     | 100 |     |     |     |     | 105 |     |     |     |     | 110 |     |     | |
| ggc | ctg | gcg | ggt | acg | gtc | atg | agg | ttc | gtt | ccc | ccg | ctt | gct | gcc | ctg | 384 |
| Gly | Leu | Ala | Gly | Thr | Val | Met | Arg | Phe | Val | Pro | Pro | Leu | Ala | Ala | Leu | |
|     |     | 115 |     |     |     |     | 120 |     |     |     |     | 125 |     |     |     | |
| cgc | agc | ggc | gca | acc | gtc | ttc | gac | ggc | gat | ccc | cat | gcc | cgc | aac | cgt | 432 |
| Arg | Ser | Gly | Ala | Thr | Val | Phe | Asp | Gly | Asp | Pro | His | Ala | Arg | Asn | Arg | |
|     | 130 |     |     |     |     | 135 |     |     |     |     | 140 |     |     |     |     | |
| ccc | atg | gga | acc | atc | atc | gag | gca | ctt | ctt | gcc | ttg | gga | gtc | cct | gtt | 480 |
| Pro | Met | Gly | Thr | Ile | Ile | Glu | Ala | Leu | Leu | Ala | Leu | Gly | Val | Pro | Val | |
| 145 |     |     |     | 150 |     |     |     |     | 155 |     |     |     |     | 160 |     | |
| gca | gcc | gaa | ggc | ggc | agg | acg | ccg | tcg | gcc | ctt | ccc | ttc | acg | gtg | gaa | 528 |
| Ala | Ala | Glu | Gly | Gly | Arg | Thr | Pro | Ser | Ala | Leu | Pro | Phe | Thr | Val | Glu | |
|     |     |     |     | 165 |     |     |     |     | 170 |     |     |     |     | 175 |     | |
| ggc | acc | ggc | gag | gtg | cgc | ggc | ggc | cac | ttg | gtc | atc | gac | gcc | agc | gct | 576 |
| Gly | Thr | Gly | Glu | Val | Arg | Gly | Gly | His | Leu | Val | Ile | Asp | Ala | Ser | Ala | |
|     |     |     | 180 |     |     |     |     | 185 |     |     |     |     | 190 |     |     | |
| tcc | tcc | cag | ttt | gtt | tcg | gca | ttg | ctg | ttg | gtg | ggc | gcc | cgc | ttc | acc | 624 |
| Ser | Ser | Gln | Phe | Val | Ser | Ala | Leu | Leu | Leu | Val | Gly | Ala | Arg | Phe | Thr | |
|     |     | 195 |     |     |     |     | 200 |     |     |     |     | 205 |     |     |     | |
| gaa | ggc | ctg | cac | ttg | gag | cac | gtg | ggc | aaa | ccc | gtt | ccc | agc | ctg | gat | 672 |
| Glu | Gly | Leu | His | Leu | Glu | His | Val | Gly | Lys | Pro | Val | Pro | Ser | Leu | Asp | |
| 210 |     |     |     |     | 215 |     |     |     |     | 220 |     |     |     |     |     | |
| cac | atc | acc | atg | acc | gtt | gag | gtg | ctt | cgg | agc | gtg | ggt | gtc | acc | gtg | 720 |
| His | Ile | Thr | Met | Thr | Val | Glu | Val | Leu | Arg | Ser | Val | Gly | Val | Thr | Val | |
| 225 |     |     |     | 230 |     |     |     |     | 235 |     |     |     |     | 240 |     | |
| gat | gac | tcc | gta | ccc | aac | cac | tgg | cgc | gta | tcg | cct | ggc | aag | atc | acc | 768 |
| Asp | Asp | Ser | Val | Pro | Asn | His | Trp | Arg | Val | Ser | Pro | Gly | Lys | Ile | Thr | |
|     |     |     |     | 245 |     |     |     |     | 250 |     |     |     |     | 255 |     | |
| gct | ttt | gac | cag | cgg | atc | gag | cag | gat | ctc | tcc | aat | gcc | gga | ccc | ttc | 816 |
| Ala | Phe | Asp | Gln | Arg | Ile | Glu | Gln | Asp | Leu | Ser | Asn | Ala | Gly | Pro | Phe | |
|     |     |     | 260 |     |     |     |     | 265 |     |     |     |     | 270 |     |     | |
| ctg | gcc | gcc | gcc | ctg | gcc | act | cat | ggc | act | gtc | cgc | att | ccc | aac | tgg | 864 |
| Leu | Ala | Ala | Ala | Leu | Ala | Thr | His | Gly | Thr | Val | Arg | Ile | Pro | Asn | Trp | |
|     | 275 |     |     |     |     | 280 |     |     |     |     | 285 |     |     |     |     | |
| ccc | att | ggc | acc | acg | cag | gtg | ggc | gat | ctc | tgg | cgg | acc | atc | ctc | gct | 912 |
| Pro | Ile | Gly | Thr | Thr | Gln | Val | Gly | Asp | Leu | Trp | Arg | Thr | Ile | Leu | Ala | |
|     | 290 |     |     |     |     | 295 |     |     |     |     | 300 |     |     |     |     | |
| gcc | atg | ggc | gcg | acc | gtc | acc | ctc | gac | ggg | gga | acg | ctg | aca | gtg | acc | 960 |
| Ala | Met | Gly | Ala | Thr | Val | Thr | Leu | Asp | Gly | Gly | Thr | Leu | Thr | Val | Thr | |
| 305 |     |     |     | 310 |     |     |     |     | 315 |     |     |     |     | 320 |     | |
| ggc | ggg | aat | gag | atc | aag | ggt | gcc | gat | ttc | gac | gaa | acc | agc | gaa | ctc | 1008 |
| Gly | Gly | Asn | Glu | Ile | Lys | Gly | Ala | Asp | Phe | Asp | Glu | Thr | Ser | Glu | Leu | |

```
                   325                 330                 335
gcg ccg acg gta gct gcc ctt tgc gcc ctg gcc acc ggt cca tcg cga    1056
Ala Pro Thr Val Ala Ala Leu Cys Ala Leu Ala Thr Gly Pro Ser Arg
        340                 345                 350 ctg act ggc atc gcc cac ctt cgc gga cac gag acg gat cgc ctc gcc    1104
Leu Thr Gly Ile Ala His Leu Arg Gly His Glu Thr Asp Arg Leu Ala
            355                 360                 365 gcc ctg gtt gcc gag atc aac agg ctt ggt ggt gat gcg gaa gag acc    1152
Ala Leu Val Ala Glu Ile Asn Arg Leu Gly Gly Asp Ala Glu Glu Thr
        370                 375                 380 gca gat gga ctg ctt att cgc ccc gcc acc ctc cac ggc ggc gtg atc    1200
Ala Asp Gly Leu Leu Ile Arg Pro Ala Thr Leu His Gly Gly Val Ile
385                 390                 395                 400 cac agt tac gca gac cac cgg atg gcc act gcc ggc gcc atc ctg ggg    1248
His Ser Tyr Ala Asp His Arg Met Ala Thr Ala Gly Ala Ile Leu Gly
                405                 410                 415 ctc gcc gtt gac ggc gtc cag gtt gaa gac atc gcc acg aca tcc aag    1296
Leu Ala Val Asp Gly Val Gln Val Glu Asp Ile Ala Thr Thr Ser Lys
            420                 425                 430 acc atg ccc gag ttc ccg gag atg tgg gca aga atg ctt gac tcc gcc    1344
Thr Met Pro Glu Phe Pro Glu Met Trp Ala Arg Met Leu Asp Ser Ala
        435                 440                 445 ggc acg aac gag gcc ggc aac tga                                    1368
Gly Thr Asn Glu Ala Gly Asn *
    450                 455

<210> SEQ ID NO 6
<211> LENGTH: 455
<212> TYPE: PRT
<213> ORGANISM: Gram positive bacteria

<400> SEQUENCE: 6

Met Thr Gly Thr Thr Ala Ala Asn Thr Glu Pro Asp Lys Ala Ala Ser
 1               5                  10                  15

Leu Pro Leu Trp Pro Ala Pro Tyr Ala Asn Gly Pro Val Asp Ala Thr
            20                  25                  30

Val Thr Val Pro Gly Ser Lys Ser Leu Thr Asn Arg Phe Leu Val Leu
        35                  40                  45

Ala Ala Leu Ala Asp Gly Pro Ser Arg Leu Arg Ala Pro Leu His Ser
    50                  55                  60

Arg Asp Ser Ala Leu Met Ile Gln Ala Leu Arg Gln Leu Gly Ala Thr
65                  70                  75                  80

Val Thr Glu Val Pro Gly Asp Gly Asp Tyr Gly Pro Asp Leu Glu Ile
                85                  90                  95

Thr Pro Leu Asp Pro Ser Ala Ala Gly Ser Ser Thr Ala Ile Asp Cys
            100                 105                 110

Gly Leu Ala Gly Thr Val Met Arg Phe Val Pro Pro Leu Ala Ala Leu
        115                 120                 125

Arg Ser Gly Ala Thr Val Phe Asp Gly Asp Pro His Ala Arg Asn Arg
    130                 135                 140

Pro Met Gly Thr Ile Ile Glu Ala Leu Leu Ala Leu Gly Val Pro Val
145                 150                 155                 160

Ala Ala Glu Gly Gly Arg Thr Pro Ser Ala Leu Pro Phe Thr Val Glu
                165                 170                 175

Gly Thr Gly Glu Val Arg Gly Gly His Leu Val Ile Asp Ala Ser Ala
            180                 185                 190

Ser Ser Gln Phe Val Ser Ala Leu Leu Leu Val Gly Ala Arg Phe Thr
```

```
                195                 200                 205
Glu Gly Leu His Leu Glu His Val Gly Lys Pro Val Pro Ser Leu Asp
    210                 215                 220

His Ile Thr Met Thr Val Glu Val Leu Arg Ser Val Gly Val Thr Val
225                 230                 235                 240

Asp Asp Ser Val Pro Asn His Trp Arg Val Ser Pro Gly Lys Ile Thr
                245                 250                 255

Ala Phe Asp Gln Arg Ile Glu Gln Asp Leu Ser Asn Ala Gly Pro Phe
            260                 265                 270

Leu Ala Ala Ala Leu Ala Thr His Gly Thr Val Arg Ile Pro Asn Trp
        275                 280                 285

Pro Ile Gly Thr Thr Gln Val Gly Asp Leu Trp Arg Thr Ile Leu Ala
    290                 295                 300

Ala Met Gly Ala Thr Val Thr Leu Asp Gly Gly Thr Leu Thr Val Thr
305                 310                 315                 320

Gly Gly Asn Glu Ile Lys Gly Ala Asp Phe Asp Glu Thr Ser Glu Leu
                325                 330                 335

Ala Pro Thr Val Ala Ala Leu Cys Ala Leu Ala Thr Gly Pro Ser Arg
            340                 345                 350

Leu Thr Gly Ile Ala His Leu Arg Gly His Glu Thr Asp Arg Leu Ala
        355                 360                 365

Ala Leu Val Ala Glu Ile Asn Arg Leu Gly Gly Asp Ala Glu Thr
370                 375                 380

Ala Asp Gly Leu Leu Ile Arg Pro Ala Thr Leu His Gly Gly Val Ile
385                 390                 395                 400

His Ser Tyr Ala Asp His Arg Met Ala Thr Ala Gly Ala Ile Leu Gly
                405                 410                 415

Leu Ala Val Asp Gly Val Gln Val Glu Asp Ile Ala Thr Thr Ser Lys
            420                 425                 430

Thr Met Pro Glu Phe Pro Glu Met Trp Ala Arg Met Leu Asp Ser Ala
        435                 440                 445

Gly Thr Asn Glu Ala Gly Asn
    450                 455

<210> SEQ ID NO 7
<211> LENGTH: 1386
<212> TYPE: DNA
<213> ORGANISM: Arthrobacter ureafaciens
<220> FEATURE:
<221> NAME/KEY: CDS
<222> LOCATION: (1)...(1386)

<400> SEQUENCE: 7 atg aca ggt acc acc gca gca aac acg ggt tca aac tcc gtc gac acc      48
Met Thr Gly Thr Thr Ala Ala Asn Thr Gly Ser Asn Ser Val Asp Thr
 1               5                  10                  15 ctg ccc ctc tgg gca gct ccc tac gcc acc agg cca gtg gat gcc aca      96
Leu Pro Leu Trp Ala Ala Pro Tyr Ala Thr Arg Pro Val Asp Ala Thr
             20                  25                  30 gtg acg gtg ccg ggc tca aaa tcg ctc acc aac cgt ttc ctg gtc ctc     144
Val Thr Val Pro Gly Ser Lys Ser Leu Thr Asn Arg Phe Leu Val Leu
         35                  40                  45 gca gca ttg gcc gac ggc cct tcc cgc ctg cgg gcc ccc ctt cac tcc     192
Ala Ala Leu Ala Asp Gly Pro Ser Arg Leu Arg Ala Pro Leu His Ser
     50                  55                  60 cgc gat tcc gtc ctt atg att cag gcg ctc aga caa ctg ggt gcc acc     240
Arg Asp Ser Val Leu Met Ile Gln Ala Leu Arg Gln Leu Gly Ala Thr
 65                  70                  75                  80
```

```
                65                  70                  75                  80
gtc acc gag gta ccc ggc gac ggt gat tat gga ccg gac ctt gag atc          288
Val Thr Glu Val Pro Gly Asp Gly Asp Tyr Gly Pro Asp Leu Glu Ile
                    85                  90                  95 act ccc atg gat cct tcg gct tcg ggt gcg gag act gcc atc gat tgc          336
Thr Pro Met Asp Pro Ser Ala Ser Gly Ala Glu Thr Ala Ile Asp Cys
            100                 105                 110 ggc ctt gcc ggt acg gtt atg cgc ttc gtt cca cct tta gct gcg cta          384
Gly Leu Ala Gly Thr Val Met Arg Phe Val Pro Pro Leu Ala Ala Leu
        115                 120                 125 cgc aat ggt cca acc acg ttc gac ggc gat ccc cat gcc cgt aag cgg          432
Arg Asn Gly Pro Thr Thr Phe Asp Gly Asp Pro His Ala Arg Lys Arg
    130                 135                 140 ccc atg gga acc atc atc gaa gcg ctg ctc gcc ctc gga gtt cct gtc          480
Pro Met Gly Thr Ile Ile Glu Ala Leu Leu Ala Leu Gly Val Pro Val
145                 150                 155                 160 gcc acc gaa ggc gga agg acg ccg tcg gcc ctt ccc ttc tct gtg gat          528
Ala Thr Glu Gly Gly Arg Thr Pro Ser Ala Leu Pro Phe Ser Val Asp
                165                 170                 175 ggc act ggc gag gtt cgg ggc ggc cat ctg gtg atc gat gcc agc gca          576
Gly Thr Gly Glu Val Arg Gly Gly His Leu Val Ile Asp Ala Ser Ala
            180                 185                 190 tcg tcc cag ttc gtt tcg gcc ttg ctg ctt gta ggc gcc aga ttc acc          624
Ser Ser Gln Phe Val Ser Ala Leu Leu Leu Val Gly Ala Arg Phe Thr
        195                 200                 205 gaa ggc ctt cac ctg gaa cac gtt ggc aag cct gtc ccc agc ctg gac          672
Glu Gly Leu His Leu Glu His Val Gly Lys Pro Val Pro Ser Leu Asp
    210                 215                 220 cac atc aat atg acc gtt tcc gtc ctt cgc gga gtg ggc gtc aag gtg          720
His Ile Asn Met Thr Val Ser Val Leu Arg Gly Val Gly Val Lys Val
225                 230                 235                 240 gac gat tcg gta ccc aac cac tgg cgg gtc gca cct ggc ccc atc cac          768
Asp Asp Ser Val Pro Asn His Trp Arg Val Ala Pro Gly Pro Ile His
                245                 250                 255 gcc ttc gac cag cgg atc gaa cag gac ctt tcc aac gcc ggc ccg ttc          816
Ala Phe Asp Gln Arg Ile Glu Gln Asp Leu Ser Asn Ala Gly Pro Phe
            260                 265                 270 ctt gcc gca gcc ctg gca acc cgc gga acc gtc cgg atc ccc aac tgg          864
Leu Ala Ala Ala Leu Ala Thr Arg Gly Thr Val Arg Ile Pro Asn Trp
        275                 280                 285 ccc acc cag acc acc cag gtg ggt gat ctt tgg cgg tcc atc ctg gtt          912
Pro Thr Gln Thr Thr Gln Val Gly Asp Leu Trp Arg Ser Ile Leu Val
    290                 295                 300 gag atg ggt gcc acg gtg aca ctc gaa aac ggc acg ctc acg gtt aag          960
Glu Met Gly Ala Thr Val Thr Leu Glu Asn Gly Thr Leu Thr Val Lys
305                 310                 315                 320 ggc ggc ccg gaa atc aaa ggc gcc gac ttc gac gaa acc agc gag ctc         1008
Gly Gly Pro Glu Ile Lys Gly Ala Asp Phe Asp Glu Thr Ser Glu Leu
                325                 330                 335 gcg ccc acg gtc gct gcg ctg tgc gca ctg gcc aca ggc cct tca cgg         1056
Ala Pro Thr Val Ala Ala Leu Cys Ala Leu Ala Thr Gly Pro Ser Arg
            340                 345                 350 ctg acc ggc atc gcg cac ctc cgt ggc cat gaa acc gat cgg ctc gcc         1104
Leu Thr Gly Ile Ala His Leu Arg Gly His Glu Thr Asp Arg Leu Ala
        355                 360                 365 gcg ctg gcc gct gaa atc aat cgg ctc ggc gga gac gca gaa gaa aca         1152
Ala Leu Ala Ala Glu Ile Asn Arg Leu Gly Gly Asp Ala Glu Glu Thr
    370                 375                 380 gct gac ggc ctg atc atc cgc ccg gcc act ctg cat ccc ggc gtc gta         1200
```

```
Ala Asp Gly Leu Ile Ile Arg Pro Ala Thr Leu His Pro Gly Val Val
385                 390                 395                 400 cac agc tac gcc gac cac cgc atg gct acg gcc ggc gct att ttg ggg    1248
His Ser Tyr Ala Asp His Arg Met Ala Thr Ala Gly Ala Ile Leu Gly
                405                 410                 415 ctc gcc gtt gag ggc gtc cag gtg gag gat atc gct acc acc tcc aag    1296
Leu Ala Val Glu Gly Val Gln Val Glu Asp Ile Ala Thr Thr Ser Lys
            420                 425                 430 acg gtg ccc gaa ttt ccg cag atg tgg gag gcc atg ctg cag cag ggc    1344
Thr Val Pro Glu Phe Pro Gln Met Trp Glu Ala Met Leu Gln Gln Gly
        435                 440                 445 acg ggc gag gac gaa acc gtc acc agt gag gcc agc aac tga             1386
Thr Gly Glu Asp Glu Thr Val Thr Ser Glu Ala Ser Asn *
    450                 455                 460

<210> SEQ ID NO 8
<211> LENGTH: 461
<212> TYPE: PRT
<213> ORGANISM: Arthrobacter ureafaciens

<400> SEQUENCE: 8

Met Thr Gly Thr Thr Ala Ala Asn Thr Gly Ser Asn Ser Val Asp Thr
1               5                   10                  15

Leu Pro Leu Trp Ala Ala Pro Tyr Ala Thr Arg Pro Val Asp Ala Thr
            20                  25                  30

Val Thr Val Pro Gly Ser Lys Ser Leu Thr Asn Arg Phe Leu Val Leu
        35                  40                  45

Ala Ala Leu Ala Asp Gly Pro Ser Arg Leu Arg Ala Pro Leu His Ser
    50                  55                  60

Arg Asp Ser Val Leu Met Ile Gln Ala Leu Arg Gln Leu Gly Ala Thr
65                  70                  75                  80

Val Thr Glu Val Pro Gly Asp Gly Asp Tyr Gly Pro Asp Leu Glu Ile
                85                  90                  95

Thr Pro Met Asp Pro Ser Ala Ser Gly Ala Glu Thr Ala Ile Asp Cys
            100                 105                 110

Gly Leu Ala Gly Thr Val Met Arg Phe Val Pro Pro Leu Ala Ala Leu
        115                 120                 125

Arg Asn Gly Pro Thr Thr Phe Asp Gly Asp Pro His Ala Arg Lys Arg
    130                 135                 140

Pro Met Gly Thr Ile Ile Glu Ala Leu Leu Ala Leu Gly Val Pro Val
145                 150                 155                 160

Ala Thr Glu Gly Gly Arg Thr Pro Ser Ala Leu Pro Phe Ser Val Asp
                165                 170                 175

Gly Thr Gly Glu Val Arg Gly Gly His Leu Val Ile Asp Ala Ser Ala
            180                 185                 190

Ser Ser Gln Phe Val Ser Ala Leu Leu Leu Val Gly Ala Arg Phe Thr
        195                 200                 205

Glu Gly Leu His Leu Glu His Val Gly Lys Pro Val Pro Ser Leu Asp
    210                 215                 220

His Ile Asn Met Thr Val Ser Val Leu Arg Gly Val Gly Val Lys Val
225                 230                 235                 240

Asp Asp Ser Val Pro Asn His Trp Arg Val Ala Pro Gly Pro Ile His
                245                 250                 255

Ala Phe Asp Gln Arg Ile Glu Gln Asp Leu Ser Asn Ala Gly Pro Phe
            260                 265                 270

Leu Ala Ala Ala Leu Ala Thr Arg Gly Thr Val Arg Ile Pro Asn Trp
```

-continued

```
                    275                 280                 285
Pro Thr Gln Thr Thr Gln Val Gly Asp Leu Trp Arg Ser Ile Leu Val
    290                 295                 300

Glu Met Gly Ala Thr Val Thr Leu Glu Asn Gly Thr Leu Thr Val Lys
305                 310                 315                 320

Gly Gly Pro Glu Ile Lys Gly Ala Asp Phe Asp Glu Thr Ser Glu Leu
                325                 330                 335

Ala Pro Thr Val Ala Ala Leu Cys Ala Leu Ala Thr Gly Pro Ser Arg
            340                 345                 350

Leu Thr Gly Ile Ala His Leu Arg Gly His Glu Thr Asp Arg Leu Ala
        355                 360                 365

Ala Leu Ala Ala Glu Ile Asn Arg Leu Gly Gly Asp Ala Glu Glu Thr
370                 375                 380

Ala Asp Gly Leu Ile Ile Arg Pro Ala Thr Leu His Pro Gly Val Val
385                 390                 395                 400

His Ser Tyr Ala Asp His Arg Met Ala Thr Gly Ala Ile Leu Gly
                405                 410                 415

Leu Ala Val Glu Gly Val Gln Val Glu Asp Ile Ala Thr Thr Ser Lys
            420                 425                 430

Thr Val Pro Glu Phe Pro Gln Met Trp Glu Ala Met Leu Gln Gln Gly
        435                 440                 445

Thr Gly Glu Asp Glu Thr Val Thr Ser Glu Ala Ser Asn
    450                 455                 460

<210> SEQ ID NO 9
<211> LENGTH: 1296
<212> TYPE: DNA
<213> ORGANISM: Paenibacillus pabuli
<220> FEATURE:
<221> NAME/KEY: CDS
<222> LOCATION: (1)...(1296)

<400> SEQUENCE: 9 atg gac gtt atc gtt aaa cca acc cca tcc ctg aac ggg gaa att gga    48
Met Asp Val Ile Val Lys Pro Thr Pro Ser Leu Asn Gly Glu Ile Gly
1               5                  10                  15 gct ttg tct tcc aag aac tac acc aca cgc tac ttg cta gct gct gcg    96
Ala Leu Ser Ser Lys Asn Tyr Thr Thr Arg Tyr Leu Leu Ala Ala Ala
                20                  25                  30 ctg gca gaa ggc aca agt acg att cat tac cct gct cac agt gaa gat    144
Leu Ala Glu Gly Thr Ser Thr Ile His Tyr Pro Ala His Ser Glu Asp
            35                  40                  45 agt gac gct atg cgc aga tgt att agt gat ctt gga gcg gtg ctc gaa    192
Ser Asp Ala Met Arg Arg Cys Ile Ser Asp Leu Gly Ala Val Leu Glu
        50                  55                  60 gaa gat gat agc aaa atc gtt att cag ggc ttc ggc agc cat cca cgt    240
Glu Asp Asp Ser Lys Ile Val Ile Gln Gly Phe Gly Ser His Pro Arg
65                  70                  75                  80 gat gtg cgt gaa tta aat gta ggc aat gcg ggt gca gtg ctg cgt ttc    288
Asp Val Arg Glu Leu Asn Val Gly Asn Ala Gly Ala Val Leu Arg Phe
                85                  90                  95 ctg atg ggg gta acg gca ctt tgt cct gat gtt acg ttt gta aat acg    336
Leu Met Gly Val Thr Ala Leu Cys Pro Asp Val Thr Phe Val Asn Thr
                100                 105                 110 tac ccg gat tct ctg ggc aaa cgc cca cat gat gac ctg atc gat gcg    384
Tyr Pro Asp Ser Leu Gly Lys Arg Pro His Asp Asp Leu Ile Asp Ala
            115                 120                 125 ctt ggt cag ctt ggt gtt gag gta caa cac gaa caa gga cgc ttg cca    432
```

|     |     |     |     |     |     |     |     |     |     |     |     |     |     |     |      |
|-----|-----|-----|-----|-----|-----|-----|-----|-----|-----|-----|-----|-----|-----|-----|------|
| Leu | Gly | Gln | Leu | Gly | Val | Glu | Val | Gln | His | Glu | Gln | Gly | Arg | Leu | Pro  |
|     | 130 |     |     |     | 135 |     |     |     | 140 |     |     |     |     |     |      |

```
atc acg atc aaa ggg ggt cag gcc aag ggt gga cat atc cgt gta tcc      480
Ile Thr Ile Lys Gly Gly Gln Ala Lys Gly Gly His Ile Arg Val Ser
145                 150                 155                 160 ggt tcg gtc agc tct cag tat ttg agc gcg tta ctg ttt gta act cct      528
Gly Ser Val Ser Ser Gln Tyr Leu Ser Ala Leu Leu Phe Val Thr Pro
                165                 170                 175 ctt ctg gcc gaa gac agc acg att gaa gta tta aac gac ttg aaa tcc      576
Leu Leu Ala Glu Asp Ser Thr Ile Glu Val Leu Asn Asp Leu Lys Ser
            180                 185                 190 aaa gtg gtt att ggc cag acg ctg gaa gta ttg gaa cag gcg ggc atc      624
Lys Val Val Ile Gly Gln Thr Leu Glu Val Leu Glu Gln Ala Gly Ile
        195                 200                 205 gtc att cat gcg agt gat gat tac atg tcc ttc cgc gta cct ggc ggt      672
Val Ile His Ala Ser Asp Asp Tyr Met Ser Phe Arg Val Pro Gly Gly
    210                 215                 220 caa gcc tat aaa cca caa aca tat acg gtt caa gga gac tat ccg ggt      720
Gln Ala Tyr Lys Pro Gln Thr Tyr Thr Val Gln Gly Asp Tyr Pro Gly
225                 230                 235                 240 tca gca gct gtc ctc gcg gcc gcg gct gtc acc caa tcg gat gtt aaa      768
Ser Ala Ala Val Leu Ala Ala Ala Ala Val Thr Gln Ser Asp Val Lys
                245                 250                 255 att ttg cga ttg atg gaa cag agc aaa caa ggt gag cgt gcc att gta      816
Ile Leu Arg Leu Met Glu Gln Ser Lys Gln Gly Glu Arg Ala Ile Val
            260                 265                 270 gac gtt ctg cgc atg atg gaa gtg ccg ttg acg cat gaa aac gat gtg      864
Asp Val Leu Arg Met Met Glu Val Pro Leu Thr His Glu Asn Asp Val
        275                 280                 285 gta cac gtg caa ggt aac ggt aca ttg aaa gcc gtg gaa ttc gat gga      912
Val His Val Gln Gly Asn Gly Thr Leu Lys Ala Val Glu Phe Asp Gly
    290                 295                 300 gat gcc gcg aca gac gcg gtt ttg gcc atg gta gcg gcg gca gtg ttt      960
Asp Ala Ala Thr Asp Ala Val Leu Ala Met Val Ala Ala Ala Val Phe
305                 310                 315                 320 gcg gaa ggc acc tca cgg ttc tat aat gta gag aac tta cgt tac aag     1008
Ala Glu Gly Thr Ser Arg Phe Tyr Asn Val Glu Asn Leu Arg Tyr Lys
                325                 330                 335 gaa tgt gac cga att aca gat tat ttg aac gaa ctg cgg aag gca gga     1056
Glu Cys Asp Arg Ile Thr Asp Tyr Leu Asn Glu Leu Arg Lys Ala Gly
            340                 345                 350 gcc aac gta gaa gaa cgt cag gcc gag att atc gta cat ggt cgt ccg     1104
Ala Asn Val Glu Glu Arg Gln Ala Glu Ile Ile Val His Gly Arg Pro
        355                 360                 365 gaa ggc gtc gaa ggc ggc gtt gag att aac gct cac tac gat cat cgc     1152
Glu Gly Val Glu Gly Gly Val Glu Ile Asn Ala His Tyr Asp His Arg
    370                 375                 380 gta att atg gca ctg acc gtt gtc ggt ctg cgt tcc aaa gaa ccg ctt     1200
Val Ile Met Ala Leu Thr Val Val Gly Leu Arg Ser Lys Glu Pro Leu
385                 390                 395                 400 cgt att cgg gat gca cac cat gta gcc aag tct tat ccg caa tat ttc     1248
Arg Ile Arg Asp Ala His His Val Ala Lys Ser Tyr Pro Gln Tyr Phe
                405                 410                 415 gat cat ttg cag gcg ctt ggc gcc tcg gtt caa tgg gta aaa gag taa     1296
Asp His Leu Gln Ala Leu Gly Ala Ser Val Gln Trp Val Lys Glu *
            420                 425                 430

<210> SEQ ID NO 10
<211> LENGTH: 431
<212> TYPE: PRT
```

<213> ORGANISM: Paenibacillus pabuli

<400> SEQUENCE: 10

```
Met Asp Val Ile Val Lys Pro Thr Pro Ser Leu Asn Gly Glu Ile Gly
 1               5                  10                  15

Ala Leu Ser Ser Lys Asn Tyr Thr Thr Arg Tyr Leu Leu Ala Ala Ala
            20                  25                  30

Leu Ala Glu Gly Thr Ser Thr Ile His Tyr Pro Ala His Ser Glu Asp
        35                  40                  45

Ser Asp Ala Met Arg Arg Cys Ile Ser Asp Leu Gly Ala Val Leu Glu
    50                  55                  60

Glu Asp Asp Ser Lys Ile Val Ile Gln Gly Phe Gly Ser His Pro Arg
65                  70                  75                  80

Asp Val Arg Glu Leu Asn Val Gly Asn Ala Gly Ala Val Leu Arg Phe
                85                  90                  95

Leu Met Gly Val Thr Ala Leu Cys Pro Asp Val Thr Phe Val Asn Thr
            100                 105                 110

Tyr Pro Asp Ser Leu Gly Lys Arg Pro His Asp Asp Leu Ile Asp Ala
        115                 120                 125

Leu Gly Gln Leu Gly Val Glu Val Gln His Glu Gln Gly Arg Leu Pro
    130                 135                 140

Ile Thr Ile Lys Gly Gly Gln Ala Lys Gly Gly His Ile Arg Val Ser
145                 150                 155                 160

Gly Ser Val Ser Ser Gln Tyr Leu Ser Ala Leu Leu Phe Val Thr Pro
                165                 170                 175

Leu Leu Ala Glu Asp Ser Thr Ile Glu Val Leu Asn Asp Leu Lys Ser
            180                 185                 190

Lys Val Val Ile Gly Gln Thr Leu Glu Val Leu Glu Gln Ala Gly Ile
        195                 200                 205

Val Ile His Ala Ser Asp Asp Tyr Met Ser Phe Arg Val Pro Gly Gly
    210                 215                 220

Gln Ala Tyr Lys Pro Gln Thr Tyr Thr Val Gln Gly Asp Tyr Pro Gly
225                 230                 235                 240

Ser Ala Ala Val Leu Ala Ala Ala Val Thr Gln Ser Asp Val Lys
                245                 250                 255

Ile Leu Arg Leu Met Glu Gln Ser Lys Gln Gly Glu Arg Ala Ile Val
            260                 265                 270

Asp Val Leu Arg Met Met Glu Val Pro Leu Thr His Glu Asn Asp Val
        275                 280                 285

Val His Val Gln Gly Asn Gly Thr Leu Lys Ala Val Glu Phe Asp Gly
    290                 295                 300

Asp Ala Ala Thr Asp Ala Val Leu Ala Met Val Ala Ala Val Phe
305                 310                 315                 320

Ala Glu Gly Thr Ser Arg Phe Tyr Asn Val Glu Asn Leu Arg Tyr Lys
                325                 330                 335

Glu Cys Asp Arg Ile Thr Asp Tyr Leu Asn Glu Leu Arg Lys Ala Gly
            340                 345                 350

Ala Asn Val Glu Glu Arg Gln Ala Glu Ile Ile Val His Gly Arg Pro
        355                 360                 365

Glu Gly Val Glu Gly Gly Val Glu Ile Asn Ala His Tyr Asp His Arg
    370                 375                 380

Val Ile Met Ala Leu Thr Val Val Gly Leu Arg Ser Lys Glu Pro Leu
385                 390                 395                 400
```

```
Arg Ile Arg Asp Ala His His Val Ala Lys Ser Tyr Pro Gln Tyr Phe
            405                 410                 415

Asp His Leu Gln Ala Leu Gly Ala Ser Val Gln Trp Val Lys Glu
        420                 425                 430

<210> SEQ ID NO 11
<211> LENGTH: 1296
<212> TYPE: DNA
<213> ORGANISM: Paenibacillus pabuli
<220> FEATURE:
<221> NAME/KEY: CDS
<222> LOCATION: (1)...(1296)

<400> SEQUENCE: 11 atg gac gtt atc gtt aaa ccg acc cca tcc ctg aac gga gaa att gga      48
Met Asp Val Ile Val Lys Pro Thr Pro Ser Leu Asn Gly Glu Ile Gly
 1               5                  10                  15 gct ttg tct tcc aaa aac tac acc aca cgc tac ttg cta gct gct gct      96
Ala Leu Ser Ser Lys Asn Tyr Thr Thr Arg Tyr Leu Leu Ala Ala Ala
             20                  25                  30 ctg gca gaa ggc acg agt acg atc cat tac ccg gct cac agt gaa gat     144
Leu Ala Glu Gly Thr Ser Thr Ile His Tyr Pro Ala His Ser Glu Asp
         35                  40                  45 agt gac gct atg cgc aga tgt att cgc gat ctt gga gca gtg ctt gaa     192
Ser Asp Ala Met Arg Arg Cys Ile Arg Asp Leu Gly Ala Val Leu Glu
     50                  55                  60 gaa gat gac agc aaa att gtt atc cag ggc ttt ggc agc cat cca cat     240
Glu Asp Asp Ser Lys Ile Val Ile Gln Gly Phe Gly Ser His Pro His
 65                  70                  75                  80 gat gtg cgt gaa tta aat gta ggc aat gcg ggt gca gtg ctg cgt ttc     288
Asp Val Arg Glu Leu Asn Val Gly Asn Ala Gly Ala Val Leu Arg Phe
                 85                  90                  95 cta atg ggg gta aca gca ctt tgt cct gag gtg acg ttt gta aat acg     336
Leu Met Gly Val Thr Ala Leu Cys Pro Glu Val Thr Phe Val Asn Thr
            100                 105                 110 tac ccg gat tct ctt ggc aaa cgc cca cat gat gac ctg atc gat gcg     384
Tyr Pro Asp Ser Leu Gly Lys Arg Pro His Asp Asp Leu Ile Asp Ala
        115                 120                 125 ctt ggt cag ctc ggt gtt gag gta cag cac gaa caa gga cgc ttg cca     432
Leu Gly Gln Leu Gly Val Glu Val Gln His Glu Gln Gly Arg Leu Pro
    130                 135                 140 atc acg atc aaa ggt ggt cag gct aag ggt gga cat atc cgt gta tcc     480
Ile Thr Ile Lys Gly Gly Gln Ala Lys Gly Gly His Ile Arg Val Ser
145                 150                 155                 160 ggt tct gtc agc tcc cag tat ttg agc gcg ttg ctg ttt gta act ccg     528
Gly Ser Val Ser Ser Gln Tyr Leu Ser Ala Leu Leu Phe Val Thr Pro
                165                 170                 175 ctt ctg gcc gaa gac agc aca att gaa gta ttg aat gac ttg aaa tcc     576
Leu Leu Ala Glu Asp Ser Thr Ile Glu Val Leu Asn Asp Leu Lys Ser
            180                 185                 190 aaa gtg gtt att ggt cag acg ctg gaa gta ctg gaa caa gcg ggt atc     624
Lys Val Val Ile Gly Gln Thr Leu Glu Val Leu Glu Gln Ala Gly Ile
        195                 200                 205 gtc att cat gcg agt gat gat tac atg tcc ttc cgc gta cct ggc ggc     672
Val Ile His Ala Ser Asp Asp Tyr Met Ser Phe Arg Val Pro Gly Gly
    210                 215                 220 caa gcc tat aaa ccg caa aca tat acg gtt caa gga gac tat ccg ggt     720
Gln Ala Tyr Lys Pro Gln Thr Tyr Thr Val Gln Gly Asp Tyr Pro Gly
225                 230                 235                 240 tca gca gct gtc ctc gcg gct gcg gcg gtc act caa tcc gat gtt aaa     768
Ser Ala Ala Val Leu Ala Ala Ala Ala Val Thr Gln Ser Asp Val Lys
```

```
att ttg cga ttg atg gaa cag agc aaa caa ggt gag cgt gct att gtt       816
Ile Leu Arg Leu Met Glu Gln Ser Lys Gln Gly Glu Arg Ala Ile Val
            260                 265                 270 gac gtt ctg cgc atg atg gaa gtg ccg ttg acg cat gag aac gat gtg       864
Asp Val Leu Arg Met Met Glu Val Pro Leu Thr His Glu Asn Asp Val
        275                 280                 285 gtt cac gtg caa ggt aac ggt act ttg aaa gcc gtg gaa ttc gat gga       912
Val His Val Gln Gly Asn Gly Thr Leu Lys Ala Val Glu Phe Asp Gly
    290                 295                 300 gat gcc gcg aca gac gcg gtt ttg gcc atg gta gcg gca gtg ttt           960
Asp Ala Ala Thr Asp Ala Val Leu Ala Met Val Ala Ala Val Phe
305                 310                 315                 320 gcg gaa ggc acc tca cgg ttc tat aat gta gag aac tta cgt tac aag      1008
Ala Glu Gly Thr Ser Arg Phe Tyr Asn Val Glu Asn Leu Arg Tyr Lys
                325                 330                 335 gaa tgt gac cga att acg gat tat ttg aac gaa ctg cgg aag gca gga      1056
Glu Cys Asp Arg Ile Thr Asp Tyr Leu Asn Glu Leu Arg Lys Ala Gly
            340                 345                 350 gcc aac gta gaa gaa cgt cag gcc gag att atc gta cat ggt cgt ccg      1104
Ala Asn Val Glu Glu Arg Gln Ala Glu Ile Ile Val His Gly Arg Pro
        355                 360                 365 gaa ggc gtc gaa ggc ggc gtt gag att aac gct cac tac gat cat cgc      1152
Glu Gly Val Glu Gly Gly Val Glu Ile Asn Ala His Tyr Asp His Arg
    370                 375                 380 gta att atg gca ctg acc gtt gtc ggt ctg cgt tcc aaa gaa ccg ctt      1200
Val Ile Met Ala Leu Thr Val Val Gly Leu Arg Ser Lys Glu Pro Leu
385                 390                 395                 400 cgt atc cgg gat gca cac cat gta gcc aag tct tat ccg caa tat ttc      1248
Arg Ile Arg Asp Ala His His Val Ala Lys Ser Tyr Pro Gln Tyr Phe
                405                 410                 415 gat cat ttg cag gcg ctt ggc gcc tcg gtt caa tgg gta aaa gag taa      1296
Asp His Leu Gln Ala Leu Gly Ala Ser Val Gln Trp Val Lys Glu *
            420                 425                 430

<210> SEQ ID NO 12
<211> LENGTH: 431
<212> TYPE: PRT
<213> ORGANISM: Paenibacillus pabuli

<400> SEQUENCE: 12

Met Asp Val Ile Val Lys Pro Thr Pro Ser Leu Asn Gly Glu Ile Gly
1               5                   10                  15

Ala Leu Ser Ser Lys Asn Tyr Thr Thr Arg Tyr Leu Leu Ala Ala Ala
            20                  25                  30

Leu Ala Glu Gly Thr Ser Thr Ile His Tyr Pro Ala His Ser Glu Asp
        35                  40                  45

Ser Asp Ala Met Arg Arg Cys Ile Arg Asp Leu Gly Ala Val Leu Glu
    50                  55                  60

Glu Asp Ser Lys Ile Val Ile Gln Gly Phe Gly Ser His Pro His
65                  70                  75                  80

Asp Val Arg Glu Leu Asn Val Gly Asn Ala Gly Ala Val Leu Arg Phe
                85                  90                  95

Leu Met Gly Val Thr Ala Leu Cys Pro Glu Val Thr Phe Val Asn Thr
            100                 105                 110

Tyr Pro Asp Ser Leu Gly Lys Arg Pro His Asp Asp Leu Ile Asp Ala
        115                 120                 125

Leu Gly Gln Leu Gly Val Glu Val Gln His Glu Gln Gly Arg Leu Pro
```

```
              130                 135                 140
Ile Thr Ile Lys Gly Gly Gln Ala Lys Gly Gly His Ile Arg Val Ser
145                 150                 155                 160

Gly Ser Val Ser Ser Gln Tyr Leu Ser Ala Leu Leu Phe Val Thr Pro
                165                 170                 175

Leu Leu Ala Glu Asp Ser Thr Ile Glu Val Leu Asn Asp Leu Lys Ser
            180                 185                 190

Lys Val Val Ile Gly Gln Thr Leu Glu Val Leu Glu Gln Ala Gly Ile
                195                 200                 205

Val Ile His Ala Ser Asp Asp Tyr Met Ser Phe Arg Val Pro Gly Gly
210                 215                 220

Gln Ala Tyr Lys Pro Gln Thr Tyr Thr Val Gln Gly Asp Tyr Pro Gly
225                 230                 235                 240

Ser Ala Ala Val Leu Ala Ala Ala Val Thr Gln Ser Asp Val Lys
                245                 250                 255

Ile Leu Arg Leu Met Glu Gln Ser Lys Gln Gly Glu Arg Ala Ile Val
                260                 265                 270

Asp Val Leu Arg Met Met Glu Val Pro Leu Thr His Glu Asn Asp Val
            275                 280                 285

Val His Val Gln Gly Asn Gly Thr Leu Lys Ala Val Glu Phe Asp Gly
290                 295                 300

Asp Ala Ala Thr Asp Ala Val Leu Ala Met Val Ala Ala Val Phe
305                 310                 315                 320

Ala Glu Gly Thr Ser Arg Phe Tyr Asn Val Glu Asn Leu Arg Tyr Lys
                325                 330                 335

Glu Cys Asp Arg Ile Thr Asp Tyr Leu Asn Glu Leu Arg Lys Ala Gly
                340                 345                 350

Ala Asn Val Glu Glu Arg Gln Ala Glu Ile Ile Val His Gly Arg Pro
                355                 360                 365

Glu Gly Val Glu Gly Val Glu Ile Asn Ala His Tyr Asp His Arg
            370                 375                 380

Val Ile Met Ala Leu Thr Val Val Gly Leu Arg Ser Lys Glu Pro Leu
385                 390                 395                 400

Arg Ile Arg Asp Ala His His Val Ala Lys Ser Tyr Pro Gln Tyr Phe
                405                 410                 415

Asp His Leu Gln Ala Leu Gly Ala Ser Val Gln Trp Val Lys Glu
                420                 425                 430

<210> SEQ ID NO 13
<211> LENGTH: 1251
<212> TYPE: DNA
<213> ORGANISM: Sphingobacterium multivorum/faecium
<220> FEATURE:
<221> NAME/KEY: CDS
<222> LOCATION: (1)...(1251)

<400> SEQUENCE: 13 atg aat caa caa gtc atc acg ctg acg cat cct tca aaa aaa ata cag      48
Met Asn Gln Gln Val Ile Thr Leu Thr His Pro Ser Lys Lys Ile Gln
 1               5                  10                  15 ggt acg gtt caa ctc aca ggt tca aaa tct gag agc aac cgt gct ctt      96
Gly Thr Val Gln Leu Thr Gly Ser Lys Ser Glu Ser Asn Arg Ala Leu
             20                  25                  30 att atc cag tca ttg agc aaa gga caa gtt gaa ata gcc aac ctt tct     144
Ile Ile Gln Ser Leu Ser Lys Gly Gln Val Glu Ile Ala Asn Leu Ser
         35                  40                  45
```

-continued

| | | |
|---|---|---|
| gaa gct gca gat acg gta acg tta aac cgt gtg cta caa att gct tca<br>Glu Ala Ala Asp Thr Val Thr Leu Asn Arg Val Leu Gln Ile Ala Ser<br>50                      55                      60 | 192 |
| gat ccg aaa cca gga ttc aac aca att gac atc ggt cca gcg gga acg<br>Asp Pro Lys Pro Gly Phe Asn Thr Ile Asp Ile Gly Pro Ala Gly Thr<br>65                      70                      75                      80 | 240 |
| gcc atg cga ttc tta acg gct tac ctc aac ctt gtc aaa gga aat ttt<br>Ala Met Arg Phe Leu Thr Ala Tyr Leu Asn Leu Val Lys Gly Asn Phe<br>                      85                      90                      95 | 288 |
| atc ctt aca ggt act gaa cgc atg caa cag cgt cct ata ggt ata tta<br>Ile Leu Thr Gly Thr Glu Arg Met Gln Gln Arg Pro Ile Gly Ile Leu<br>                  100                 105                 110 | 336 |
| gtt gat gcc atg aaa gaa att ggt gca gac atc cac tat gac aag aaa<br>Val Asp Ala Met Lys Glu Ile Gly Ala Asp Ile His Tyr Asp Lys Lys<br>             115                120                 125 | 384 |
| gtc gga tac cct cct ttg aaa att gag ggc ggg ctg ttt caa gaa aaa<br>Val Gly Tyr Pro Pro Leu Lys Ile Glu Gly Gly Leu Phe Gln Glu Lys<br>130                      135                 140 | 432 |
| gac cgt gtc aag att aaa ggt aat atc agc agc caa tat ata tca gcc<br>Asp Arg Val Lys Ile Lys Gly Asn Ile Ser Ser Gln Tyr Ile Ser Ala<br>145                      150                 155                 160 | 480 |
| ctc tta tta att gca cct gca tta aaa aaa ggg ctt act tta gag att<br>Leu Leu Leu Ile Ala Pro Ala Leu Lys Lys Gly Leu Thr Leu Glu Ile<br>                  165                 170                 175 | 528 |
| gag ggt gaa tta acc tcc aga cct tat gta tca atg acc ttg gat atg<br>Glu Gly Glu Leu Thr Ser Arg Pro Tyr Val Ser Met Thr Leu Asp Met<br>             180                185                 190 | 576 |
| ctg aaa agt gtc ggg att cag cat gaa tgg aaa aac aat gcg att aaa<br>Leu Lys Ser Val Gly Ile Gln His Glu Trp Lys Asn Asn Ala Ile Lys<br>             195                200                 205 | 624 |
| att gcg ccg cag gca ttt gag aaa caa aca ata tat gtc gag cca gat<br>Ile Ala Pro Gln Ala Phe Glu Lys Gln Thr Ile Tyr Val Glu Pro Asp<br>210                      215                 220 | 672 |
| tgg agc gct gct tcc tat tgg tac gct atc gcc gca cta gca gat gca<br>Trp Ser Ala Ala Ser Tyr Trp Tyr Ala Ile Ala Ala Leu Ala Asp Ala<br>225                      230                 235                 240 | 720 |
| aac gca tcg atc gta ttg ccc gga tta aga aaa aac agc tta cag ggt<br>Asn Ala Ser Ile Val Leu Pro Gly Leu Arg Lys Asn Ser Leu Gln Gly<br>                  245                 250                 255 | 768 |
| gat att gct att ata agc att atg gag cat ttt ggt gta caa tcg agc<br>Asp Ile Ala Ile Ile Ser Ile Met Glu His Phe Gly Val Gln Ser Ser<br>             260                265                 270 | 816 |
| ttt gaa tcg gac gga tta cac tta aat aaa aag gta atc ggt tcg gat<br>Phe Glu Ser Asp Gly Leu His Leu Asn Lys Lys Val Ile Gly Ser Asp<br>             275                280                 285 | 864 |
| gta agc tta ttt aac ttt aaa gaa tgt ccc gat ctc gca caa act gta<br>Val Ser Leu Phe Asn Phe Lys Glu Cys Pro Asp Leu Ala Gln Thr Val<br>290                      295                 300 | 912 |
| gtt gtt gtc gcg gct gcg tta aaa cga gat gta tct ttt acg ggc ttg<br>Val Val Val Ala Ala Ala Leu Lys Arg Asp Val Ser Phe Thr Gly Leu<br>305                      310                 315                 320 | 960 |
| gag acc tta aaa att aag gag act gac cgt atc gcg gca cta caa aag<br>Glu Thr Leu Lys Ile Lys Glu Thr Asp Arg Ile Ala Ala Leu Gln Lys<br>                  325                 330                 335 | 1008 |
| gaa att gcg aaa ttt gga gcc gag cta att gaa gat ggc gat acc tac<br>Glu Ile Ala Lys Phe Gly Ala Glu Leu Ile Glu Asp Gly Asp Thr Tyr<br>             340                345                 350 | 1056 |
| cat ctg aaa aca gcg cag gta tat cag cct gaa gag gtt act ttc gat<br>His Leu Lys Thr Ala Gln Val Tyr Gln Pro Glu Glu Val Thr Phe Asp<br>             355                360                 365 | 1104 |

```
act tac gaa gat cat cgc atg gcg atg gcg ttc gca cca ctg gca tta      1152
Thr Tyr Glu Asp His Arg Met Ala Met Ala Phe Ala Pro Leu Ala Leu
    370                 375                 380 gtt ttc gac cag att aag att gct gaa cct caa gtt gta gaa aaa tca      1200
Val Phe Asp Gln Ile Lys Ile Ala Glu Pro Gln Val Val Glu Lys Ser
385                 390                 395                 400 tat cct gat ttt tgg aat cat tta cag gcg caa gct ttt gtc att gaa      1248
Tyr Pro Asp Phe Trp Asn His Leu Gln Ala Gln Ala Phe Val Ile Glu
                405                 410                 415 tag                                                                  1251
 *

<210> SEQ ID NO 14
<211> LENGTH: 416
<212> TYPE: PRT
<213> ORGANISM: Sphingobacterium multivorum/faecium

<400> SEQUENCE: 14

Met Asn Gln Gln Val Ile Thr Leu Thr His Pro Ser Lys Lys Ile Gln
 1               5                  10                  15

Gly Thr Val Gln Leu Thr Gly Ser Lys Ser Glu Ser Asn Arg Ala Leu
             20                  25                  30

Ile Ile Gln Ser Leu Ser Lys Gly Gln Val Glu Ile Ala Asn Leu Ser
         35                  40                  45

Glu Ala Ala Asp Thr Val Thr Leu Asn Arg Val Leu Gln Ile Ala Ser
     50                  55                  60

Asp Pro Lys Pro Gly Phe Asn Thr Ile Asp Ile Gly Pro Ala Gly Thr
65                  70                  75                  80

Ala Met Arg Phe Leu Thr Ala Tyr Leu Asn Leu Val Lys Gly Asn Phe
                 85                  90                  95

Ile Leu Thr Gly Thr Glu Arg Met Gln Gln Arg Pro Ile Gly Ile Leu
            100                 105                 110

Val Asp Ala Met Lys Glu Ile Gly Ala Asp Ile His Tyr Asp Lys Lys
        115                 120                 125

Val Gly Tyr Pro Pro Leu Lys Ile Glu Gly Gly Leu Phe Gln Glu Lys
    130                 135                 140

Asp Arg Val Lys Ile Lys Gly Asn Ile Ser Ser Gln Tyr Ile Ser Ala
145                 150                 155                 160

Leu Leu Leu Ile Ala Pro Ala Leu Lys Lys Gly Leu Thr Leu Glu Ile
                165                 170                 175

Glu Gly Glu Leu Thr Ser Arg Pro Tyr Val Ser Met Thr Leu Asp Met
            180                 185                 190

Leu Lys Ser Val Gly Ile Gln His Glu Trp Lys Asn Asn Ala Ile Lys
        195                 200                 205

Ile Ala Pro Gln Ala Phe Glu Lys Gln Thr Ile Tyr Val Glu Pro Asp
    210                 215                 220

Trp Ser Ala Ala Ser Tyr Trp Tyr Ala Ile Ala Ala Leu Ala Asp Ala
225                 230                 235                 240

Asn Ala Ser Ile Val Leu Pro Gly Leu Arg Lys Asn Ser Leu Gln Gly
                245                 250                 255

Asp Ile Ala Ile Ile Ser Ile Met Glu His Phe Gly Val Gln Ser Ser
            260                 265                 270

Phe Glu Ser Asp Gly Leu His Leu Asn Lys Lys Val Ile Gly Ser Asp
        275                 280                 285

Val Ser Leu Phe Asn Phe Lys Glu Cys Pro Asp Leu Ala Gln Thr Val
```

```
                290                 295                 300
Val Val Val Ala Ala Ala Leu Lys Arg Asp Val Ser Phe Thr Gly Leu
305                 310                 315                 320

Glu Thr Leu Lys Ile Lys Glu Thr Asp Arg Ile Ala Ala Leu Gln Lys
                325                 330                 335

Glu Ile Ala Lys Phe Gly Ala Glu Leu Ile Glu Asp Gly Asp Thr Tyr
                340                 345                 350

His Leu Lys Thr Ala Gln Val Tyr Gln Pro Glu Glu Val Thr Phe Asp
                355                 360                 365

Thr Tyr Glu Asp His Arg Met Ala Met Ala Phe Ala Pro Leu Ala Leu
            370                 375                 380

Val Phe Asp Gln Ile Lys Ile Ala Glu Pro Gln Val Val Glu Lys Ser
385                 390                 395                 400

Tyr Pro Asp Phe Trp Asn His Leu Gln Ala Gln Ala Phe Val Ile Glu
                405                 410                 415

<210> SEQ ID NO 15
<211> LENGTH: 431
<212> TYPE: PRT
<213> ORGANISM: Enterobacteriaceae sp.

<400> SEQUENCE: 15

Met Lys Val Thr Ile Gln Pro Gly Asp Leu Thr Gly Ile Leu Gln Ser
1               5                   10                  15

Pro Ala Ser Lys Ser Ser Met Gln Arg Ala Cys Ala Ala Ala Leu Val
                20                  25                  30

Ala Lys Gly Ile Ser Glu Ile Ile Asn Pro Gly His Ser Asn Asp Asp
            35                  40                  45

Lys Ala Ala Arg Asp Ile Val Ser Arg Leu Gly Ala Arg Leu Glu Asp
50                  55                  60

Gln Pro Asp Gly Ser Leu Gln Ile Thr Ser Glu Gly Val Lys Pro Val
65                  70                  75                  80

Ala Pro Phe Ile Asp Cys Gly Glu Ser Gly Leu Ser Ile Arg Met Phe
                85                  90                  95

Thr Pro Ile Val Ala Leu Ser Lys Glu Glu Val Thr Ile Lys Gly Ser
            100                 105                 110

Gly Ser Leu Val Thr Arg Pro Met Asp Phe Phe Asp Glu Ile Leu Pro
        115                 120                 125

His Leu Gly Val Lys Val Lys Ser Asn Gln Gly Lys Leu Pro Leu Val
    130                 135                 140

Ile Gln Gly Pro Leu Lys Pro Ala Asp Val Thr Val Asp Gly Ser Leu
145                 150                 155                 160

Ser Ser Gln Phe Leu Thr Gly Leu Leu Leu Ala Tyr Ala Ala Ala Asp
                165                 170                 175

Ala Ser Asp Val Ala Ile Lys Val Thr Asn Leu Lys Ser Arg Pro Tyr
            180                 185                 190

Ile Asp Leu Thr Leu Asp Val Met Lys Arg Phe Gly Leu Lys Thr Pro
        195                 200                 205

Glu Asn Arg Asn Tyr Glu Glu Phe Tyr Phe Lys Ala Gly Asn Val Tyr
    210                 215                 220

Asp Glu Thr Lys Met Gln Arg Tyr Thr Val Glu Gly Asp Trp Ser Gly
225                 230                 235                 240

Gly Ala Phe Leu Leu Val Ala Gly Ala Ile Ala Gly Pro Ile Thr Val
                245                 250                 255
```

```
Arg Gly Leu Asp Ile Ala Ser Thr Gln Ala Asp Lys Ala Ile Val Gln
            260                 265                 270

Ala Leu Met Ser Ala Asn Ala Gly Ile Ala Ile Asp Ala Lys Glu Ile
        275                 280                 285

Lys Leu His Pro Ala Asp Leu Asn Ala Phe Glu Phe Asp Ala Thr Asp
    290                 295                 300

Cys Pro Asp Leu Phe Pro Leu Val Ala Leu Ala Ser Tyr Cys Lys
305                 310                 315                 320

Gly Glu Thr Lys Ile Lys Gly Val Ser Arg Leu Ala His Lys Glu Ser
                325                 330                 335

Asp Arg Gly Leu Thr Leu Gln Asp Glu Phe Gly Lys Met Gly Val Glu
            340                 345                 350

Ile His Leu Glu Gly Asp Leu Met Arg Val Ile Gly Gly Lys Gly Val
        355                 360                 365

Lys Gly Ala Glu Val Ser Ser Arg His Asp His Arg Ile Ala Met Ala
    370                 375                 380

Cys Ala Val Ala Ala Leu Lys Ala Val Gly Glu Thr Thr Ile Glu His
385                 390                 395                 400

Ala Glu Ala Val Asn Lys Ser Tyr Pro Asp Phe Tyr Ser Asp Leu Lys
                405                 410                 415

Gln Leu Gly Gly Val Val Ser Leu Asn His Gln Phe Asn Phe Ser
            420                 425                 430

<210> SEQ ID NO 16
<211> LENGTH: 418
<212> TYPE: PRT
<213> ORGANISM: Pseudomonas syringae strain 1448a

<400> SEQUENCE: 16

Met Arg Pro Gln Ala Thr Leu Thr Val Leu Pro Val Glu Arg Pro Leu
  1               5                  10                  15

Val Gly Arg Val Ser Pro Pro Gly Ser Lys Ser Ile Thr Asn Arg Ala
             20                  25                  30

Leu Leu Leu Ala Gly Leu Ala Lys Gly Thr Ser Arg Leu Thr Gly Ala
         35                  40                  45

Leu Lys Ser Asp Asp Thr Arg Val Met Ser Glu Ala Leu Arg Leu Met
     50                  55                  60

Gly Val Gln Val Asp Glu Pro Asp Asp Ser Thr Phe Val Val Thr Ser
 65                  70                  75                  80

Ser Gly His Trp Gln Ala Pro Gln Gln Ala Leu Phe Leu Gly Asn Ala
                 85                  90                  95

Gly Thr Ala Thr Arg Phe Leu Thr Ala Ala Leu Ala Asn Phe Glu Gly
            100                 105                 110

Asp Phe Val Val Asp Gly Asp Glu Tyr Met Arg Lys Arg Pro Ile Gly
        115                 120                 125

Pro Leu Val Asp Ala Leu Gln Arg Met Gly Val Glu Val Ser Ala Pro
    130                 135                 140

Ser Gly Cys Pro Pro Val Ala Ile Lys Gly Lys Gly Leu Glu Ala
145                 150                 155                 160

Gly Arg Ile Glu Ile Asp Gly Asn Leu Ser Ser Gln Tyr Val Ser Ala
                165                 170                 175

Leu Leu Met Ala Gly Ala Cys Gly Lys Gly Pro Val Glu Val Ala Leu
            180                 185                 190

Thr Gly Ser Glu Ile Gly Ala Arg Gly Tyr Val Asp Leu Thr Leu Ala
        195                 200                 205
```

-continued

```
Ala Met Gln Ala Phe Gly Ala Glu Val Gln Ala Ile Gly Glu Thr Ala
    210                 215                 220
Trp Lys Val Ser Ala Thr Gly Tyr Arg Ala Thr Asp Phe His Ile Glu
225                 230                 235                 240
Pro Asp Ala Ser Ala Ala Thr Tyr Leu Trp Ala Ala Gln Ala Leu Thr
                245                 250                 255
Glu Gly Asp Ile Asp Leu Gly Val Ala Ser Asp Ala Phe Thr Gln Pro
            260                 265                 270
Asp Ala Leu Ala Ser Gln Ile Ile Ala Ser Phe Pro Asn Met Pro Ala
        275                 280                 285
Val Ile Asp Gly Ser Gln Met Gln Asp Ala Ile Pro Thr Leu Ala Val
    290                 295                 300
Leu Ala Ala Phe Asn Arg Gln Pro Val Arg Phe Val Gly Ile Ala Asn
305                 310                 315                 320
Leu Arg Val Lys Glu Cys Asp Arg Ile Ser Ala Leu Ser His Gly Leu
                325                 330                 335
Cys Ala Ile Ala Pro Gly Leu Ala Val Glu Glu Gly Asp Asp Leu Leu
            340                 345                 350
Val His Ala Asn Pro Ala Leu Ala Gly Thr Thr Val Ala Ala Leu Ile
        355                 360                 365
Asp Thr His Ser Asp His Arg Ile Ala Met Cys Phe Ala Leu Ala Gly
    370                 375                 380
Leu Lys Ile Ala Gly Ile Arg Ile Leu Asp Pro Asp Cys Val Gly Lys
385                 390                 395                 400
Thr Tyr Pro Gly Tyr Trp Asp Ala Leu Ala Ser Leu Gly Val Arg Val
                405                 410                 415
Gln Arg

<210> SEQ ID NO 17
<211> LENGTH: 418
<212> TYPE: PRT
<213> ORGANISM: Pseudomonas syringae strain DC3000

<400> SEQUENCE: 17

Met Arg Pro Gln Ala Thr Leu Thr Val Met Pro Val Glu Arg Pro Leu
1               5                   10                  15
Val Gly Arg Val Ser Pro Pro Gly Ser Lys Ser Ile Thr Asn Arg Ala
            20                  25                  30
Leu Leu Leu Ala Gly Leu Ala Lys Gly Thr Ser Arg Leu Thr Gly Ala
        35                  40                  45
Leu Lys Ser Asp Asp Thr Arg Val Met Ser Glu Ala Leu Arg Leu Met
    50                  55                  60
Gly Val Gln Val Asp Glu Pro Asp Asp Ser Thr Phe Val Val Thr Ser
65                  70                  75                  80
Ser Gly His Trp Gln Ala Pro Gln Gln Ala Leu Phe Leu Gly Asn Ala
                85                  90                  95
Gly Thr Ala Thr Arg Phe Leu Thr Ala Ala Leu Ala Asn Phe Glu Gly
            100                 105                 110
Asp Phe Val Val Asp Gly Asp Glu Tyr Met Arg Lys Arg Pro Ile Gly
        115                 120                 125
Pro Leu Val Asp Ala Leu Gln Arg Met Gly Val Glu Ile Ser Ala Pro
    130                 135                 140
Ser Gly Cys Pro Pro Val Ala Ile Lys Gly Lys Gly Gly Leu Gln Ala
145                 150                 155                 160
```

Gly Arg Ile Glu Ile Asp Gly Asn Leu Ser Ser Gln Tyr Val Ser Ala
                165                 170                 175

Leu Leu Met Ala Gly Ala Cys Gly Lys Gly Ser Leu Glu Val Ala Leu
            180                 185                 190

Thr Gly Ser Glu Ile Gly Ala Arg Gly Tyr Val Asp Leu Thr Leu Ala
        195                 200                 205

Ala Met Gln Ala Phe Gly Ala Glu Val Gln Ala Ile Gly Asp Ala Ala
    210                 215                 220

Trp Lys Val Ser Ala Thr Gly Tyr His Ala Thr Asp Phe His Ile Glu
225                 230                 235                 240

Pro Asp Ala Ser Ala Ala Thr Tyr Leu Trp Ala Ala Gln Ala Leu Thr
                245                 250                 255

Glu Gly Asn Ile Asp Leu Gly Val Ala Ser Asp Ala Phe Thr Gln Pro
            260                 265                 270

Asp Ala Leu Ala Ser Gln Ile Ile Asp Ser Phe Pro Asn Met Pro Ala
        275                 280                 285

Val Ile Asp Gly Ser Gln Met Gln Asp Ala Ile Pro Thr Leu Ala Val
    290                 295                 300

Leu Ala Ala Phe Asn Arg Gln Pro Val Arg Phe Val Gly Ile Ala Asn
305                 310                 315                 320

Leu Arg Val Lys Glu Cys Asp Arg Ile Ser Ala Leu Cys Asp Gly Leu
                325                 330                 335

Cys Ala Ile Ala Pro Gly Leu Ala Val Glu Glu Gly Asp Asp Leu Ile
            340                 345                 350

Val His Ala Asn Pro Ala Leu Ala Gly Thr Thr Val Asn Ala Leu Ile
        355                 360                 365

Asp Thr His Ser Asp His Arg Ile Ala Met Cys Phe Ala Leu Ala Gly
    370                 375                 380

Leu Lys Ile Lys Gly Ile His Ile Gln Asp Pro Asp Cys Val Ala Lys
385                 390                 395                 400

Thr Tyr Pro Gly Tyr Trp Asp Ala Leu Ala Ser Leu Gly Val Ser Val
                405                 410                 415

Gln Arg

<210> SEQ ID NO 18
<211> LENGTH: 418
<212> TYPE: PRT
<213> ORGANISM: Pseudomonas syringae strain B728

<400> SEQUENCE: 18

Met Arg Pro Gln Ala Thr Leu Thr Val Leu Pro Val Glu Arg Pro Leu
1               5                   10                  15

Val Gly Arg Val Ser Pro Pro Gly Ser Lys Ser Ile Thr Asn Arg Ala
            20                  25                  30

Leu Leu Leu Ala Gly Leu Ala Lys Gly Thr Ser Arg Leu Thr Gly Ala
        35                  40                  45

Leu Lys Ser Asp Asp Thr Arg Val Met Ser Glu Ala Leu Arg Leu Met
    50                  55                  60

Gly Val Gln Val Asp Glu Pro Asp Asp Ser Thr Phe Val Val Thr Ser
65                  70                  75                  80

Ser Gly His Trp Gln Ala Pro Gln Gln Ala Leu Phe Leu Gly Asn Ala
                85                  90                  95

Gly Thr Ala Thr Arg Phe Leu Thr Ala Ala Leu Ala Asn Phe Glu Gly
            100                 105                 110

```
Asp Phe Val Val Asp Gly Asp Glu Tyr Met Arg Lys Arg Pro Ile Gly
            115                 120                 125

Pro Leu Val Asp Ala Leu Gln Arg Met Gly Val Glu Val Ser Ala Pro
        130                 135                 140

Ser Gly Cys Pro Pro Val Ala Ile Lys Gly Lys Gly Gly Leu Glu Ala
145                 150                 155                 160

Gly Arg Ile Glu Ile Asp Gly Asn Leu Ser Ser Gln Tyr Val Ser Ala
                165                 170                 175

Leu Leu Met Ala Gly Ala Cys Gly Lys Gly Pro Val Glu Val Ala Leu
            180                 185                 190

Thr Gly Ser Glu Ile Gly Ala Arg Gly Tyr Leu Asp Leu Thr Leu Ala
        195                 200                 205

Ala Met Arg Ala Phe Gly Ala Glu Val Gln Ala Ile Gly Asp Ala Ala
    210                 215                 220

Trp Lys Val Ser Ala Thr Gly Tyr Arg Ala Thr Asp Phe His Ile Glu
225                 230                 235                 240

Pro Asp Ala Ser Ala Ala Thr Tyr Leu Trp Ala Ala Gln Ala Leu Thr
                245                 250                 255

Glu Gly Ala Ile Asp Leu Gly Val Ala Ser Asn Ala Phe Thr Gln Pro
            260                 265                 270

Asp Ala Leu Ala Ser Gln Ile Ile Ala Ser Phe Pro Asn Met Pro Ala
        275                 280                 285

Val Ile Asp Gly Ser Gln Met Gln Asp Ala Ile Pro Thr Leu Ala Val
    290                 295                 300

Leu Ala Ala Phe Asn Arg Gln Pro Val Arg Phe Val Gly Ile Ala Asn
305                 310                 315                 320

Leu Arg Val Lys Glu Cys Asp Arg Ile Ser Ala Leu Ser Asn Gly Leu
                325                 330                 335

Cys Ala Ile Ala Pro Gly Leu Ala Val Glu Glu Gly Asp Asp Leu Ile
            340                 345                 350

Val Thr Ala Asn Pro Thr Leu Ala Gly Thr Thr Val Asp Ala Leu Ile
        355                 360                 365

Asp Thr His Ser Asp His Arg Ile Ala Met Cys Phe Ala Leu Ala Gly
    370                 375                 380

Leu Lys Ile Ala Gly Ile Arg Ile Leu Asp Pro Asp Cys Val Ala Lys
385                 390                 395                 400

Thr Tyr Pro Gly Tyr Trp Asp Ala Leu Ala Ser Leu Gly Val Ser Val
                405                 410                 415

Gln Arg

<210> SEQ ID NO 19
<211> LENGTH: 419
<212> TYPE: PRT
<213> ORGANISM: Brevundomonas vesicularis

<400> SEQUENCE: 19

Met Met Met Gly Arg Ala Lys Leu Thr Ile Ile Pro Pro Gly Lys Pro
  1               5                  10                  15

Leu Thr Gly Arg Ala Met Pro Pro Gly Ser Lys Ser Ile Thr Asn Arg
                20                  25                  30

Ala Leu Leu Leu Ala Gly Leu Ala Lys Gly Thr Ser Arg Leu Thr Gly
            35                  40                  45

Ala Leu Lys Ser Asp Asp Thr Arg Tyr Met Ala Glu Ala Leu Arg Ala
        50                  55                  60
```

Met Gly Val Thr Ile Asp Glu Pro Asp Asp Thr Phe Ile Val Lys
 65                  70                  75                  80

Gly Ser Gly Lys Leu Gln Pro Pro Ala Ala Pro Leu Phe Leu Gly Asn
                 85                  90                  95

Ala Gly Thr Ala Thr Arg Phe Leu Thr Ala Ala Ala Leu Val Asp
                100                 105                 110

Gly Lys Val Ile Val Asp Gly Asp Ala His Met Arg Lys Arg Pro Ile
                115                 120                 125

Gly Pro Leu Val Asp Ala Leu Arg Ser Leu Gly Ile Asp Ala Ser Ala
130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
                180                 185                 190

Leu Leu Gly Glu His Ile Gly Ala Leu Gly Tyr Ile Asp Leu Thr Val
                195                 200                 205

Ala Ala Met Arg Ala Phe Gly Ala Lys Val Glu Arg Val Ser Pro Val
210                 215                 220

Ala Trp Arg Val Glu Pro Thr Gly Tyr His Ala Ala Asp Phe Val Ile
225                 230                 235                 240

Glu Pro Asp Ala Ser Ala Thr Tyr Leu Trp Ala Ala Glu Val Leu
                245                 250                 255

Ser Gly Gly Lys Ile Asp Leu Gly Thr Pro Ala Glu Gln Phe Ser Gln
                260                 265                 270

Pro Asp Ala Lys Ala Tyr Asp Leu Ile Ser Lys Phe Pro His Leu Pro
                275                 280                 285

Ala Val Ile Asp Gly Ser Gln Met Gln Asp Ala Ile Pro Thr Leu Ala
290                 295                 300

Val Leu Ala Ala Phe Asn Glu Met Pro Val Arg Phe Val Gly Ile Glu
305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
                340                 345                 350

Ile Ile Ala Ser Asp Pro Ser Leu Ala Gly Lys Ile Leu Thr Ala Glu
                355                 360                 365

Ile Asp Ser Phe Ala Asp His Arg Ile Ala Met Ser Phe Ala Leu Ala
                370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp

<210> SEQ ID NO 20
<211> LENGTH: 425
<212> TYPE: PRT
<213> ORGANISM: Agrobacterium tumefaciens strain C58

<400> SEQUENCE: 20

Met Ile Glu Leu Thr Ile Thr Pro Pro Gly His Pro Leu Ser Gly Lys
 1               5                  10                  15

```
Val Glu Pro Pro Gly Ser Lys Ser Ile Thr Asn Arg Ala Leu Leu Leu
            20                  25                  30

Ala Gly Leu Ala Lys Gly Lys Ser His Leu Ser Gly Ala Leu Lys Ser
        35                  40                  45

Asp Asp Thr Leu Tyr Met Ala Glu Ala Leu Arg Glu Met Gly Val Lys
50                  55                  60

Val Thr Glu Pro Asp Ala Thr Thr Phe Val Val Glu Gly Thr Gly Val
65                  70                  75                  80

Leu Gln Gln Pro Glu Lys Pro Leu Phe Leu Gly Asn Ala Gly Thr Ala
                85                  90                  95

Thr Arg Phe Leu Thr Ala Ala Gly Ala Leu Val Asp Gly Ala Val Ile
            100                 105                 110

Ile Asp Gly Asp Glu His Met Arg Lys Arg Pro Ile Leu Pro Leu Val
        115                 120                 125

Gln Ala Leu Arg Ala Leu Gly Val Glu Ala Asp Ala Pro Thr Gly Cys
130                 135                 140

Pro Pro Val Thr Val Arg Gly Lys Gly Met Gly Phe Pro Lys Gly Ser
145                 150                 155                 160

Val Thr Ile Asp Ala Asn Leu Ser Ser Gln Tyr Val Ser Ala Leu Leu
                165                 170                 175

Met Ala Ala Cys Gly Asp Lys Pro Val Asp Ile Ile Leu Lys Gly
            180                 185                 190

Glu Glu Ile Gly Ala Lys Gly Tyr Ile Asp Leu Thr Thr Ser Ala Met
        195                 200                 205

Glu Ala Phe Gly Ala Lys Val Glu Arg Val Ser Asn Ala Ile Trp Arg
210                 215                 220

Val His Pro Thr Gly Tyr Thr Ala Thr Asp Phe His Ile Glu Pro Asp
225                 230                 235                 240

Ala Ser Ala Ala Thr Tyr Leu Trp Gly Ala Glu Leu Leu Thr Gly Gly
                245                 250                 255

Ala Ile Asp Ile Gly Thr Pro Ala Asp Lys Phe Thr Gln Pro Asp Ala
            260                 265                 270

Lys Ala Tyr Glu Val Met Ala Gln Phe Pro His Leu Pro Ala Glu Ile
275                 280                 285

Asp Gly Ser Gln Met Gln Asp Ala Ile Pro Thr Ile Ala Val Ile Ala
290                 295                 300

Ala Phe Asn Glu Thr Pro Val Arg Phe Val Gly Ile Ala Asn Leu Arg
305                 310                 315                 320

Val Lys Glu Cys Asp Arg Ile Arg Ala Val Ser Leu Gly Leu Asn Glu
                325                 330                 335

Ile Arg Glu Gly Leu Ala His Glu Glu Gly Asp Asp Leu Ile Val His
            340                 345                 350

Ala Asp Pro Ser Leu Ala Gly Gln Thr Val Asp Ala Ser Ile Asp Thr
        355                 360                 365

Phe Ala Asp His Arg Ile Ala Met Ser Phe Ala Leu Ala Ala Leu Lys
370                 375                 380

Ile Gly Gly Ile Ala Ile Gln Asn Pro Ala Cys Val Ala Lys Thr Tyr
385                 390                 395                 400

Pro Gly Tyr Trp Lys Ala Leu Ala Ser Leu Gly Val Asp Tyr Thr Glu
                405                 410                 415

Lys Glu Ser Ala Ala Glu Pro Gln His
            420                 425
```

<210> SEQ ID NO 21
<211> LENGTH: 428
<212> TYPE: PRT
<213> ORGANISM: Clostridium acetobutylicum

<400> SEQUENCE: 21

```
Met Asn Cys Val Lys Ile Asn Pro Cys Cys Leu Lys Gly Asp Ile Lys
 1               5                  10                  15

Ile Pro Pro Ser Lys Ser Leu Gly His Arg Ala Ile Ile Cys Ala Ala
            20                  25                  30

Leu Ser Glu Glu Ser Thr Ile Glu Asn Ile Ser Tyr Ser Lys Asp
        35                  40                  45

Ile Lys Ala Thr Cys Ile Gly Met Ser Lys Leu Gly Ala Leu Ile Ile
    50                  55                  60

Glu Asp Ala Lys Asp Asn Ser Thr Leu Lys Ile Lys Lys Gln Lys Leu
65                  70                  75                  80

Val Ser Lys Glu Lys Val Tyr Ile Asp Cys Ser Glu Ser Gly Ser Thr
                85                  90                  95

Val Arg Phe Leu Ile Pro Ile Ser Leu Ile Glu Glu Arg Asn Val Val
                100                 105                 110

Phe Asp Gly Gln Gly Lys Leu Ser Tyr Arg Pro Leu Asp Ser Tyr Phe
            115                 120                 125

Asn Ile Phe Asp Glu Lys Glu Ile Ala Tyr Ser His Pro Glu Gly Lys
        130                 135                 140

Val Leu Pro Leu Gln Ile Lys Gly Arg Leu Lys Ala Gly Met Phe Asn
145                 150                 155                 160

Leu Pro Gly Asn Ile Ser Ser Gln Phe Ile Ser Gly Leu Met Phe Ser
                165                 170                 175

Leu Pro Phe Leu Glu Gly Asp Ser Ile Ile Asn Ile Thr Thr Asn Leu
            180                 185                 190

Glu Ser Val Gly Tyr Val Asp Met Thr Ile Asp Met Leu Lys Lys Phe
        195                 200                 205

Gly Ile Glu Ile Glu Asn Lys Ala Tyr Lys Ser Phe Phe Ile Lys Gly
    210                 215                 220

Asn Gln Lys Cys Lys Gly Thr Lys Tyr Lys Val Glu Gly Asp Phe Ser
225                 230                 235                 240

Gln Ala Ala Phe Trp Leu Ser Ala Gly Ile Leu Asn Gly Asn Ile Asn
                245                 250                 255

Cys Lys Asp Leu Asn Ile Ser Ser Leu Gln Gly Asp Lys Val Ile Leu
            260                 265                 270

Asp Ile Leu Lys Lys Met Gly Gly Ala Ile Asp Glu Lys Ser Phe Ser
        275                 280                 285

Ser Lys Lys Ser His Thr His Gly Ile Val Ile Asp Ala Ser Gln Cys
    290                 295                 300

Pro Asp Leu Val Pro Ile Leu Ser Val Val Ala Ala Leu Ser Glu Gly
305                 310                 315                 320

Thr Thr Lys Ile Val Asn Ala Ala Arg Leu Arg Ile Lys Glu Ser Asp
                325                 330                 335

Arg Leu Lys Ala Met Ala Thr Glu Leu Asn Lys Leu Gly Ala Glu Val
            340                 345                 350

Val Glu Leu Glu Asp Gly Leu Leu Ile Glu Gly Lys Glu Lys Leu Lys
        355                 360                 365

Gly Gly Glu Val Glu Ser Trp Asn Asp His Arg Ile Ala Met Ala Leu
    370                 375                 380
```

```
Gly Ile Ala Ala Leu Arg Cys Glu Glu Ser Val Thr Ile Asn Gly Ser
385                 390                 395                 400

Glu Cys Val Ser Lys Ser Tyr Pro Gln Phe Trp Ser Asp Leu Lys Gln
                405                 410                 415

Leu Gly Gly Asp Val His Glu Trp Ser Leu Gly Glu
            420                 425

<210> SEQ ID NO 22
<211> LENGTH: 444
<212> TYPE: PRT
<213> ORGANISM: Ochrobactrum/Brucella

<400> SEQUENCE: 22

Met Ala Cys Leu Pro Asp Asp Ser Gly Pro His Val Gly His Ser Thr
 1               5                  10                  15

Pro Pro Cys Leu Asp Gln Glu Pro Cys Thr Leu Ser Ser Gln Lys Thr
            20                  25                  30

Val Thr Val Thr Pro Pro Asn Phe Pro Leu Thr Gly Lys Val Ala Pro
        35                  40                  45

Pro Gly Ser Lys Ser Ile Thr Asn Arg Ala Leu Leu Leu Ala Ala Leu
    50                  55                  60

Ala Lys Gly Thr Ser Arg Leu Ser Gly Ala Leu Lys Ser Asp Asp Thr
65                  70                  75                  80

Arg His Met Ser Val Ala Leu Arg Gln Met Gly Val Thr Ile Asp Glu
                85                  90                  95

Pro Asp Asp Thr Thr Phe Val Val Thr Ser Gln Gly Ser Leu Gln Leu
            100                 105                 110

Pro Ala Gln Pro Leu Phe Leu Gly Asn Ala Gly Thr Ala Met Arg Phe
        115                 120                 125

Leu Thr Ala Ala Val Ala Thr Val Gln Gly Thr Val Val Leu Asp Gly
    130                 135                 140

Asp Glu Tyr Met Gln Lys Arg Pro Ile Gly Pro Leu Leu Ala Thr Leu
145                 150                 155                 160

Gly Gln Asn Gly Ile Gln Val Asp Ser Pro Thr Gly Cys Pro Pro Val
                165                 170                 175

Thr Val His Gly Ala Gly Lys Val Gln Ala Arg Arg Phe Glu Ile Asp
            180                 185                 190

Gly Gly Leu Ser Ser Gln Tyr Val Ser Ala Leu Leu Met Leu Ala Ala
        195                 200                 205

Cys Gly Glu Ala Pro Ile Glu Val Ala Leu Thr Gly Lys Asp Ile Gly
    210                 215                 220

Ala Arg Gly Tyr Val Asp Leu Thr Leu Asp Cys Met Arg Ala Phe Gly
225                 230                 235                 240

Ala Gln Val Asp Ile Val Asp Asp Thr Thr Trp Arg Val Ala Pro Thr
                245                 250                 255

Gly Tyr Thr Ala His Asp Tyr Leu Ile Glu Pro Asp Ala Ser Ala Ala
            260                 265                 270

Thr Tyr Leu Trp Ala Ala Glu Val Leu Thr Gly Gly Arg Ile Asp Ile
        275                 280                 285

Gly Val Ala Ala Gln Asp Phe Thr Gln Pro Asp Ala Lys Ala Gln Ala
    290                 295                 300

Val Ile Ala Gln Phe Pro Asn Met Gln Ala Thr Val Val Gly Ser Gln
305                 310                 315                 320

Met Gln Asp Ala Ile Pro Thr Leu Ala Val Leu Ala Ala Phe Asn Asn
```

```
                  325                 330                 335
Thr Pro Val Arg Phe Thr Glu Leu Ala Asn Leu Arg Val Lys Glu Cys
              340                 345                 350
Asp Arg Val Gln Ala Leu His Asp Gly Leu Asn Glu Ile Arg Pro Gly
              355                 360                 365
Leu Ala Thr Ile Glu Gly Asp Asp Leu Leu Val Ala Ser Asp Pro Ala
              370                 375                 380
Leu Ala Gly Thr Ala Cys Thr Ala Leu Ile Asp Thr His Ala Asp His
385                 390                 395                 400
Arg Ile Ala Met Cys Phe Ala Leu Ala Gly Leu Lys Val Ser Gly Ile
              405                 410                 415
Arg Ile Gln Asp Pro Asp Cys Val Ala Lys Thr Tyr Pro Asp Tyr Trp
              420                 425                 430
Lys Ala Leu Ala Ser Leu Gly Val His Leu Ser Tyr
              435                 440

<210> SEQ ID NO 23
<211> LENGTH: 425
<212> TYPE: PRT
<213> ORGANISM: Agrobacterium tumefaciens strain C58

<400> SEQUENCE: 23

Met Ile Glu Leu Thr Ile Thr Pro Pro Gly His Pro Leu Ser Gly Lys
1               5                   10                  15
Val Glu Pro Pro Gly Ser Lys Ser Ile Thr Asn Arg Ala Leu Leu Leu
              20                  25                  30
Ala Gly Leu Ala Lys Gly Lys Ser Arg Leu Thr Gly Ala Leu Lys Ser
              35                  40                  45
Asp Asp Thr Leu Tyr Met Ala Glu Ala Leu Arg Glu Met Gly Val Lys
              50                  55                  60
Val Thr Glu Pro Asp Ala Thr Thr Phe Val Val Glu Ser Ser Gly Gly
65                  70                  75                  80
Leu His Gln Pro Glu Lys Pro Leu Phe Leu Gly Asn Ala Gly Thr Ala
              85                  90                  95
Thr Arg Phe Leu Thr Ala Ala Ala Leu Val Asp Gly Ala Val Ile
              100                 105                 110
Ile Asp Gly Asp Glu His Met Arg Lys Arg Pro Ile Met Pro Leu Val
              115                 120                 125
Glu Ala Leu Arg Ser Leu Gly Val Glu Ala Glu Ala Pro Thr Gly Cys
              130                 135                 140
Pro Pro Val Thr Val Cys Gly Lys Gly Thr Gly Phe Pro Lys Gly Ser
145                 150                 155                 160
Val Thr Ile Asp Ala Asn Leu Ser Ser Gln Tyr Val Ser Ala Leu Leu
              165                 170                 175
Met Ala Ala Ala Cys Gly Asp Lys Pro Val Asp Ile Ile Leu Lys Gly
              180                 185                 190
Glu Glu Ile Gly Ala Lys Gly Tyr Ile Asp Leu Thr Thr Ser Ala Met
              195                 200                 205
Glu Ala Phe Gly Ala Lys Val Glu Arg Val Ser Asn Ala Ile Trp Arg
              210                 215                 220
Val His Pro Thr Gly Tyr Thr Ala Thr Asp Phe His Ile Glu Pro Asp
225                 230                 235                 240
Ala Ser Ala Ala Thr Tyr Leu Trp Gly Ala Glu Leu Leu Thr Gly Gly
              245                 250                 255
```

```
Ala Ile Asp Ile Gly Thr Pro Ala Asp Lys Phe Thr Gln Pro Asp Ala
            260                 265                 270

Lys Ala His Glu Val Met Ala Gln Phe Pro His Leu Pro Ala Glu Ile
        275                 280                 285

Asp Gly Ser Gln Met Gln Asp Ala Ile Pro Thr Ile Ala Val Leu Ala
    290                 295                 300

Ala Phe Asn Glu Thr Pro Val Arg Phe Val Gly Ile Ala Asn Leu Arg
305                 310                 315                 320

Val Lys Glu Cys Asp Arg Ile Arg Ala Val Ser Leu Gly Leu Asn Glu
                325                 330                 335

Ile Arg Asp Gly Leu Ala His Glu Gly Asp Asp Leu Ile Val His
            340                 345                 350

Ser Asp Pro Ser Leu Ala Gly Gln Thr Val Asn Ala Ser Ile Asp Thr
        355                 360                 365

Phe Ala Asp His Arg Ile Ala Met Ser Phe Ala Leu Ala Ala Leu Lys
    370                 375                 380

Ile Gly Gly Ile Ala Ile Gln Asn Pro Ala Cys Val Gly Lys Thr Tyr
385                 390                 395                 400

Pro Gly Tyr Trp Lys Ala Leu Ala Ser Leu Gly Val Glu Tyr Ser Glu
                405                 410                 415

Lys Glu Thr Ala Ala Glu Pro Gln His
            420                 425

<210> SEQ ID NO 24
<211> LENGTH: 414
<212> TYPE: PRT
<213> ORGANISM: Sulfolobus solfataricus

<400> SEQUENCE: 24

Met Ile Val Lys Ile Tyr Pro Ser Lys Ile Ser Gly Ile Ile Lys Ala
  1               5                  10                  15

Pro Gln Ser Lys Ser Leu Ala Ile Arg Leu Ile Phe Leu Ser Leu Phe
             20                  25                  30

Thr Arg Val Tyr Leu His Asn Leu Val Leu Ser Glu Asp Val Ile Asp
         35                  40                  45

Ala Ile Lys Ser Val Arg Ala Leu Gly Val Lys Val Lys Asn Asn Ser
     50                  55                  60

Glu Phe Ile Pro Pro Glu Lys Leu Glu Ile Lys Glu Arg Phe Ile Lys
 65                  70                  75                  80

Leu Lys Gly Ser Ala Thr Thr Leu Arg Met Leu Ile Pro Ile Leu Ala
                 85                  90                  95

Ala Ile Gly Gly Glu Val Thr Ile Asp Ala Asp Glu Ser Leu Arg Arg
            100                 105                 110

Arg Pro Leu Asn Arg Ile Val Gln Ala Leu Ser Asn Tyr Gly Ile Ser
        115                 120                 125

Phe Ser Ser Tyr Ser Leu Pro Leu Thr Ile Thr Gly Lys Leu Ser Ser
    130                 135                 140

Asn Glu Ile Lys Ile Ser Gly Asp Glu Ser Ser Gln Tyr Ile Ser Gly
145                 150                 155                 160

Leu Ile Tyr Ala Leu His Ile Leu Asn Gly Gly Ser Ile Glu Ile Leu
                165                 170                 175

Pro Pro Ile Ser Ser Lys Ser Tyr Ile Leu Leu Thr Ile Asp Leu Phe
            180                 185                 190

Lys Arg Phe Gly Ser Asp Val Lys Phe Tyr Gly Ser Lys Ile His Val
        195                 200                 205
```

```
Asn Pro Asn Asn Leu Val Glu Phe Gln Gly Glu Val Ala Gly Asp Tyr
        210                 215                 220

Gly Leu Ala Ser Phe Tyr Ala Leu Ser Ala Leu Val Ser Gly Gly Gly
225                 230                 235                 240

Ile Thr Ile Thr Asn Leu Trp Glu Pro Lys Glu Tyr Phe Gly Asp His
                245                 250                 255

Ser Ile Val Lys Ile Phe Ser Glu Met Gly Ala Ser Ser Glu Tyr Lys
                260                 265                 270

Asp Gly Arg Trp Phe Val Lys Ala Lys Asp Lys Tyr Ser Pro Ile Lys
            275                 280                 285

Ile Asp Ile Asp Asp Ala Pro Asp Leu Ala Met Thr Ile Ala Gly Leu
290                 295                 300

Ser Ala Ile Ala Glu Gly Thr Ser Glu Ile Ile Gly Ile Glu Arg Leu
305                 310                 315                 320

Arg Ile Lys Glu Ser Asp Arg Ile Glu Ser Ile Arg Lys Ile Leu Gly
                325                 330                 335

Leu Tyr Gly Val Gly Ser Glu Val Lys Tyr Asn Ser Ile Leu Ile Phe
                340                 345                 350

Gly Ile Asn Lys Gly Met Leu Asn Ser Pro Val Thr Asp Cys Leu Asn
                355                 360                 365

Asp His Arg Val Ala Met Met Ser Ser Ala Leu Ala Leu Val Asn Gly
370                 375                 380

Gly Val Ile Thr Ser Ala Glu Cys Val Gly Lys Ser Asn Pro Asn Tyr
385                 390                 395                 400

Trp Gln Asp Leu Leu Ser Leu Asn Ala Lys Ile Ser Ile Glu
                405                 410

<210> SEQ ID NO 25
<211> LENGTH: 424
<212> TYPE: PRT
<213> ORGANISM: Fusobacterium nucleatum

<400> SEQUENCE: 25

Met Arg Asn Met Asn Lys Lys Ile Ile Lys Ala Asp Lys Leu Val Gly
1               5                   10                  15

Glu Val Thr Pro Pro Ser Lys Ser Val Leu His Arg Tyr Ile Ile
                20                  25                  30

Ala Ser Ser Leu Ala Lys Gly Ile Ser Lys Ile Glu Asn Ile Ser Tyr
            35                  40                  45

Ser Asp Asp Ile Ile Ala Thr Ile Glu Ala Met Lys Lys Leu Gly Ala
    50                  55                  60

Asn Ile Glu Lys Lys Asp Asn Tyr Leu Leu Ile Asp Gly Ser Lys Thr
65                  70                  75                  80

Phe Asp Lys Glu Tyr Leu Asn Asn Asp Ser Glu Ile Asp Cys Asn Glu
                85                  90                  95

Ser Gly Ser Thr Leu Arg Phe Leu Phe Pro Leu Ser Ile Val Lys Glu
            100                 105                 110

Asn Lys Ile Leu Phe Lys Gly Lys Gly Lys Leu Phe Lys Arg Pro Leu
        115                 120                 125

Ser Pro Tyr Phe Glu Asn Phe Asp Lys Tyr Gln Ile Lys Cys Ser Ser
    130                 135                 140

Ile Asn Glu Asn Lys Ile Leu Leu Asp Gly Glu Leu Lys Ser Gly Val
145                 150                 155                 160

Tyr Glu Ile Asp Gly Asn Ile Ser Ser Gln Phe Ile Thr Gly Leu Leu
```

165                 170                 175
Phe Ser Leu Pro Leu Asn Gly Asn Ser Lys Ile Ile Lys Gly
            180                 185                 190

Lys Leu Glu Ser Ser Tyr Ile Asp Ile Thr Leu Asp Cys Leu Asn
            195                 200                 205

Lys Phe Gly Ile Asn Ile Ile Asn Asn Ser Tyr Lys Glu Phe Ile Ile
210                 215                 220

Glu Gly Asn Gln Thr Tyr Lys Ser Gly Asn Tyr Gln Val Glu Ala Asp
225                 230                 235                 240

Tyr Ser Gln Val Ala Phe Phe Leu Val Ala Asn Ser Ile Gly Ser Asn
            245                 250                 255

Ile Lys Ile Asn Gly Leu Asn Val Asn Ser Leu Gln Gly Asp Lys Lys
            260                 265                 270

Ile Ile Asp Phe Ile Ser Glu Ile Asp Asn Trp Thr Lys Asn Glu Lys
            275                 280                 285

Leu Ile Leu Asp Gly Ser Glu Thr Pro Asp Ile Pro Ile Leu Ser
            290                 295                 300

Leu Lys Ala Cys Ile Ser Lys Lys Glu Ile Glu Ile Val Asn Ile Ala
305                 310                 315                 320

Arg Leu Arg Ile Lys Glu Ser Asp Arg Leu Ser Ala Thr Val Gln Glu
            325                 330                 335

Leu Ser Lys Leu Gly Phe Asp Leu Ile Glu Lys Glu Asp Ser Ile Leu
            340                 345                 350

Ile Asn Ser Arg Lys Asn Phe Asn Glu Ile Ser Asn Asn Ser Pro Ile
            355                 360                 365

Ser Leu Ser Ser His Ser Asp His Arg Ile Ala Met Thr Val Ala Ile
370                 375                 380

Ala Ser Thr Cys Tyr Glu Gly Glu Ile Ile Leu Asp Asn Leu Asp Cys
385                 390                 395                 400

Val Lys Lys Ser Tyr Pro Asn Phe Trp Glu Val Phe Leu Ser Leu Gly
            405                 410                 415

Gly Lys Ile Tyr Glu Tyr Leu Gly
            420

<210> SEQ ID NO 26
<211> LENGTH: 428
<212> TYPE: PRT
<213> ORGANISM: Methanopyrus kandleri

<400> SEQUENCE: 26

Met Lys Arg Val Glu Leu Glu Gly Ile Pro Glu Val Arg Gly Thr Val
1               5                   10                  15

Cys Pro Pro Pro Ser Lys Ser Gly Ser His Arg Ala Leu Ile Ala Ala
                20                  25                  30

Ser Leu Cys Asp Gly Ser Thr Glu Leu Trp Asn Val Leu Asp Ala Glu
            35                  40                  45

Asp Val Arg Ala Thr Leu Arg Leu Cys Arg Met Leu Gly Ala Glu Val
50                  55                  60

Asp Val Asp Gly Glu Glu Arg Leu Glu Ala Thr Val Ser Gly Phe Gly
65                  70                  75                  80

Asp Ser Pro Arg Ala Pro Glu Asp Val Val Asp Cys Gly Asn Ser Gly
                85                  90                  95

Thr Thr Leu Arg Leu Gly Cys Gly Leu Ala Ala Leu Val Glu Gly Thr
            100                 105                 110

```
Thr Ile Leu Thr Gly Asp Asp Ser Leu Arg Ser Arg Pro Val Gly Asp
            115                 120                 125

Leu Leu Ala Ala Leu Arg Ser Leu Gly Val Asp Ala Arg Gly Arg Val
130                 135                 140

Val Arg Gly Glu Glu Tyr Pro Pro Val Val Ile Ser Gly Arg Pro Leu
145                 150                 155                 160

Arg Glu Arg Val Ala Val Tyr Gly Asp Val Ser Ser Gln Phe Val Ser
                165                 170                 175

Ala Leu Leu Phe Leu Gly Ala Gly Leu Gly Ala Leu Arg Val Asp Val
            180                 185                 190

Val Gly Asp Leu Arg Ser Arg Pro Tyr Val Asp Met Thr Val Glu Thr
            195                 200                 205

Leu Glu Arg Phe Gly Val Ser Val Val Arg Glu Gly Ser Ser Phe Glu
210                 215                 220

Val Glu Gly Arg Pro Arg Ser Pro Gly Lys Leu Arg Val Glu Asn Asp
225                 230                 235                 240

Trp Ser Ser Ala Gly Tyr Phe Val Ala Leu Gly Ala Ile Gly Gly Glu
                245                 250                 255

Met Arg Ile Glu Gly Val Asp Leu Asp Ser Ser His Pro Asp Arg Arg
            260                 265                 270

Ile Val Glu Ile Thr Arg Glu Met Gly Ala Glu Val Arg Arg Ile Asp
            275                 280                 285

Gly Gly Ile Val Val Arg Ser Thr Gly Arg Leu Glu Gly Val Glu Val
            290                 295                 300

Asp Leu Ser Asp Ser Pro Asp Leu Val Pro Thr Val Ala Ala Met Ala
305                 310                 315                 320

Cys Phe Ala Glu Gly Val Thr Arg Ile Glu Asn Val Gly His Leu Arg
                325                 330                 335

Tyr Lys Glu Val Asp Arg Leu Arg Ala Leu Ala Ala Glu Leu Pro Lys
            340                 345                 350

Phe Gly Val Glu Val Arg Glu Gly Lys Asp Trp Leu Glu Ile Val Gly
            355                 360                 365

Gly Glu Pro Val Gly Ala Arg Val Asp Ser Arg Gly Asp His Arg Met
370                 375                 380

Ala Met Ala Leu Ala Val Val Gly Ala Phe Ala Arg Gly Lys Thr Val
385                 390                 395                 400

Val Glu Arg Ala Asp Ala Val Ser Ile Ser Tyr Pro Arg Phe Trp Glu
                405                 410                 415

Asp Leu Ala Ser Val Gly Val Pro Val His Ser Val
            420                 425

<210> SEQ ID NO 27
<211> LENGTH: 436
<212> TYPE: PRT
<213> ORGANISM: Arthrobacter globiformis

<400> SEQUENCE: 27

Met Ala Leu Glu Arg Gly Gln His Gly Arg Ser Arg Arg Leu Phe Gly
1               5                   10                  15

Ala Ser Leu Glu Arg Ile Thr Met Glu Thr Asp Arg Leu Val Ile Pro
            20                  25                  30

Gly Ser Lys Ser Ile Thr Asn Arg Ala Leu Leu Leu Ala Ala Ala Ala
        35                  40                  45

Lys Gly Thr Ser Val Leu Val Arg Pro Leu Val Ser Ala Asp Thr Ser
50                  55                  60
```

```
Ala Phe Lys Thr Ala Ile Gln Ala Leu Gly Ala Asn Val Ser Ala Asp
 65                  70                  75                  80

Gly Asp Asn Trp Val Glu Gly Leu Gly Gln Ala Pro His Leu Asp
                 85                  90                  95

Ala Asp Ile Trp Cys Glu Asp Ala Gly Thr Val Ala Arg Phe Leu Pro
            100                 105                 110

Pro Phe Val Ala Ala Gly Gln Gly Lys Phe Thr Val Asp Gly Ser Glu
            115                 120                 125

Gln Leu Arg Arg Arg Pro Leu Arg Pro Leu Val Asp Gly Ile Arg His
    130                 135                 140

Leu Gly Ala Arg Val Ser Ser Glu Gln Leu Pro Leu Thr Ile Glu Ala
145                 150                 155                 160

Ser Gly Leu Ala Gly Gly Glu Tyr Glu Ile Glu Ala His Gln Ser Ser
                165                 170                 175

Gln Phe Ala Ser Gly Leu Ile Met Ala Ala Pro Tyr Ala Arg Gln Gly
            180                 185                 190

Leu Arg Val Arg Ile Pro Asn Pro Val Ser Gln Pro Tyr Leu Thr Met
    195                 200                 205

Thr Leu Arg Met Met Arg Asp Phe Gly Leu Glu Thr Ser Thr Asp Gly
210                 215                 220

Ala Thr Val Ser Val Pro Pro Gly Arg Tyr Thr Ala Arg Arg Tyr Glu
225                 230                 235                 240

Ile Glu Pro Asp Ala Ser Thr Ala Ser Tyr Phe Ala Ala Ser Ala
                245                 250                 255

Val Ser Gly Arg Ser Phe Glu Phe Gln Gly Leu Gly Thr Asp Ser Ile
                260                 265                 270

Gln Gly Asp Thr Ser Phe Phe Asn Val Leu Gly Arg Leu Gly Ala Glu
            275                 280                 285

Val His Trp Ala Pro Asn Ser Val Thr Ile Ser Gly Pro Glu Arg Leu
            290                 295                 300

Asn Gly Asp Ile Glu Val Asp Met Gly Glu Ile Ser Asp Thr Phe Met
305                 310                 315                 320

Thr Leu Ala Ala Ile Ala Pro Leu Ala Asp Gly Pro Ile Thr Ile Thr
                325                 330                 335

Asn Ile Gly His Ala Arg Leu Lys Glu Ser Asp Arg Ile Ser Ala Met
            340                 345                 350

Glu Thr Asn Leu Arg Thr Leu Gly Val Gln Thr Asp Val Gly His Asp
            355                 360                 365

Trp Met Arg Ile Tyr Pro Ser Thr Pro His Gly Gly Arg Val Asn Cys
            370                 375                 380

His Arg Asp His Arg Ile Ala Met Ala Phe Ser Ile Leu Gly Leu Arg
385                 390                 395                 400

Val Asp Gly Ile Thr Leu Asp Asp Pro Gln Cys Val Gly Lys Thr Phe
                405                 410                 415

Pro Gly Phe Phe Asp Tyr Leu Gly Arg Leu Phe Pro Glu Lys Ala Leu
            420                 425                 430

Thr Leu Pro Gly
            435

<210> SEQ ID NO 28
<211> LENGTH: 1251
<212> TYPE: DNA
<213> ORGANISM: Artificial Sequence
<220> FEATURE:
```

<223> OTHER INFORMATION: synthetic sequence encoding GRG31 (syngrg31)

<400> SEQUENCE: 28

```
atgaaccagc aggtgatcac cttgacacat ccaagcaaga agatccaagg caccgtgcag      60
ctcaccggca gcaagagcga gagcaacagg gcgctcatca ttcagagctt gagcaagggc     120
caagtggaga tcgccaacct ctcagaagct gctgacaccg tcaccctcaa cagggtgctg     180
caaattgctt cagatccaaa gcctggcttc aacaccatcg acattgggcc ggccggcacc     240
gccatgaggt tcttgacggc ctacctcaac ctggtgaagg gcaacttcat cctcaccggc     300
actgaaagga tgcagcagcg gcccatcggc atcctggtgg acgccatgaa ggagatcggc     360
gccgacatcc actacgacaa gaaggtgggc tacccgccgc taaagattga aggaggcctc     420
ttccaagaga aggaccgcgt caagatcaag ggcaacatca gcagccagta catctcggcg     480
ctgctgctca tcgcgccggc gctgaagaag gggctgacgc tggagattga aggagagctg     540
acatcaaggc cttatgtgag catgacgctg acatgctga agagcgtcgg catccagcat     600
gaatggaaga acaacgccat caagattgct cctcaagcat tgagaagca gaccatctat     660
gtggagccag attggagcgc cgcctcatat tggtacgcca tcgccgcgct ggctgatgca     720
aatgcaagca tcgtgctgcc agggctgagg aagaacagcc tccaaggaga catcgccatc     780
atcagcatca tggagcattt tggagttcaa agttcatttg agagcgacgg cctccacctc     840
aacaagaagg tgattggaag tgatgtgagc ctcttcaact tcaaggagtg cccagatctt     900
gctcaaacag tggtggtggt ggcggcggcg ctgaagagag atgtgagctt caccggcctg     960
gagacgctga agatcaagga gaccgacagg atcgccgcgc tacagaagga gatcgccaag    1020
ttcggcgccg agctgattga agatggagac acctaccacc tcaagacggc gcaggtgtac    1080
cagccagaag aagtccacctt cgacacctat gaagatcaca ggatggcaat ggccttcgcg    1140
ccgctagctc tggtgttcga ccagatcaag attgctgaac ctcaagtggt ggagaagagc    1200
tacccggact tctggaacca cctccaagct caagccttcg tcatcgagta g             1251
```

<210> SEQ ID NO 29
<211> LENGTH: 1401
<212> TYPE: DNA
<213> ORGANISM: Artificial Sequence
<220> FEATURE:
<223> OTHER INFORMATION: synthetic sequence encoding GRG25 (syngrg25)

<400> SEQUENCE: 29

```
atgctgctga ggacggtgaa gacctgcttg gagcccaagg acctgcccat ctgcaccgcc      60
tcggcgccgg gctcgccgac ggacaaactt cacaatgctg agaagacatg gtgggcggcg     120
ccgcacgccg ccaccggcct ggacgccatc gtctccgtgc cggcatcaaa gagcctcacc     180
aacagatatt tgatcctggc ggcgctggca agctcgccaa gcaccatcca acaccttg      240
atctcaaggg acaccgagct gatgctggac gcgctggcgg ccttcggcat cggcatcgag     300
aggacaactc aacctgatgg aagcaccacc gtcgccatca cgccgggcaa gctggccacc     360
gggccgctga gcatcgactg cggcctcgcc ggcaccgtga tgaggttcgt gccgccgctc     420
gccgccgtcg ccgcgcctc agtggcattt gatggagatg aagcagcaag ggtgcggcca     480
atggcgccgg tgctggacgc gctggagacg ctgggagcaa ggattgagta cgccggcacg     540
ccgggcatgc tgcccttcac aatggatgct tctgctcttc aagaaaggca tgaggtgctg     600
attgatgctt ctggaagctc tcagttcatc tcggcgctgc tgctggtggg ccaagctcta     660
cctggaggcc tcaagctccg cgccgccgcc ggccacatcg cctcgcctga tcacatcgcc     720
```

```
atgacagttc aaacattgag ggagctcggc gtggaggtgg cggtgggaga agatgcaaga      780
agctggagca tcgcgccggg gcagctctca ggcttcacca tcaccgtgga gcctgatttg      840
agcaacgccg gccccttcct ggcggcggcg ctggcaacaa atggcaccgt ccgcgtgccc      900
ttctggccgg caagcaccac tcaagttgga ggaaaatggg tgcaaatcct ctcaaggatg      960
ggcgccgaga tctctcatgg agaagatggc gtgctgaccg tccgcggcac cggcgtcatc     1020
cgcggcatcg actatgctga tgcttcagag ctggcgccga cgctggcggc gctctgcacc     1080
ctcgccgact cgccaagcaa gctcaccggc atcggccacc tccgcggcca tgaaacagat     1140
cggctggcgg cgctggagac agagctgcc aaggtgggcg ccaccgtgac aagcaccgac      1200
gacgcgctgg agatcatccc tggaactctt caagctgctg atctggattc atatgaagat     1260
cacaggatgg ccaccgccgg cgcgctgctg ggctggcca ttgaaggagt gagggtggag      1320
aacatcgcca ccaccgccaa gaccatgccg gacttcccgc agctgtggac ggacatggcg     1380
gcgacggcca agggccaagg a                                                1401

<210> SEQ ID NO 30
<211> LENGTH: 1392
<212> TYPE: DNA
<213> ORGANISM: Artificial Sequence
<220> FEATURE:
<223> OTHER INFORMATION: synthetic sequence encoding GRG26 (syngrg26)

<400> SEQUENCE: 30
atgcctggga cgccggcgac gcagacagat gattctggaa caagcaccgc ctcggcgctg       60
ccgctgtggc cggcgccctt cgccagccat cctgttgatg ccaccgtcac cgtgcctgga      120
agcaagagcc tcaccaacag atatttggtg ctggcggcgc tggcaaatgg gccatcaagg      180
ctccgcgcgc cgcttcattc aagagattcg gcgctgatgt tggaggcgct ccgccgcctc      240
ggcgccacca tcactgaagt tcctggagat ggtcaatatg accagatct ggaggtgacg       300 cccatcgacc cggcggcggc ggcgtcggag acggccatcg actgcggcct cgccggcacc      360
gtgatgaggt tcgtgccgcc gctggcggcg ctgaggaatg gagcttcagt ttttgatgga      420
gatcctcatg caaggcagcg gccaatgggc accatcatcg aggcgctgag gacgctcggc      480
gtggatgttt cagcaatgga tgcaaggcg ccgggcagct tgcccttcaa ggtgagcggc       540
accggcagcg tccgcggcgg ccacctggtg attgatgctt cagcaagctc tcaatttgtg      600
tcggcgctgc tgctggtggg agcaagattt gaagaaggcc tccacctgga gcatgttggc      660
aagccggtgc caagcctgga ccacatcaac atgacggtgg cggtgctgcg cggcgtcggc      720
gtgcaagttg atgattcagt tccaaatcat tggagggtga gccccggcgc catccaagca      780
tttgatgaaa gaattgagca agatctttca aatgctggac ccttcctggc ggcggcgctg      840
gccaccaagg gcaccgtcag gattccaaat tggccggcaa gcaccactca agttggagat      900
ctttggagga acatcctggc aacaatgggc gccaccgtga cgctggacaa tggcacctc       960 accgtcaccg gcggcagcga gatcctcggc gccgactttg atgaaacttc agagctggcg     1020
ccgacggtgg cggcgctctg cgcgctagca acctcgccat caaggctcac cggcattgct     1080
cacctccgcg gccatgaaac agatcggctg gcggcgctgg tggcggagat caacaggctc     1140
ggcggcgacg ccgaggagac aagtgatggg ctggtgatca ggccggcggc gctgcactca     1200
ggagtggtgc acagctatgc tgatcacagg atgccaccg ccggcgccat cctcggcctc      1260
gccgtggaag gagtgagggt ggaggacatc gccaccacca gcaagaccat gccggagttc     1320
```

<210> SEQ ID NO 31
<211> LENGTH: 1365
<212> TYPE: DNA
<213> ORGANISM: Artificial Sequence
<220> FEATURE:
<223> OTHER INFORMATION: synthetic sequence encoding GRG27 (syngrg27)

<400> SEQUENCE: 31

```
atgaccggca ccaccgccgc caacaccgag ccggacaagg cggcgtcgct gccgctgtgg      60
ccggcgccat atgcaaatgg gccggtggac gccaccgtca ccgtgcctgg aagcaagagc     120
ctcaccaaca ggttcctggt gctggcggcg ctggctgatg gccatcaag gctccgcgcg     180
cctcttcatt caagagattc ggcgctgatg atccaagctc ttcggcagct cggcgccacc     240
gtcaccgagg tgccaggaga tggagattat ggacctgatc tggagatcac gccgctggac     300
ccaagcgccg ccggcagcag caccgccatc gactgcggcc tcgccggcac cgtgatgagg     360
ttcgtgccgc cgctggcggc gctgagatca ggcgccaccg tctttgatgg agatcctcat     420
gcaaggaaca ggccaatggg caccatcatc gaggcgctgc tggcgctggg agttcctgtt     480
gctgctgaag aggaaggac gccgtcggcg ctgcccttca ccgtggaagg caccggcgag     540
gtgcgcggcg ccaccctggt gattgatgct tcagcaagct ctcaatttgt gtcggcgctg     600
ctgctggtgg gcgcgcgctt cacagaaggc ctccacctgg agcatgttgg caagccggtg     660
ccaagcctgg atcacatcac catgacggtg gaggtgctga ggagcgtcgg cgtcaccgtg     720
gatgattcag ttcccaacca ctggagggtg tcgccgggca agatcaccgc cttcgaccag     780
aggatcgagc aagatctttc aaatgctgga cccttcctgg cggcggcgct ggcaactcat     840
ggcaccgtga ggattccaaa ttggcccatc ggcaccactc aagttggtga tctttggagg     900
accatcctgg cggcaatggg cgccaccgtc accttggacg gcggcaccct caccgtcacc     960
ggcggcaatg agatcaaagg agctgatttt gatgaaactt cagagctggc gccgacggtg    1020
gcggcgctct gcgcgctggc caccgggcca tcaaggctga ccggcattgc tcacctccgc    1080
ggccatgaaa cagatcggct ggcggcgctg gtggcggaga tcaacaggct gggaggagat    1140
gctgaagaaa ctgctgatgg gctgctgatc aggccggcga cgctacatgg cggcgtcatc    1200
cacagctacg ccgaccacag gatggccacc gccggcgcca tcctcggcct cgccgtcgac    1260
ggcgtccagg tggaggacat cgccaccacc agcaagacca tgccggagtt cccggagatg    1320
tgggcaagga tgctggacag cgccggcacc aacgaggccg gcaac                    1365
```

<210> SEQ ID NO 32
<211> LENGTH: 1383
<212> TYPE: DNA
<213> ORGANISM: Artificial Sequence
<220> FEATURE:
<223> OTHER INFORMATION: synthetic sequence encoding GRG28 (syngrg28)

<400> SEQUENCE: 32

```
atgaccggca ccaccgccgc caacaccggc agcaacagcg tggacacctt gccgctctgg      60
gcggcgccat atgcaacaag gccggtggac gccaccgtca ccgtgcctgg aagcaagagc     120
ctcaccaaca ggttcctggt gctggcggcg ctggctgatg gccaagccg cctccgcgcg     180
cctcttcatt caagagattc tgtgctgatg atccaggcgc tgcggcagct cggcgccacc     240
gtcaccgagg tgcccggcga cggcgactat ggacctgatc tggagatcac gccgatggac     300
```

```
ccttcagcaa gcggcgccga dacggccatc gactgcggcc tcgccggcac cgtgatgagg    360
ttcgtgccgc cgctggcggc gctgaggaat gggccaacaa catttgatgg agatcctcat    420
gcaaggaaga ggccaatggg caccatcatc gaggcgctgc tggcgctagg agttcctgtg    480
gcaacagaag gaggaaggac gccgtcggcg ctgcccttct ccgtgatgg caccggcgag     540 gtgcgcggcg gccacctggt gattgatgct tcagcaagct ctcaatttgt gtcggcgctg    600
ctgctggtgg gagcaaggtt cacagaaggc ctccacctgg agcatgttgg caagccggtg    660
ccaagcctgg atcacatcaa catgaccgtc tccgtgctgc gcggcgtcgg cgtcaaggtg    720
gatgattcag ttcccaacca ctggagggtg gcgccgggcc ccatccatgc cttcgaccag    780
aggatcgagc aagatctttc aaatgctgga cccttcctgg cggcggcgct ggcaacaaga    840
ggaacagtga ggattccaaa ttggccgacg cagacaactc aagttggtga tctatggagg    900
agcatcctgg tggagatggg cgccaccgtc accttggaga atggcaccct caccgtcaaa    960
ggaggaccag atcaaagg agctgatttt gatgagacct ccgagctggc gccgacggtg     1020
gcggcgctct gcgcgctggc accgggcca tcaaggctga ccggcattgc tcacctccgc     1080
ggccatgaaa cagatcggct ggcggcgctg gcggcggaga tcaacaggct gggaggagat    1140
gctgaagaaa ctgctgatgg cctcatcatc aggccggcga cgctgcatcc tggagtagtt    1200
cattcatatg ctgatcacag gatggccacc gccggcgcca cctcggcct cgccgtggaa     1260 ggagttcaag tggaggacat cgccaccacc agcaagacgg tgccagaatt tcctcaaatg    1320
tgggaggcca tgctgcaaca aggaactgga gaagatgaga ccgtcacctc agaagcaagc    1380
aac                                                                  1383
```

<210> SEQ ID NO 33
<211> LENGTH: 1293
<212> TYPE: DNA
<213> ORGANISM: Artificial Sequence
<220> FEATURE:
<223> OTHER INFORMATION: synthetic sequence encoding GRG29 (syngrg29)

<400> SEQUENCE: 33

```
atggatgtca tcgtcaagcc gacgccaagc ctcaatggag agatcggcgc gctgagcagc     60
aagaactaca caacaagata tttgctggcg gcggcgctgg cagaaggaac aagcaccatc    120
cactaccctg ctcattcaga agattctgat gccatgagaa gatgcatctc cgacctcggc    180
gccgtgctgg aagaagatga cagcaagatc gtcatccaag gcttcggctc acatccaaga    240
gatgtgaggg agctcaatgt tggaaatgct ggcgccgtgc tgcgcttctt gatgggcgtg    300
acggcgctct gccctgatgt caccttcgtc aacacctacc ccgacagcct cggcaagagg    360
cctcatgatg acctcatcga cgcgctgggg cagctaggag tggaggtgca gcatgagcaa    420
ggaaggctgc ccatcaccat caaaggagga caagccaagg gcggccacat cagagtttct    480
ggaagcgtca gctctcagta cctctcggcg ctgctcttcg tgacgccgct gctggcggag    540
gacagcacca tcgaggtgct aaatgacctc aagagcaagg tggtgatcgg ccagacgctg    600
gaggtgctgg agcaagctgg catcgtcatc catgcttcag atgactacat gagcttccgc    660
gtgcccggcg ccaagcctaa agccgcag acctacaccg tccaaggaga ttatcctgga     720
agcgccgccg tgctggccgc cgccgccgtc acccaaagtg atgtgaagat cctccggctg    780
atggagcaat caaagcaagg agaaagagca attgttgatg tgctgaggat gatggaggtg    840
ccgctcaccc atgaaaatga tgtggtgcat gttcaaggaa atggcacctt gaaggcggtg    900
```

```
gagtttgatg gagatgctgc aacagatgct gtgctggcaa tggtggcggc ggcggtgttt      960
gctgaaggaa catcaagatt ctacaatgtg gagaacttga gatacaagga atgtgacagg     1020
atcaccgact acctcaacga gctgaggaag gccggcgcca atgtggagga gaggcaagct     1080
gagatcattg ttcatggaag gccagaagga gtggagggcg gcgtggagat caatgctcac     1140
tacgaccacc gcgtcatcat ggcgctaaca gtggtggggc tgaggagcaa ggagccgctg     1200
aggatcagag atgctcatca tgtgccaag agctacccctc aatattttga tcatcttcaa     1260
gctctcggcg cctccgtgca gtgggtgaag gag                                  1293

<210> SEQ ID NO 34
<211> LENGTH: 1293
<212> TYPE: DNA
<213> ORGANISM: Artificial Sequence
<220> FEATURE:
<223> OTHER INFORMATION: synthetic sequence encoding GRG30 (syngrg30)

<400> SEQUENCE: 34
atggatgtca tcgtcaagcc gacgccaagc ctcaatggag agatcggcgc gctgagcagc       60
aagaactaca caacaagata tttgctggcg gcggcgctgg cagaaggaac aagcaccatc      120
cactaccctg ctcattcaga agattctgat gccatgagaa gatgcatcag ggacctcggc      180
gccgtgctgg aagaagatga cagcaagatc gtcatccaag gcttcggctc acatcctcat      240
gatgtgaggg agctcaatgt tggaaatgct ggcgccgtgc tgcgcttctt gatgggcgtg      300
acggcgctct gcccggaggt gaccttcgtc aacacctacc ccgacagcct cggcaagagg      360
cctcatgatg acctcatcga cgcgctgggg cagctaggag tggaggtgca gcatgagcaa      420
ggaaggctgc ccatcaccat caaggagga caagcaaaag gaggccacat cagagtttct      480
ggaagcgtca gctctcagta cctctcggcg ctgctcttcg tgacgccgct gctggcggag      540
gacagcacca tcgaggtgct aaatgacctc aagagcaagg tggtgatcgg ccagacgctg      600
gaggtgctgg agcaagctgg catcgtcatc catgcttcag atgactacat gagcttccgc      660
gtgcccggcg ccaagccta aagccgcag acctacaccg tccaaggaga ttatcctgga      720
agcgccgccg tgctggcggc ggcggcggtg acacaaagtg atgtgaagat cctccggctg      780
atggagcaat caaagcaagg agaaagagca attgttgatg tgctgaggat gatggaggtg      840
ccgctcaccc atgaaaatga tgtggtgcat gttcaaggaa atggcacctt gaaggcggtg      900
gagtttgatg gagatgctgc caccgacgcc gtgctggcaa tggtggcggc ggcggtgttt      960
gctgaaggaa catcaagatt ctacaatgtg gagaacttga gatacaagga atgtgacagg     1020
atcaccgact acctcaacga gctgaggaag gccggcgcca atgtggagga gaggcaagct     1080
gagatcattg ttcatggaag gccagaagga gtggagggcg gcgtggagat caatgctcac     1140
tacgaccacc gcgtcatcat ggcgctaaca gtggtggggc tgaggagcaa ggagccgctg     1200
aggatcagag atgctcatca tgtgccaag agctacccctc aatattttga tcatcttcaa     1260
gctctcggcg cctccgtgca gtgggtgaag gag                                  1293

<210> SEQ ID NO 35
<211> LENGTH: 431
<212> TYPE: PRT
<213> ORGANISM: Enterobacteriaciae

<400> SEQUENCE: 35

Met Lys Val Thr Ile Gln Pro Gly Asp Leu Thr Gly Ile Ile Gln Ser
  1               5                  10                  15
```

```
Pro Ala Ser Lys Ser Ser Met Gln Arg Ala Cys Ala Ala Leu Val
            20                  25                  30
Ala Lys Gly Ile Ser Glu Ile Ile Asn Pro Gly His Ser Asn Asp Asp
        35                  40                  45
Lys Ala Ala Arg Asp Ile Val Ser Arg Leu Gly Ala Arg Leu Glu Asp
50                  55                  60
Gln Pro Asp Gly Ser Leu Gln Ile Thr Ser Glu Gly Val Lys Pro Val
65                  70                  75                  80
Ala Pro Phe Ile Asp Cys Gly Glu Ser Gly Leu Ser Ile Arg Met Phe
                85                  90                  95
Thr Pro Ile Val Ala Leu Ser Lys Glu Val Thr Ile Lys Gly Ser
            100                 105                 110
Gly Ser Leu Val Thr Arg Pro Met Asp Phe Phe Asp Glu Ile Leu Pro
        115                 120                 125
His Leu Gly Val Lys Val Lys Ser Asn Gln Gly Lys Leu Pro Leu Val
    130                 135                 140
Ile Gln Gly Pro Leu Lys Pro Ala Asp Val Thr Val Asp Gly Ser Leu
145                 150                 155                 160
Ser Ser Gln Phe Leu Thr Gly Leu Leu Leu Ala Tyr Ala Ala Ala Asp
                165                 170                 175
Ala Ser Asp Val Ala Ile Lys Val Thr Asn Leu Lys Ser Arg Pro Tyr
            180                 185                 190
Ile Asp Leu Thr Leu Asp Val Met Lys Arg Phe Gly Leu Lys Thr Pro
        195                 200                 205
Glu Asn Arg Asn Tyr Glu Glu Phe Tyr Phe Lys Ala Gly Asn Val Tyr
    210                 215                 220
Asp Glu Thr Lys Met Gln Arg Tyr Thr Val Glu Gly Asp Trp Ser Gly
225                 230                 235                 240
Gly Ala Phe Leu Leu Val Ala Gly Ala Ile Ala Gly Pro Ile Thr Val
                245                 250                 255
Arg Gly Leu Asp Ile Ala Ser Thr Gln Ala Asp Lys Ala Ile Val Gln
            260                 265                 270
Ala Leu Met Ser Ala Asn Ala Gly Ile Ala Ile Asp Ala Lys Glu Ile
        275                 280                 285
Lys Leu His Pro Ala Asp Leu Asn Ala Phe Glu Phe Asp Ala Thr Asp
    290                 295                 300
Cys Pro Asp Leu Phe Pro Pro Leu Val Ala Leu Ala Ser Tyr Cys Lys
305                 310                 315                 320
Gly Glu Thr Lys Ile Lys Gly Val Ser Arg Leu Ala His Lys Glu Ser
                325                 330                 335
Asp Arg Gly Leu Thr Leu Gln Asp Glu Phe Gly Lys Met Gly Val Glu
            340                 345                 350
Ile His Leu Glu Gly Asp Leu Met Arg Val Ile Gly Lys Gly Val
        355                 360                 365
Lys Gly Ala Glu Val Ser Ser Arg His Asp His Arg Ile Ala Met Ala
    370                 375                 380
Cys Ala Val Ala Ala Leu Lys Ala Val Gly Glu Thr Thr Ile Glu His
385                 390                 395                 400
Ala Glu Ala Val Asn Lys Ser Tyr Pro Asp Phe Tyr Ser Asp Leu Lys
                405                 410                 415
Gln Leu Gly Gly Val Val Ser Leu Asn His Gln Phe Asn Phe Ser
            420                 425                 430
```

<210> SEQ ID NO 36
<211> LENGTH: 414
<212> TYPE: PRT
<213> ORGANISM: Sulfolobus solfataricus

<400> SEQUENCE: 36

```
Met Ile Val Lys Ile Tyr Pro Ser Lys Ile Ser Gly Ile Ile Lys Ala
 1               5                  10                  15

Pro Gln Ser Lys Ser Leu Ala Ile Arg Leu Ile Phe Leu Ser Leu Phe
            20                  25                  30

Thr Arg Val Tyr Leu His Asn Leu Val Leu Ser Glu Asp Val Ile Asp
        35                  40                  45

Ala Ile Lys Ser Val Arg Ala Leu Gly Val Lys Val Lys Asn Asn Ser
    50                  55                  60

Glu Phe Ile Pro Pro Glu Lys Leu Glu Ile Lys Glu Arg Phe Ile Lys
65                  70                  75                  80

Leu Lys Gly Ser Ala Thr Thr Leu Arg Met Leu Ile Pro Ile Leu Ala
                85                  90                  95

Ala Ile Gly Gly Glu Val Thr Ile Asp Ala Asp Glu Ser Leu Arg Arg
            100                 105                 110

Arg Pro Leu Asn Arg Ile Val Gln Ala Leu Ser Asn Tyr Gly Ile Ser
        115                 120                 125

Phe Ser Ser Tyr Ser Leu Pro Leu Thr Ile Thr Gly Lys Leu Ser Ser
    130                 135                 140

Asn Glu Ile Lys Ile Ser Gly Asp Glu Ser Ser Gln Tyr Ile Ser Gly
145                 150                 155                 160

Leu Ile Tyr Ala Leu His Ile Leu Asn Gly Gly Ser Ile Glu Ile Leu
                165                 170                 175

Pro Pro Ile Ser Ser Lys Ser Tyr Ile Leu Leu Thr Ile Asp Leu Phe
            180                 185                 190

Lys Arg Phe Gly Ser Asp Val Lys Phe Tyr Gly Ser Lys Ile His Val
        195                 200                 205

Asn Pro Asn Asn Leu Val Glu Phe Gln Gly Glu Val Ala Gly Asp Tyr
    210                 215                 220

Gly Leu Ala Ser Phe Tyr Ala Leu Ser Ala Leu Val Ser Gly Gly Gly
225                 230                 235                 240

Ile Thr Ile Thr Asn Leu Trp Glu Pro Lys Glu Tyr Phe Gly Asp His
                245                 250                 255

Ser Ile Val Lys Ile Phe Ser Glu Met Gly Ala Ser Ser Glu Tyr Lys
            260                 265                 270

Asp Gly Arg Trp Phe Val Lys Ala Lys Asp Lys Tyr Ser Pro Ile Lys
        275                 280                 285

Ile Asp Ile Asp Asp Ala Pro Asp Leu Ala Met Thr Ile Ala Gly Leu
    290                 295                 300

Ser Ala Ile Ala Glu Gly Thr Ser Glu Ile Ile Gly Ile Glu Arg Leu
305                 310                 315                 320

Arg Ile Lys Glu Ser Asp Arg Ile Glu Ser Ile Arg Lys Ile Leu Gly
                325                 330                 335

Leu Tyr Gly Val Gly Ser Glu Val Lys Tyr Asn Ser Ile Leu Ile Phe
            340                 345                 350

Gly Ile Asn Lys Gly Met Leu Asn Ser Pro Val Thr Asp Cys Leu Asn
        355                 360                 365

Asp His Arg Val Ala Met Met Ser Ser Ala Leu Ala Leu Val Asn Gly
    370                 375                 380
```

```
Gly Val Ile Thr Ser Ala Glu Cys Val Gly Lys Ser Asn Pro Asn Tyr
385                 390                 395                 400

Trp Gln Asp Leu Leu Ser Leu Asn Ala Lys Ile Ser Ile Glu
                405                 410
```

<210> SEQ ID NO 37
<211> LENGTH: 409
<212> TYPE: PRT
<213> ORGANISM: Pseudomonas putida

<400> SEQUENCE: 37

```
Met Gln Arg Ala Cys Ala Ala Leu Val Ala Lys Gly Ile Ser Glu
 1               5                  10                  15

Ile Ile Asn Pro Gly His Ser Asn Asp Lys Ala Ala Arg Asp Ile
                20                  25                  30

Val Ser Arg Leu Gly Ala Arg Leu Glu Asp Gln Pro Asp Gly Ser Leu
                35                  40                  45

Gln Ile Thr Ser Glu Gly Val Lys Pro Val Ala Pro Phe Ile Asp Cys
 50                  55                          60

Gly Glu Ser Gly Leu Ser Ile Arg Met Phe Thr Pro Ile Val Ala Leu
 65                  70                  75                  80

Ser Lys Glu Glu Val Thr Ile Lys Gly Ser Gly Ser Leu Val Thr Arg
                85                  90                  95

Pro Met Asp Phe Phe Asp Glu Ile Leu Pro His Leu Gly Val Lys Val
                100                 105                 110

Lys Ser Asn Gln Gly Lys Leu Pro Leu Val Ile Gln Gly Pro Leu Lys
                115                 120                 125

Pro Ala Asp Val Thr Val Asp Gly Ser Leu Ser Ser Gln Phe Leu Thr
130                 135                 140

Gly Leu Leu Leu Ala Tyr Ala Ala Asp Ala Ser Asp Val Ala Ile
145                 150                 155                 160

Lys Val Thr Asn Leu Lys Ser Arg Pro Tyr Ile Asp Leu Thr Leu Asp
                165                 170                 175

Val Met Lys Arg Phe Gly Leu Lys Thr Pro Glu Asn Arg Asn Tyr Glu
                180                 185                 190

Glu Phe Tyr Phe Lys Ala Gly Asn Val Tyr Asp Glu Thr Lys Met Gln
                195                 200                 205

Arg Tyr Thr Val Glu Gly Asp Trp Ser Gly Gly Ala Phe Leu Leu Val
                210                 215                 220

Ala Gly Ala Ile Ala Gly Pro Ile Thr Val Arg Gly Leu Asp Ile Ala
225                 230                 235                 240

Ser Thr Gln Ala Asp Lys Ala Ile Val Gln Ala Leu Met Ser Ala Asn
                245                 250                 255

Ala Gly Ile Ala Ile Asp Ala Lys Glu Ile Lys Leu His Pro Ala Asp
                260                 265                 270

Leu Asn Ala Phe Glu Phe Asp Ala Thr Asp Cys Pro Asp Leu Phe Pro
                275                 280                 285

Pro Leu Val Ala Leu Ala Ser Tyr Cys Lys Gly Glu Thr Lys Ile Lys
                290                 295                 300

Gly Val Ser Arg Leu Ala His Lys Glu Ser Asp Arg Gly Leu Thr Leu
305                 310                 315                 320

Gln Asp Glu Phe Gly Lys Met Gly Val Glu Ile His Leu Glu Gly Asp
                325                 330                 335

Leu Met Arg Val Ile Gly Gly Lys Gly Val Lys Gly Ala Glu Val Ser
                340                 345                 350
```

```
Ser Arg His Asp His Arg Ile Ala Met Ala Cys Ala Val Ala Ala Leu
            355                 360                 365

Lys Ala Val Gly Glu Thr Thr Ile Glu His Ala Glu Ala Val Asn Lys
    370                 375                 380

Ser Tyr Pro Asp Phe Tyr Ser Asp Leu Lys Gln Leu Gly Gly Val Val
385                 390                 395                 400

Ser Leu Asn His Gln Phe Asn Phe Ser
                405

<210> SEQ ID NO 38
<211> LENGTH: 419
<212> TYPE: PRT
<213> ORGANISM: Brevundomonas vesicularis

<400> SEQUENCE: 38

Met Met Met Gly Arg Ala Lys Leu Thr Ile Ile Pro Pro Gly Lys Pro
1               5                   10                  15

Leu Thr Gly Arg Ala Met Pro Pro Gly Ser Lys Ser Ile Thr Asn Arg
            20                  25                  30

Ala Leu Leu Leu Ala Gly Leu Ala Lys Gly Thr Ser Arg Leu Thr Gly
        35                  40                  45

Ala Leu Lys Ser Asp Asp Thr Arg Tyr Met Ala Glu Ala Leu Arg Ala
    50                  55                  60

Met Gly Val Thr Ile Asp Glu Pro Asp Asp Thr Thr Phe Ile Val Lys
65                  70                  75                  80

Gly Ser Gly Lys Leu Gln Pro Pro Ala Ala Pro Leu Phe Leu Gly Asn
                85                  90                  95

Ala Gly Thr Ala Thr Arg Phe Leu Thr Ala Ala Ala Leu Val Asp
            100                 105                 110

Gly Lys Val Ile Val Asp Gly Asp Ala His Met Arg Lys Arg Pro Ile
        115                 120                 125

Gly Pro Leu Val Asp Ala Leu Arg Ser Leu Gly Ile Asp Ala Ser Ala
    130                 135                 140

Glu Thr Gly Cys Pro Pro Val Thr Ile Asn Gly Thr Gly Arg Phe Glu
145                 150                 155                 160

Ala Ser Arg Val Gln Ile Asp Gly Gly Leu Ser Ser Gln Tyr Val Ser
                165                 170                 175

Ala Leu Leu Met Met Ala Ala Gly Gly Asp Arg Ala Val Asp Val Glu
            180                 185                 190

Leu Leu Gly Glu His Ile Gly Ala Leu Gly Tyr Ile Asp Leu Thr Val
        195                 200                 205

Ala Ala Met Arg Ala Phe Gly Ala Lys Val Glu Arg Val Ser Pro Val
    210                 215                 220

Ala Trp Arg Val Glu Pro Thr Gly Tyr His Ala Ala Asp Phe Val Ile
225                 230                 235                 240

Glu Pro Asp Ala Ser Ala Ala Thr Tyr Leu Trp Ala Ala Glu Val Leu
                245                 250                 255

Ser Gly Gly Lys Ile Asp Leu Gly Thr Pro Ala Glu Gln Phe Ser Gln
            260                 265                 270

Pro Asp Ala Lys Ala Tyr Asp Leu Ile Ser Lys Phe Pro His Leu Pro
        275                 280                 285

Ala Val Ile Asp Gly Ser Gln Met Gln Asp Ala Ile Pro Thr Leu Ala
    290                 295                 300

Val Leu Ala Ala Phe Asn Glu Met Pro Val Arg Phe Val Gly Ile Glu
```

```
                     305                 310                 315                 320

Asn Leu Arg Val Lys Glu Cys Asp Arg Ile Arg Ala Leu Ser Ser Gly
                325                 330                 335

Leu Ser Arg Ile Val Pro Asn Leu Gly Thr Glu Glu Gly Asp Asp Leu
                340                 345                 350

Ile Ile Ala Ser Asp Pro Ser Leu Ala Gly Lys Ile Leu Thr Ala Glu
                355                 360                 365

Ile Asp Ser Phe Ala Asp His Arg Ile Ala Met Ser Phe Ala Leu Ala
            370                 375                 380

Gly Leu Lys Ile Gly Gly Ile Thr Ile Leu Asp Pro Asp Cys Val Ala
385                 390                 395                 400

Lys Thr Phe Pro Ser Tyr Trp Asn Val Leu Ser Ser Leu Gly Val Ala
                405                 410                 415

Tyr Glu Asp
```